United States Patent
Witt et al.

(10) Patent No.: US 10,959,748 B2
(45) Date of Patent: *Mar. 30, 2021

(54) ULTRASONIC SURGICAL BLADE

(71) Applicant: Ethicon LLC, Guaynabo, PR (US)

(72) Inventors: David A. Witt, Maineville, OH (US); Timothy G. Dietz, Reading, MA (US); Stephen J. Balek, Springboro, OH (US); Benjamin M. Boyd, Fairborn, OH (US); David C. Groene, Cincinnati, OH (US); Benjamin V. Vins, Bangalore (IN); William C. Horton, III, Duxbury, MA (US); Ashvani K. Madan, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 306 days.

This patent is subject to a terminal disclaimer.

(21) Appl. No.: 15/801,777

(22) Filed: Nov. 2, 2017

(65) Prior Publication Data

US 2018/0125522 A1      May 10, 2018

Related U.S. Application Data

(63) Continuation of application No. 14/090,269, filed on Nov. 26, 2013, now Pat. No. 9,848,900.

(Continued)

(51) Int. Cl.
    *A61B 17/32*      (2006.01)

(52) U.S. Cl.
    CPC ........... *A61B 17/320068* (2013.01); *A61B 2017/320069* (2017.08); *A61B 2017/320071* (2017.08);

(Continued)

(58) Field of Classification Search
    CPC ........ A61B 17/320068; A61B 17/1637; A61B 2017/320072; A61B 2017/320096;

(Continued)

(56) References Cited

U.S. PATENT DOCUMENTS

| | | |
|---|---|---|
| 80,242 A | 7/1868 | Tongue |
| D37,007 S | 6/1904 | Munro |

(Continued)

FOREIGN PATENT DOCUMENTS

| | | |
|---|---|---|
| CA | 159776 S | 8/2015 |
| EP | 0 968 684 A1 | 1/2000 |

(Continued)

OTHER PUBLICATIONS

COBBRA Energized Cobb Elevator, Product Flyer, Elliquence, LLC, 2012, 2 pgs.

(Continued)

*Primary Examiner* — Katherine M Shi
*Assistant Examiner* — Lindsey Bachman
(74) *Attorney, Agent, or Firm* — Frost Brown Todd LLC

(57) ABSTRACT

An ultrasonic instrument comprises an ultrasonic transducer, an acoustic waveguide, and an ultrasonic blade. The blade includes a pair of obliquely extending edges. The obliquely extending edges diverge away from the longitudinal axis of the waveguide and away from each other along respective paths extending distally in relation to the waveguide. A distal portion of the blade is wider than a proximal portion of the blade along a plane. The blade further includes a curved distal edge and several laterally presented surfaces. The laterally presented surfaces may provide combinations of concave and convex curvatures. The laterally presented surfaces may be angled and/or curved along one or more orthogonal planes associated with the longitudinal axis of the waveguide.

18 Claims, 58 Drawing Sheets

Related U.S. Application Data

(60) Provisional application No. 61/734,636, filed on Dec. 7, 2012.

(52) U.S. Cl.
CPC ............ A61B 2017/320077 (2017.08); A61B 2017/320089 (2017.08); A61B 2017/320098 (2017.08)

(58) Field of Classification Search
CPC ........... A61B 2090/0817; A61B 2017/320069; A61B 2017/320071; A61B 2017/320073; A61B 2017/320074; A61B 2017/320075; A61B 2017/320077; A61B 2017/320078; A61B 2017/320082; A61B 2017/320088; A61B 2017/320089; A61B 2017/32009; A61B 2017/320092; A61B 2017/320093; A61B 2017/320094; A61B 2017/320095; A61B 2017/320097; A61B 2017/320098; A61B 2002/2864; A61B 2002/4683; A61F 9/00745
USPC ................. 606/167, 169, 170, 171; D24/146
See application file for complete search history.

(56) References Cited

U.S. PATENT DOCUMENTS

| | | |
|---|---|---|
| 3,990,452 A | 11/1976 | Murry et al. |
| 5,023,988 A | 6/1991 | Lamond |
| D339,419 S | 9/1993 | Hood et al. |
| 5,261,922 A | 11/1993 | Hood |
| D342,313 S | 12/1993 | Hood et al. |
| D344,801 S | 3/1994 | Hughes et al. |
| D346,024 S | 4/1994 | Hood et al. |
| 5,318,570 A | 6/1994 | Hood et al. |
| 5,322,055 A | 6/1994 | Davison et al. |
| 5,324,299 A | 6/1994 | Davison et al. |
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| D450,676 S | 11/2001 | Huttner |
| 6,325,811 B1 | 12/2001 | Messerly |
| 6,328,751 B1* | 12/2001 | Beaupre .......... A61B 17/320068 606/169 |
| 6,423,082 B1* | 7/2002 | Houser .......... A61B 17/320068 606/169 |
| 6,436,115 B1 | 8/2002 | Beaupre |
| 6,514,267 B2* | 2/2003 | Jewett ............ A61B 17/320068 606/169 |
| 6,585,745 B2 | 7/2003 | Cimino |
| D483,870 S | 12/2003 | Scheller et al. |
| 6,660,017 B2 | 12/2003 | Beaupre |
| 6,773,444 B2 | 8/2004 | Messerly |
| 6,783,524 B2 | 8/2004 | Anderson et al. |
| 6,790,211 B1 | 9/2004 | McPherson et al. |
| 6,976,969 B2 | 12/2005 | Messerly |
| D515,213 S | 2/2006 | Huttner |
| D546,948 S | 7/2007 | Huttner |
| 7,300,446 B2 | 11/2007 | Beaupre |
| 7,445,624 B2 | 11/2008 | Freier et al. |
| D603,046 S | 10/2009 | Frey |
| D612,049 S | 3/2010 | Baynham |
| 7,758,600 B2 | 7/2010 | Beaupre |
| 8,002,783 B2 | 8/2011 | Vercellotti et al. |
| 8,016,843 B2 | 9/2011 | Escaf |
| 8,057,498 B2 | 11/2011 | Robertson |
| 8,152,825 B2 | 4/2012 | Madan et al. |
| 8,241,312 B2 | 8/2012 | Messerly |
| D667,117 S | 9/2012 | Darian et al. |
| 8,313,489 B2 | 11/2012 | Adams et al. |
| 8,343,178 B2 | 1/2013 | Novak et al. |
| D680,218 S | 4/2013 | Darian et al. |
| D685,087 S | 6/2013 | Voic |
| 8,461,744 B2 | 6/2013 | Wiener et al. |
| 8,591,536 B2 | 11/2013 | Robertson |
| D697,207 S | 1/2014 | Paget et al. |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| D749,730 S | 2/2016 | Dietz et al. |
| 9,265,524 B2 | 2/2016 | Derwin et al. |
| 9,277,928 B2 | 3/2016 | Lopez |
| 9,358,030 B2 | 6/2016 | Young et al. |
| 9,381,058 B2 | 7/2016 | Houser et al. |
| 9,393,037 B2 | 7/2016 | Olson et al. |
| 9,848,900 B2 | 12/2017 | Witt et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0326535 A1 | 12/2009 | Blus |
| 2010/0057118 A1* | 3/2010 | Dietz ............ A61B 17/320068 606/169 |
| 2011/0160624 A1* | 6/2011 | Babaev ............ A61M 35/003 601/2 |
| 2012/0116265 A1 | 5/2012 | Houser et al. |
| 2013/0103066 A1 | 4/2013 | Rad |
| 2013/0116717 A1 | 5/2013 | Balek et al. |

FOREIGN PATENT DOCUMENTS

| | | |
|---|---|---|
| EP | 1 110 509 A1 | 6/2001 |
| EP | 2 438 876 A1 | 4/2012 |
| GB | 2 365 775 A | 2/2002 |
| GB | 2 442 137 A | 3/2008 |
| JP | H02-286149 A | 11/1990 |
| JP | 2001-104314 A | 4/2001 |
| JP | 2009-539500 A | 11/2009 |
| JP | 2014-518669 A | 8/2014 |
| WO | WO 2012/149361 A1 | 11/2012 |

OTHER PUBLICATIONS

Australian Office Action, Examination report No. 1 for standard patent appication, dated Jul. 3, 2017 for Application No. AU 2013356362, 4 pgs.
Chinese Office Action, Notification of the First Office Action, dated Dec. 5, 2016 for Application No. 2013800639273, 10 pgs.
Chinese Search Report dated Nov. 27, 2016 for Application No. CN 2013800639273, 3 pgs.
International Search Report dated Apr. 3, 2014 for Application No. PCT/US2013/072139, 5 pgs.
International Preliminary Report on Patentability and Written Opinion dated Jun. 9, 2015 for Application No. PCT/US2013/072139, 8 pages.
Japanese Office Action, Notification of Reasons for Refusal, dated Jul. 25, 2017 for Application No. JP 2015-546516, 4 pgs.
Japanese Search Report dated Jun. 19, 2017 for Application No. JP 2015-546516, 19 pgs.
Japanese Office Action, Decision of Refusal, dated Jan. 9, 2018 for Application No. JP 2015-546516, 6 pgs.
U.S. Appl. No. 61/410,603, filed Nov. 5, 2010.
U.S. Appl. No. 61/734,636, filed Dec. 7, 2012.
European Search Report, Extended, and Written Opinion dated Nov. 25, 2020 for Application No. EP 20173975.2, 8 pgs.

\* cited by examiner

ULTRASONIC SURGICAL BLADE

PRIORITY

This application is a continuation of U.S. application Ser. No. 14/090,269, entitled "Ultrasonic Surgical Blade," filed Nov. 26, 2013, now U.S. Pat. No. 9,848,900, issued Dec. 26, 2017 which claims priority to U.S. Provisional Patent App. No. 61/734,636, entitled "Ultrasonic Surgical Blade," filed Dec. 7, 2012, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; and U.S. Pat. No. 8,057,498, entitled "Ultrasonic Surgical Instrument Blades," issued Nov. 15, 2011, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published. Aug. 21, 2008, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical instruments," published Jan. 20, 2011 now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued Jul. 19, 2016, the disclosure of which is incorporated by reference herein; and U.S. patent application Ser. No. 13/657,553, filed. Oct. 22, 2012, entitled "Flexible Harmonic Waveguides/Blades for Surgical Instruments." now U.S. Pat. No. 9,095,367, issued Aug. 4, 2015, the disclosure of which is incorporated by reference herein.

The shape of an ultrasonic blade used in an ultrasonic surgical instrument may influence or define at least four aspects of the instrument. These aspects may include the visibility of the blade and its relative position in the surgical field; the ability of the blade to access or approach targeted tissue; the manner in which ultrasonic energy is coupled to tissue for cutting and coagulation; and the manner in which tissue can be manipulated with the ultrasonically inactive blade. It may be desirable to provide an ultrasonic blade that tends to optimize at least these four aspects of the instrument.

Some conventional ultrasonic blades may be optimized for use on soft tissues. When some such ultrasonic blades encounter a continuum of tissue that ranges from relatively soft tissue (e.g., viscera, etc.) to relatively tough tissue (e.g., cartilage, etc.), the ultrasonic blade may preferentially cut the soft tissues. When the ultrasonic blade encounters relatively tough or hard tissue, the ultrasonic may tend to deflect away from the relatively tough or hard tissue, continuing along the path of least resistance through the relatively soft tissue. While such performance may be preferred for dissecting between planes of tissue, such performance may make it difficult to use ultrasonic blade to intentionally cut through relatively tough or hard tissue (e.g., cartilage, etc.).

In some surgical settings, a surgeon may use a Cobb elevator instrument in conjunction with a bovie monopolar electrocautery device to expose the dorsal spine of a patient. In particular, the surgeon may use the Cobb elevator to provide a combination of blunt and sharp dissection, prying and scraping to expose and clean the surface of the bone of all soft tissue. The surgeon may use the bovie device to control hemostasis and cut/burn through tougher tissues such as tendon attachments to bone. In some such procedures, a goal may be to provide a clean bone surface, in order to facilitate hardware placement (e.g., rods, screws, etc.) and/or fusion of selected bones.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
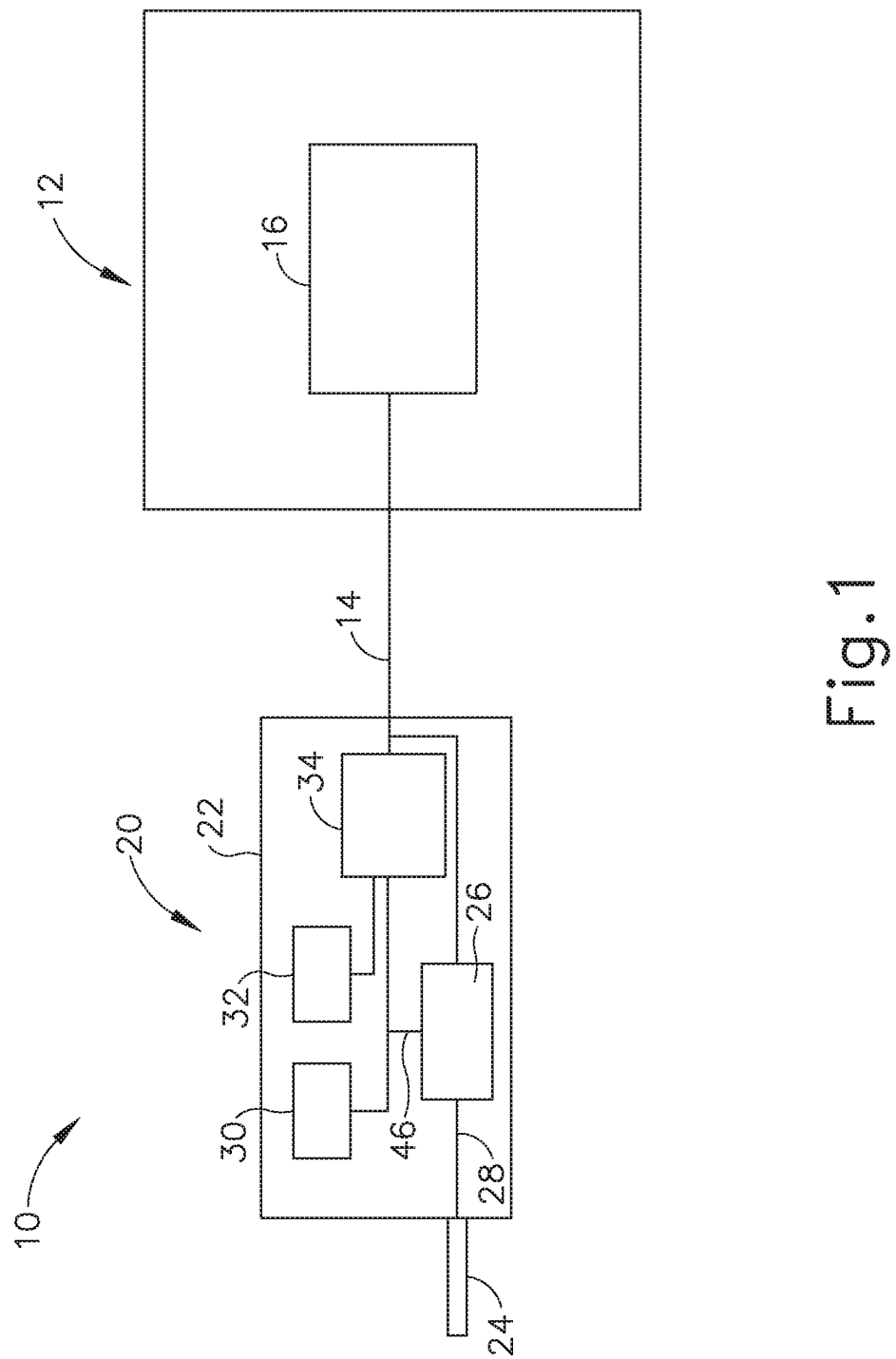
FIG. 1 depicts a block schematic view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04 or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011 now U.S. Pat. No. 8,986,302 issued Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (n$\lambda$/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes HF105 and DH105 by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12)) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (6) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
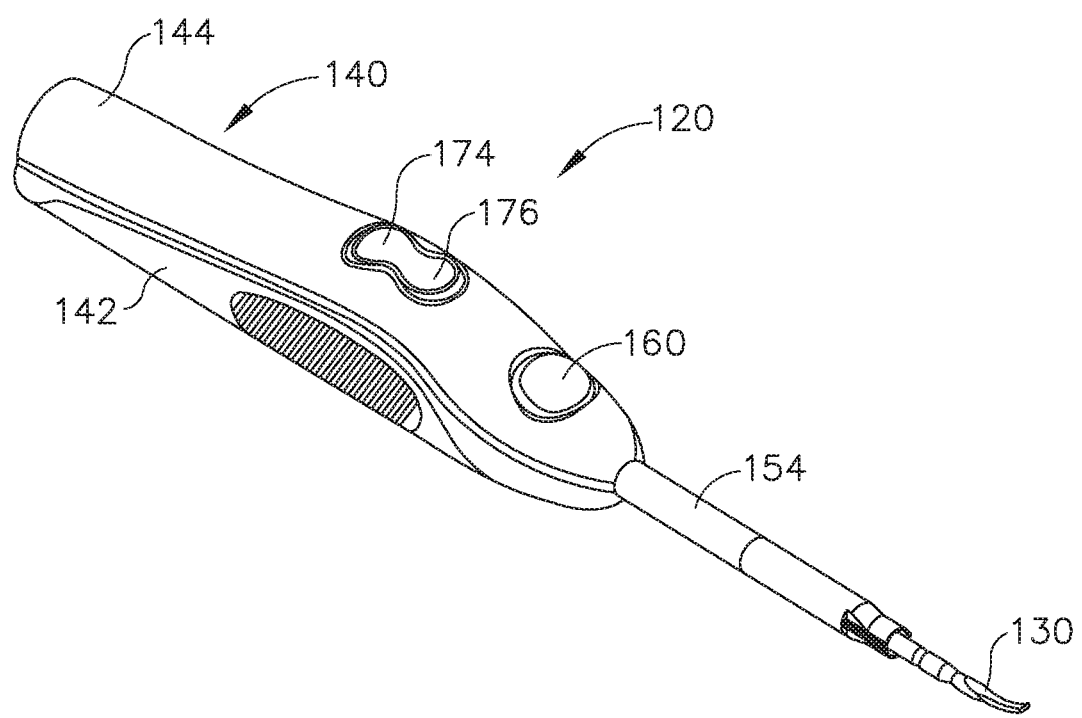
FIG. 2 depicts a perspective view of an exemplary ultrasonic surgical instrument that may form part of the system of FIG. 1.
Figure 3:
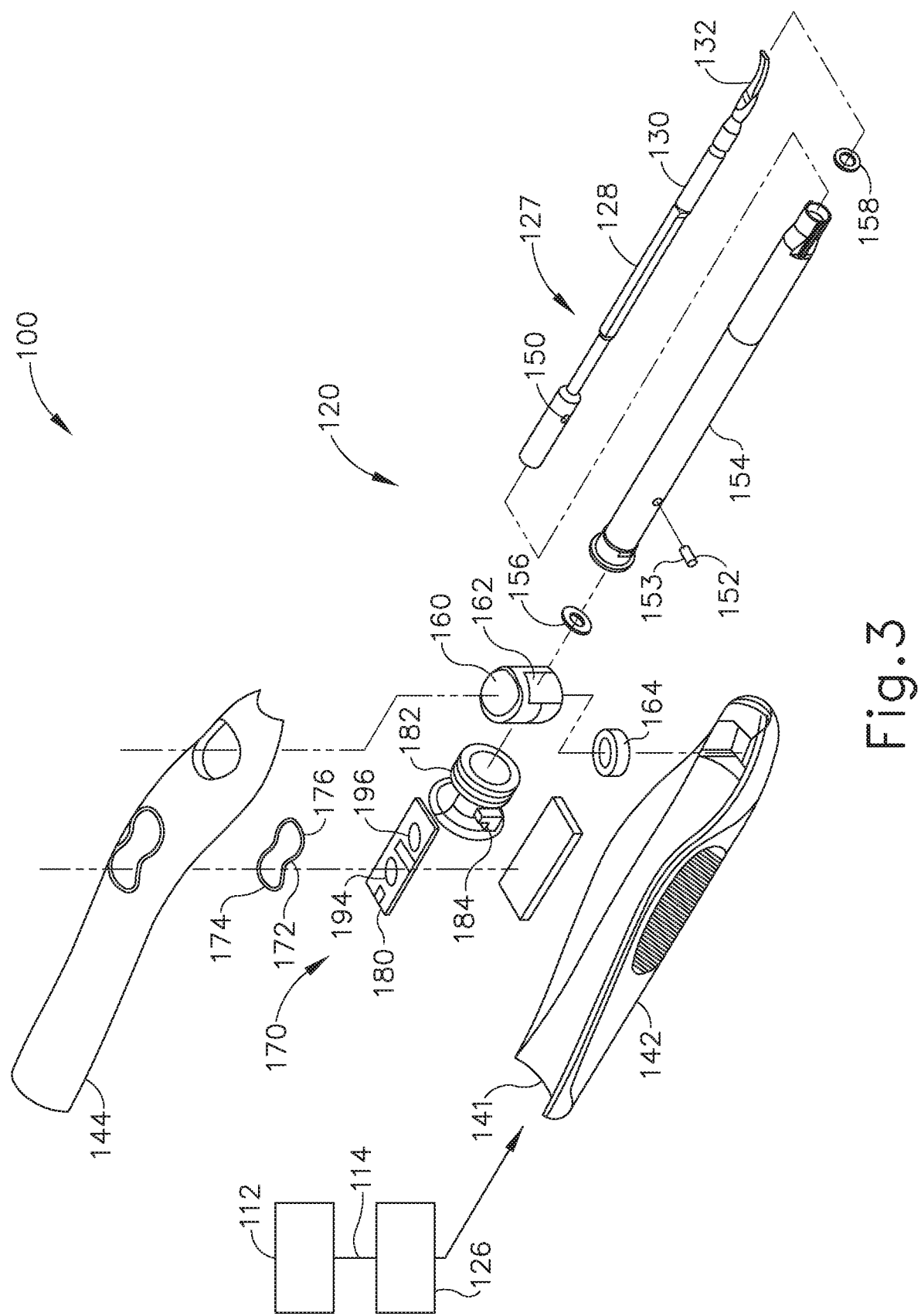
FIG. 3 depicts an exploded view of the instrument of FIG. 2.

FIGS. 2-3 depict an exemplary ultrasonic surgical instrument (120), which is part of an ultrasonic surgical system (100) that includes an ultrasonic transducer (126) coupled with an ultrasonic generator (112) via a cable (114). Instrument (120) also includes an ultrasonic transmission assembly (127), which is mechanically and acoustically coupled with ultrasonic transducer (126). In some versions, ultrasonic transmission assembly (127) is coupled with ultrasonic transducer (126) by a threaded connection, though any other suitable type of coupling may be used. Ultrasonic transmission assembly (127) comprises an ultrasonic waveguide (128) and blade (130). As will be apparent to those of ordinary skill in the art, when ultrasonic transducer (126) is powered by generator (112), ultrasonic transducer (126) produces ultrasonic vibrations, which are communicated to blade (130) via ultrasonic waveguide (128). This causes tip (132) of blade (130) to vibrate at an ultrasonic frequency, allowing blade (130) to be used to cut and coagulate tissue, etc. Thus, generator (112), transducer (126), waveguide (128), and blade (130) operate just like generator (12), transducer (26), waveguide (28), and blade (24) described above.

Instrument (120) of the present example further comprises a multi-piece handle assembly (140) that is configured to substantially isolate the operator from the vibrations of the piezoelectric assembly contained within transducer (126). By way of example only, handle assembly (140) may be shaped to be grasped and manipulated in a pencil-like arrangement. Handle assembly (140) of the present example comprises mating housing portions (142) and (144). While a multi-piece handle assembly (140) is illustrated, handle assembly (140) may alternatively comprise a single or unitary component. Handle assembly (140) may be constructed from a durable plastic, such as polycarbonate or a liquid crystal polymer. It is also contemplated that handle assembly (140) may alternatively be made from a variety of materials or combinations of materials, including but not limited to other plastics, ceramics, and/or metals, etc. In some versions, the proximal end of instrument (120) receives and is fitted with ultrasonic transducer (126) by insertion of ultrasonic transducer (126) into handle assembly (140). Instrument (120) may be attached to and removed from ultrasonic transducer (126) as a unit. The elongated transmission assembly (127) of the instrument (120) extends orthogonally from instrument handle assembly (140).

Ultrasonic waveguide (128), which is configured to transmit ultrasonic energy from transducer (126) to the tip (132) of blade (130), may be flexible, semi-flexible or rigid. Ultrasonic waveguide (128) may also be configured to amplify the mechanical vibrations transmitted through ultrasonic waveguide (128) to blade (130). Ultrasonic waveguide (128) may further include at least one radial aperture (150) extending therethrough, substantially perpendicular to the longitudinal axis of ultrasonic waveguide (128). Aperture (150) is located at a longitudinal position corresponding to a node associated with ultrasonic vibrations communicated along waveguide (128). Aperture (150) is configured to receive a connector pin (152), discussed below, which connects ultrasonic waveguide (128) to an outer sheath (154). Proximal O-ring (156) and distal o-ring (158) are assembled onto transmission assembly (127) near longitudinal positions corresponding to nodes associated with ultrasonic vibrations communicated along waveguide (128) in the present example, though various other components or configurations may be used.

Blade (130) may be integral with ultrasonic waveguide (128) and formed as a single unit. In some versions, blade (130) may be connected by a threaded connection, a welded joint, and/or some other coupling feature(s). The distal end of blade (130), or blade tip (132), is disposed at or near a longitudinal position corresponding to an anti-node associated with ultrasonic vibrations communicated along waveguide (128) and blade (130) in order to tune the acoustic assembly to a preferred resonant frequency $f_o$ when the acoustic assembly is not loaded by tissue. When ultrasonic transducer (126) is energized, blade tip (132) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. Blade tip (132) may also vibrate in the y-axis at about 1 to about 110 percent of the motion in the x-axis. Of course, movement of blade tip (132) may alternatively have any other suitable characteristics.

Ultrasonic waveguide (128) is positioned within outer sheath (154) and held in place via pin (152). Pin (152) may be made of any compatible metal, such as stainless steel or titanium or a durable plastic, such as polycarbonate or a liquid crystal polymer. Alternatively, any other suitable material or combination of materials may be used. In some versions, pin (152) is partially coated with an elastomeric material, such as silicon, etc., for that portion (153) of pin (152) that extends through ultrasonic waveguide (128). Elastomeric material may provide insulation from the vibrating blade throughout the length of hole (152). In some settings, this may enable high efficiency operation whereby minimal overheating is generated and maximum ultrasonic output power is available at blade tip (132) for cutting and coagulation, etc. Of course, such elastomeric material is merely optional.

Outer sheath (154) passes through an aperture (162) of release button (160). A spring (164) is positioned below release button (160) and resiliently biases release button (160) upwardly. The upward force imposed by spring (164) causes the perimeter of aperture (162) to firmly assert pressure against outer sheath (154), and thereby selectively prevents outer sheath (154), ultrasonic waveguide (128), and blade (130) from either rotating within handle (140) or axially translating with respect to handle (140). When the operator exerts a downward force on release button (160), spring (164) is compressed and it no longer asserts a holding force on outer sheath (154). The operator may then axially translate outer sheath (154), ultrasonic waveguide (128), and blade (130) relative to handle (140) and/or rotate outer sheath (154), ultrasonic waveguide (128), and blade (130) relative to handle (140). Accordingly, it should be understood that the longitudinal and/or rotational position of blade (130) relative to handle (140) may be selectively adjusted by the operator while depressing release button (160), while still allowing blade (130) to vibrate ultrasonically at such selected positions, allowing blade (130) to be used in various surgical procedures at such selected positions. To initiate such ultrasonic action of blade (130), the operator may operate a footswitch (not shown), activate a pushbutton (174, 176) as described below, activate a button on generator (112), or perform some other act on some component of system (100).

In the present example, housing of handle (140) includes a proximal end, a distal end, and a cavity (141) extending longitudinally therein. Cavity (141) is configured to accept a switch assembly (170) and at least a portion of ultrasonic transducer assembly (126). In one some versions, the distal end of ultrasonic transducer assembly (126) threadably attaches to the proximal end of ultrasonic waveguide (128), though any other suitable type of coupling may be used. Electrical contacts of ultrasonic transducer (126) also interface with switch assembly (170) to provide the operator with finger-activated controls on surgical instrument (120). Ultrasonic transducer (126) of the present example includes two conductive rings (not shown) which are securely disposed within the body of ultrasonic transducer (126) as is described in U.S. Pub. No. 2007/0106158, entitled. "Medical Ultrasound System and Handpiece and Methods for Making and Tuning," published May 10, 2007, now U.S. Pat. No. 8,152,825, issued. Apr. 10, 2012, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (140) by way of corresponding supporting mounts on switch housing (182) and housing portions (142, 144).

Pushbutton assembly (172) of the present example comprises pushbuttons (174, 176). Circuit assembly (180) provides for the electro-mechanical interface between pushbuttons (174, 176) and generator (112) via ultrasonic transducer (126). Circuit assembly (180) comprises two dome switches (194, 196) that are mechanically actuated by depressing pushbuttons (174, 176) respectively. Dome switches (194, 196) are electrical contact switches, that when depressed provide an electrical signal to generator (112). Pins (not shown) are electrically connected to dome switches (194, 196). In particular, one end of each pin is electrically connected to a corresponding dome switch (194, 196). The other end of each pin is electrically connected with a corresponding ring conductor at the distal end of ultrasonic transducer (126). That is, the pins each have spring-loaded tips that interface with ultrasonic transducer (126) in a manner similar to that described above. Circuit assembly (180) also comprises two diodes within a diode package (not shown) that connect to the pins, respectively. While the pins provide electrical contact to the ring conductors of ultrasonic transducer, the ring conductors are in turn connected to conductors in cable (114) that connects to generator (112). Of course a variety of alternative configurations may be used.

By depressing pushbuttons (174, 176), the corresponding contact surfaces depress corresponding dome switches (194, 196) to selectively activate the circuit (180). For instance, when the operator depresses pushbutton (174), generator (112) may respond with a certain energy level, such as a maximum ("max") power setting. When the operator depresses pushbutton (176), generator (112) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability.

In addition to or in lieu of being constructed in accordance with the above teachings, at least part of instrument (120) may be constructed and operable in accordance with at least some of the teachings of U.S. Pat. Nos. 5,322,055; 5,873, 873; 5,980,510; 6,283,981; 6,309,400; 6,325,811; 6,423, 082; 6,783,524; 8,057,498; U.S. Pub. No. 2006/0079874; U.S. Pub. No. 2007/0191713; U.S. Pub. No. 2007/0282333; U.S. Pub. No. 2008/0200940; U.S. Pub. No. 2008/0234710, now U.S. Pat. No. 8,911,460; U.S. Pub. No. 2010/0069940, now U.S. Pat. No. 9,023,071; U.S. Pub. No. 2011/0015660 now U.S. Pat. No. 8,461,744; U.S. Pub. No. 2012/0112687, now U.S. Pat. No. 9,381,058; U.S. Pub. No. 2012/0116265; U.S. patent application Ser. No. 13/538,588, now U.S. Pat. No. 9,393,037; U.S. patent application Ser. No. 13/657,553, now U.S. Pat. No. 9,095,367; and/or U.S. Pat. App. No. 61/410,603. The disclosures of each of the foregoing patents, publications, and applications are incorporated by reference herein. It should also be understood that instrument (120) may have various structural and functional similarities with the HARMONIC ACE® Ultrasonic Shears, the HARMONIC WAVER Ultrasonic Shears, the HARMONIC FOCUS® Ultrasonic Shears, and/or the HARMONIC SYNERGY® Ultrasonic Blades. Furthermore, instrument (120) may have various structural and functional similarities with the devices taught in any of the other references that are cited and incorporated by reference herein. Additional merely illustrative variations for instrument (120) will be apparent to those of ordinary skill in the art in view of the teachings herein. It should be understood that the below described variations may be readily applied to instrument (120) described above and any of the instruments referred to in any of the references that are cited herein, among others.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (20), there is no intent for any of the description herein to be presumed as admitted prior art. Several teachings herein in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

III. Exemplary Ultrasonic Blade Variations

As noted above, some conventional ultrasonic blades may be best suited for only cutting through relatively soft tissues; and/or separating soft tissue from relatively tough/hard tissues. It may therefore be desirable to provide an ultrasonic blade that is operable to cut through relatively soft tissues and relatively tough/hard tissues more easily than conventional ultrasonic blades. As also noted above, some surgeons may be familiar with using a combination of a Cobb elevator instrument (e.g., 10 mm, 13 mm, 15 mm, etc.) with a bovie device to clean soft and hard tissue from vertebrae in preparation for subsequent hardware installation, bone fusion, etc. It may therefore be desirable to provide an ultrasonic blade that is operable to cut through both soft and hard/tough tissues and further clean such tissue from vertebrae, without gouging the bone. Moreover, it may be desirable for such a blade to provide hemostasis during such a procedure, effectively eliminating the need for another instrument such as a bovie device; and to also feel like a conventional Cobb elevator instrument from the surgeon's perspective. An ultrasonic surgical instrument having such a blade may thus functionally substitute the combination of a Cobb elevator instrument and bovie device while also providing the kind of operator control that a surgeon may be familiar with from previously using a Cobb elevator instrument. The examples described below include variations of ultrasonic blades that may meet some or all of the above criteria.

The various examples of ultrasonic blades described below may be configured to provide vibrational movement along a longitudinal axis of the waveguide when the blade is activated with ultrasonic vibrations. In addition, the vibrational movement may be lateral to the longitudinal axis along one or more planes. It should therefore be understood that the various examples of ultrasonic blades described below may provide non-longitudinal modes of resonance. Providing such lateral or transverse modes of resonance may produce a motion more akin to scraping and less akin to jackhammering. Such lateral or transverse modes of resonance may thus promote scraping of tissue from bone. Moreover, such lateral or transverse modes of resonance may reduce the risk of the blade breaking and/or gouging the bone. In other words, the lateral or transverse modes of resonance may provide a glancing blow across the bone surface rather than a direct impact perpendicular to the bone surface. By way of example only, any of the ultrasonic blades described below may be driven such that they vibrate with a longitudinal displacement of approximately 95 microns and a lateral displacement of approximately 56 microns, yielding a ratio of approximately 0.6. In other words, the lateral motion of the blade may be approximately 60% of the longitudinal motion. Other suitable displacement amounts in the longitudinal and lateral direction, as wells as other suitable displacement ratios, will be apparent to those of ordinary skill in the art in view of the teachings herein.

Of course, the examples of variations of ultrasonic blades described below may also be used in other surgical contexts, including but not limited to those calling for scraping or general soft tissue cutting and coagulation. By way of example only, the examples of variations of ultrasonic blades described below may be used in plastic surgeries, breast augmentation or reduction surgeries, and/or various other kinds of surgeries. In some instances where a conventional ultrasonic blade is used, soft tissues may be difficult to suspend and place in tension so that the ultrasonic blade may provide sufficient pressure to achieve a cutting action. The structural characteristics of the variations of ultrasonic blades described below may allow the surgeon to use the blade to suspend the tissue and thereby place the tissue in tension for cutting with relative ease.

It should be understood that the below described examples of variations of ultrasonic blades may be used as substitutes for blades (24, 130) described above. In other words, the blades described below may be readily incorporated into instruments (10, 120) described above. To the extent that such incorporation of the below described blades may warrant additional modifications to instruments (10, 120), examples of such modifications will be apparent to those of ordinary skill in the art in view of the teachings herein.

A. Exemplary Ultrasonic Blade with Cobb Tip

Figure 4:
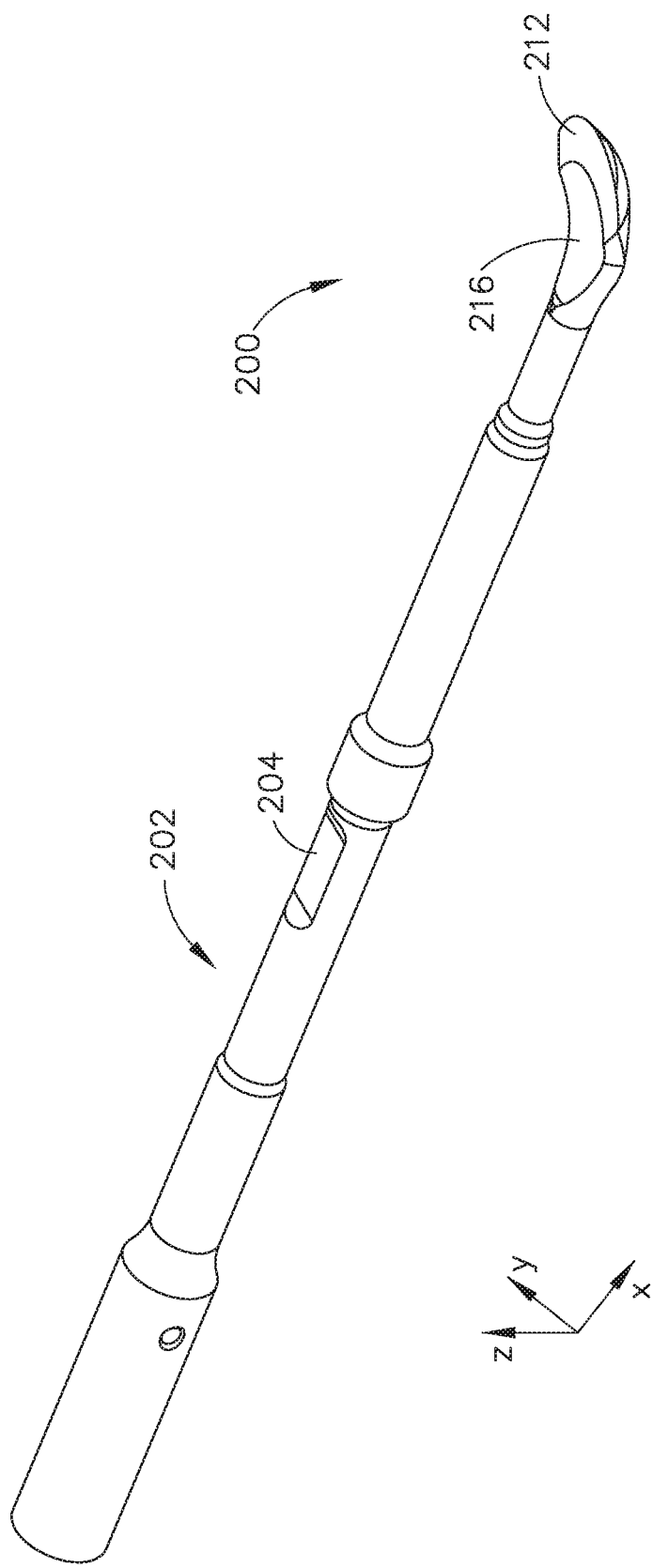
FIG. 4 depicts a top perspective view of an exemplary alternative ultrasonic blade and waveguide suitable for incorporation in the instrument of FIG. 2.
Figure 5:
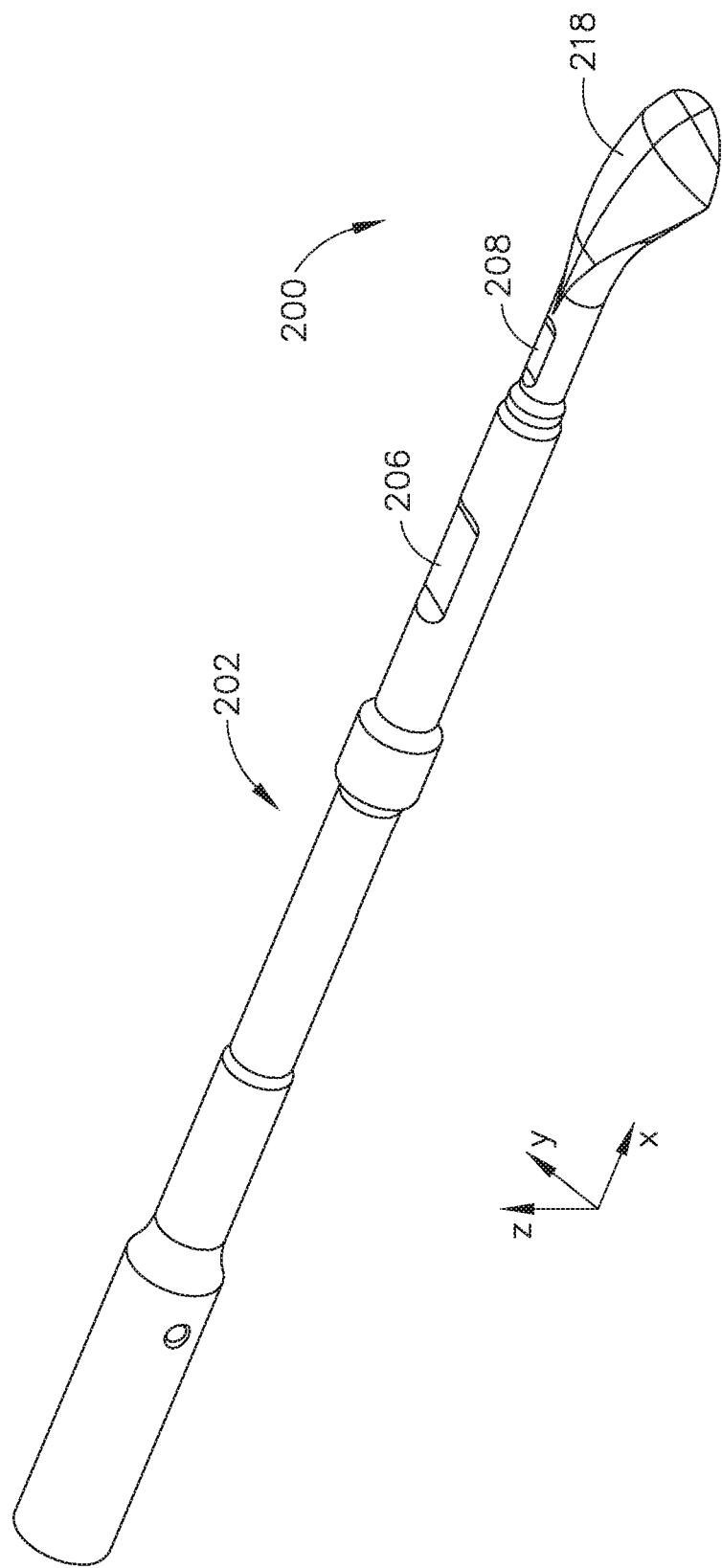
FIG. 5 depicts a bottom perspective view of the blade and waveguide of FIG. 4.
Figure 6:
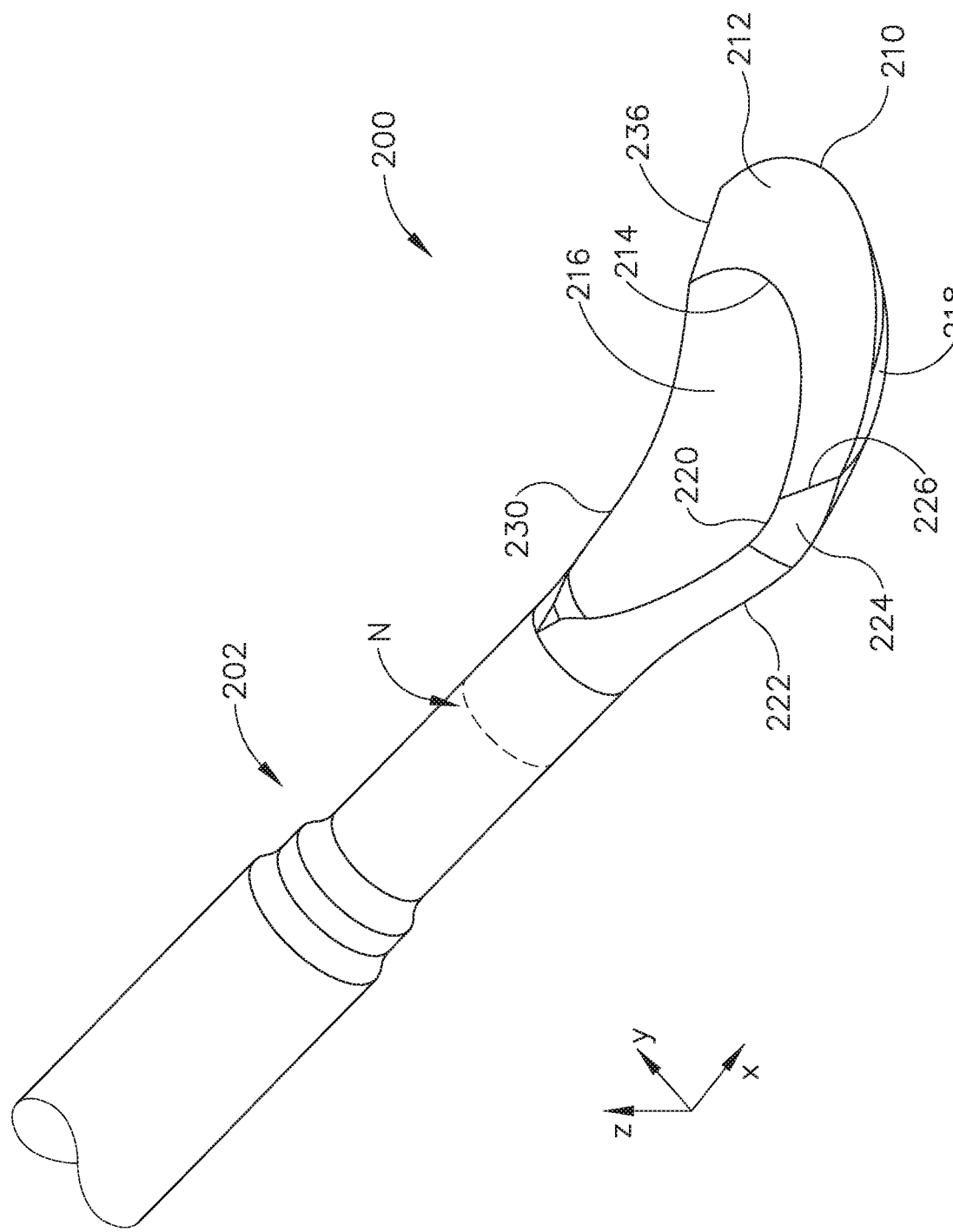
FIG. 6 depicts a top perspective view of the blade of FIG. 4.
Figure 7:
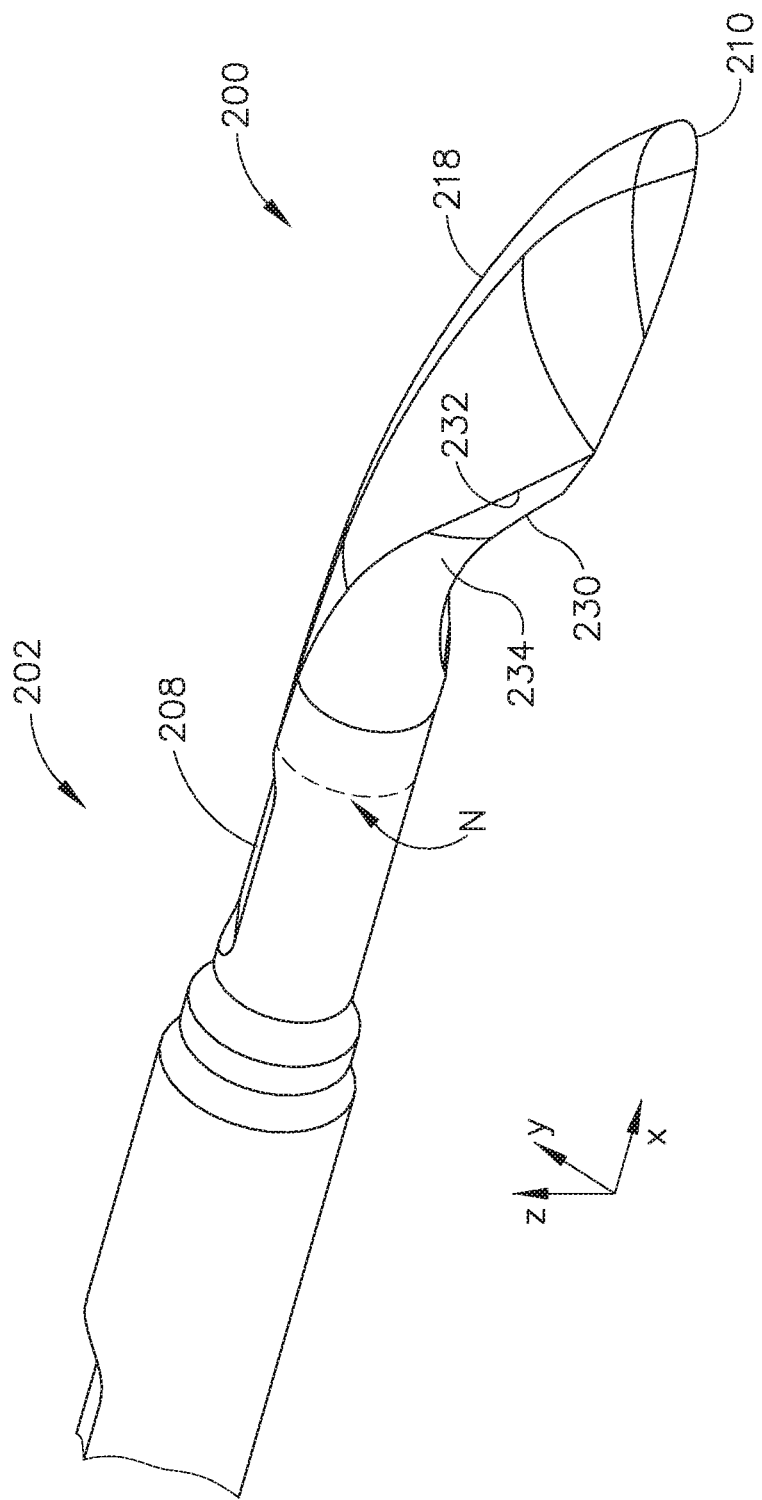
FIG. 7 depicts a bottom perspective view of the blade of FIG. 4.

FIGS. 4-17 show an exemplary alternative ultrasonic blade (200) and waveguide (202) that may be readily incorporated into instrument (20, 120). In particular, blade (200) and waveguide (202) may be mechanically and acoustically coupled with transducer (26, 126) in place of waveguide (28, 128) and blade (24, 132). As best seen in FIGS. 4-5, waveguide (202) of this example includes a set of flats (204, 206, 208). Flats (204, 206, 208) are configured and positioned to provide appropriate acoustic tuning of blade (200). In some versions, blade (200) provides an acoustic gain between approximately 3.0 and approximately 5.0. In the present example, blade (200) and waveguide (202) are configured such that a distal-most node (N) is located just proximal to blade (200). It should be understood that the distal-most node (N) corresponds to a node associated with resonant ultrasonic vibrations communicated through waveguide (202) and blade (200). When blade (200) is activated with ultrasonic vibrations, the vibrational movement may be along the longitudinal axis (LA). In addition, the vibrational movement may be in an angular movement (arrow (290) in 11) along the x-z plane, about a pitch axis passing through the longitudinal axis (LA) at the distal-most node (N). Furthermore, the vibrational movement may be in an angular movement (arrow (292) in FIG. 8) along the x-y plane, about a yaw axis passing through the longitudinal axis (LA) at the distal-most node (N). It should therefore be understood that blade (200) may provide non-longitudinal modes of resonance.

By way of example only, when blade (200) is activated to vibrate at an ultrasonic frequency, the ratio of lateral displacement of blade (200) from the longitudinal axis (LA) to the longitudinal displacement of blade (200) along the longitudinal axis (LA) is between approximately 0.46 to approximately 0.80. As another merely illustrative example, the ratio of lateral displacement of blade (200) from the longitudinal axis (LA) to the longitudinal displacement of blade (200) along the longitudinal axis (LA) is between approximately 0.60 to approximately 0.70. As another merely illustrative example, the ratio of lateral displacement of blade (200) from the longitudinal axis (LA) to the longitudinal displacement of blade (200) along the longitudinal axis (LA) is between approximately 0.70 to approximately 0.80. As yet another merely illustrative example, the ratio of lateral displacement of blade (200) from the longitudinal axis (LA) to the longitudinal displacement of blade (200) along the longitudinal axis (LA) is between approximately 0.46 to approximately 0.55. As yet another merely illustrative example, the ratio of lateral displacement of blade (200) from the longitudinal axis (LA) to the longitudinal displacement of blade (200) along the longitudinal axis (LA) is between approximately 0.60 to approximately 0.65.

Figure 8:
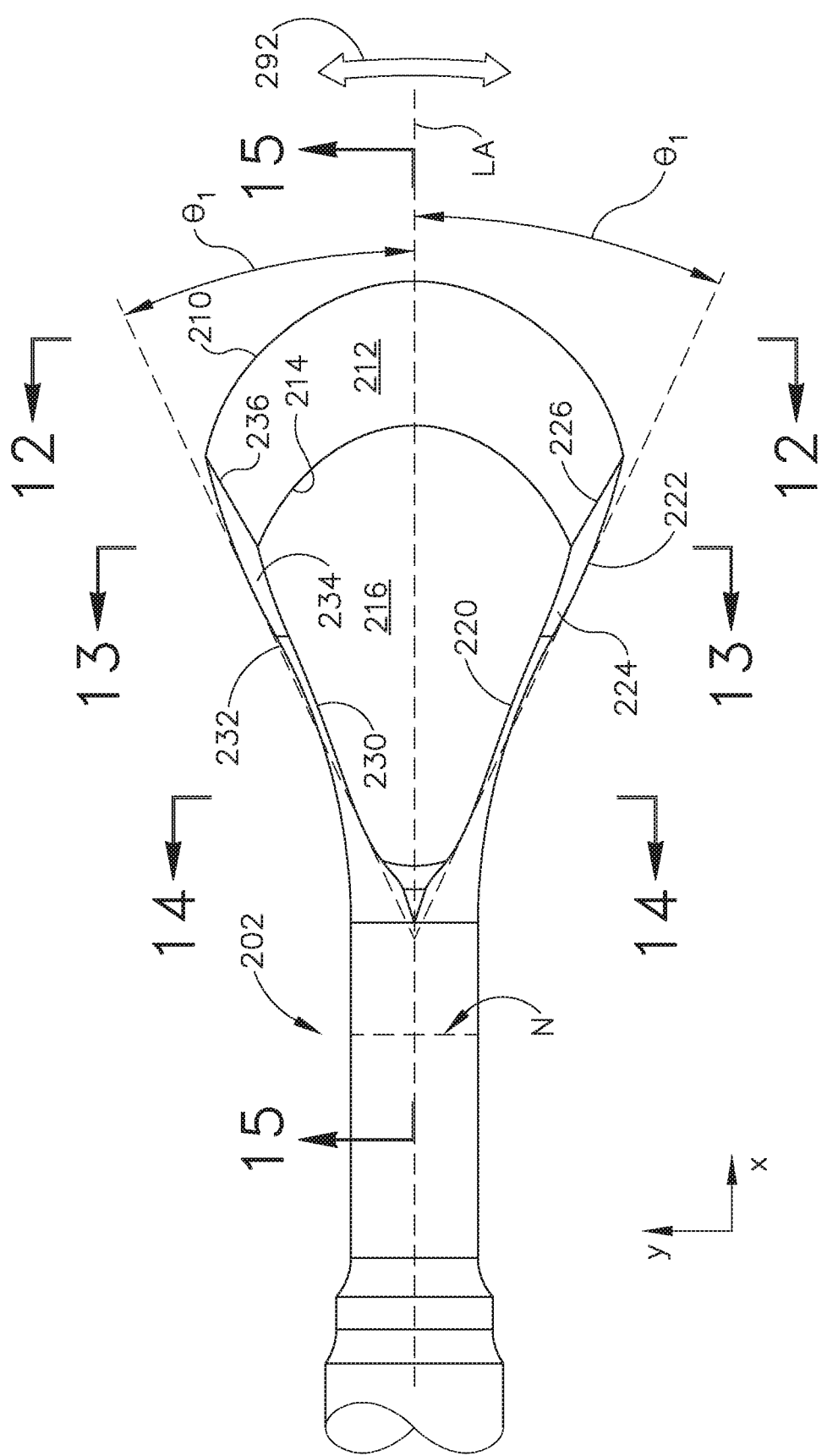
FIG. 8 depicts a top plan view of the blade of FIG. 4.
Figure 9:
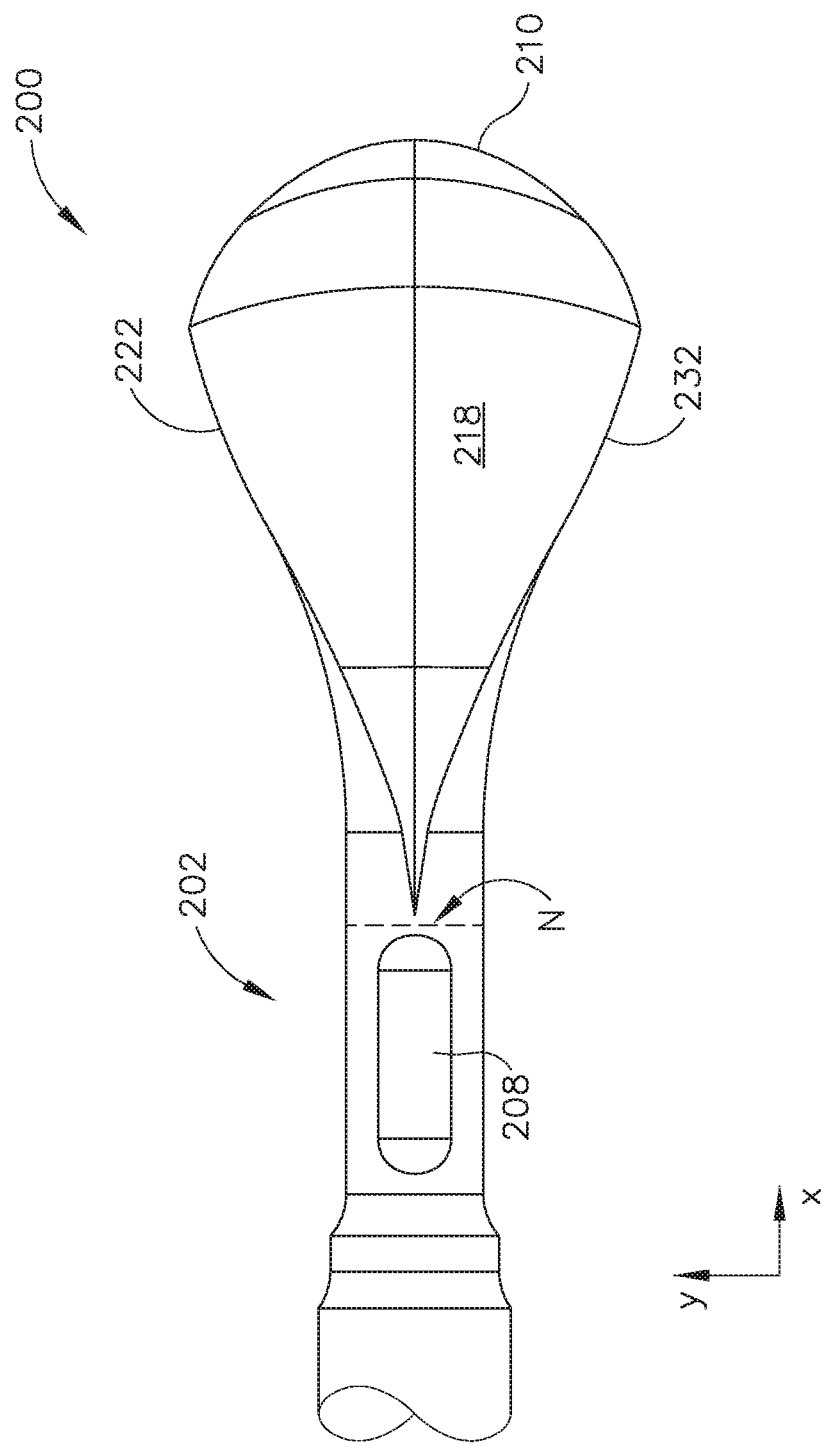
FIG. 9 depicts a bottom plan view of the blade of FIG. 4.

Blade (200) of this example comprises a distally located and laterally presented first face (212). First face (212) is partially bound by a curved distal edge (210) and a curved proximal edge (214). FIGS. 8-9 show the curvature of edges (210, 214) along an x-y plane. In some versions, edges (210, 214) have the same radius of curvature along the x-y plane. In the present example, however, edges (210, 214) have different radii of curvature along the x-y plane. By way of example only, the radius of curvature of edge (210) along the x-y plane is approximately 0.25 inches; while the radius of curvature of edge (210) along the x-y plane is approximately 0.35 inches. As another merely illustrative example, the curvature of edge (210) and/or edge (214) along the x-y plane may be the same as the curvature along the x-y plane in a distal edge of a conventional Cobb elevator instrument. Alternatively, any other suitable radius of curvature may be used along the x-y plane. It should also be understood that edges (210, 214) may have different respective radii of curvature along the x-y plane.

Figure 10:
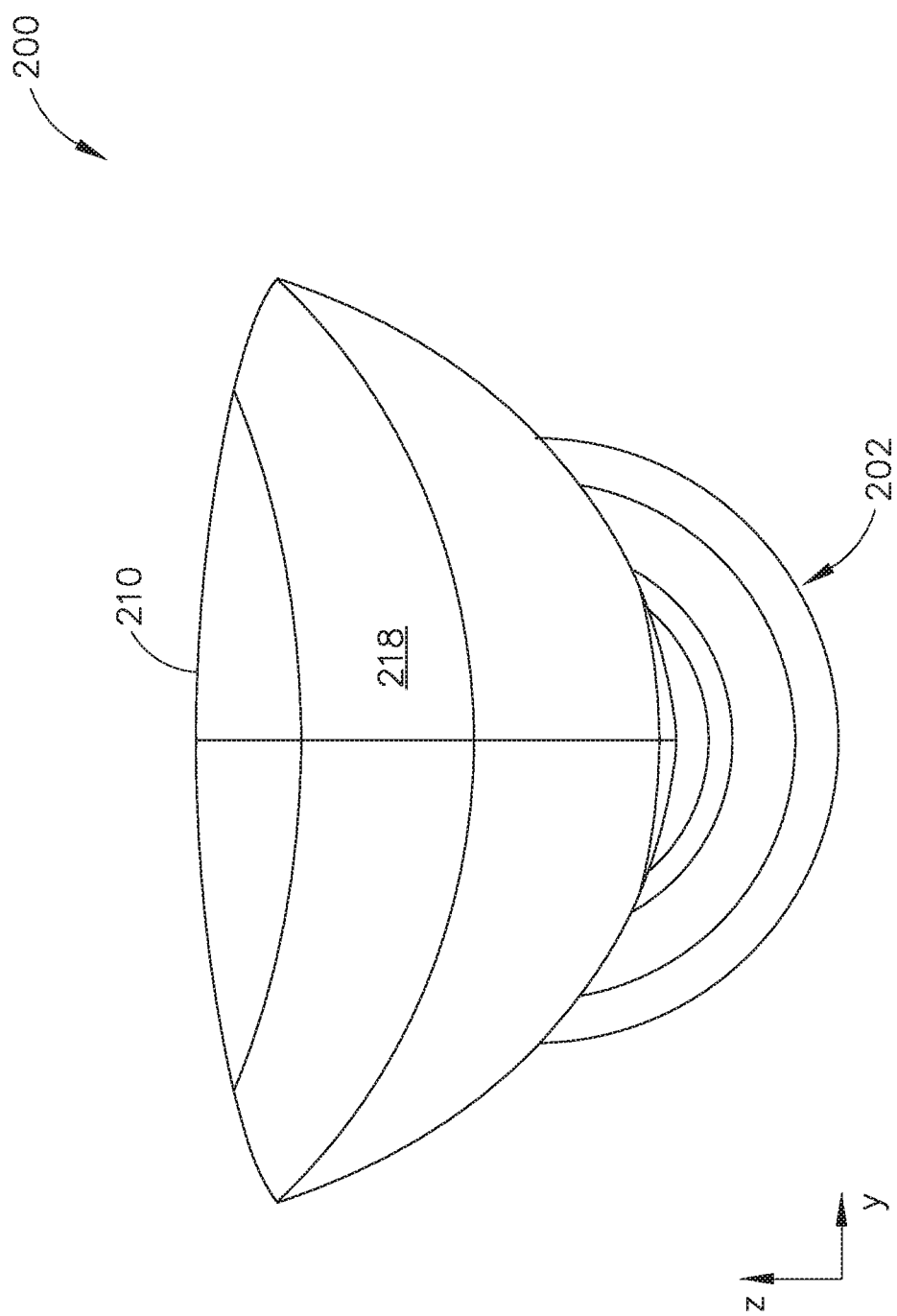
FIG. 10 depicts a front end view of the blade of FIG. 4.

FIG. 10 shows the curvature of distal edge (210) along a y-z plane. In some versions distal edge (210) may have a radius of curvature along the y-z plane between approximately 2.5 inches and approximately 3.0 inches. Proximal edge (214) and first face (210) may have the same radius of curvature along the y-z plane. Alternatively, any other suitable radius of curvature may be used along the y-z plane. It should also be understood that edges (210, 214) and first face (212) may instead be flat along the y-z plane.

Figure 11:
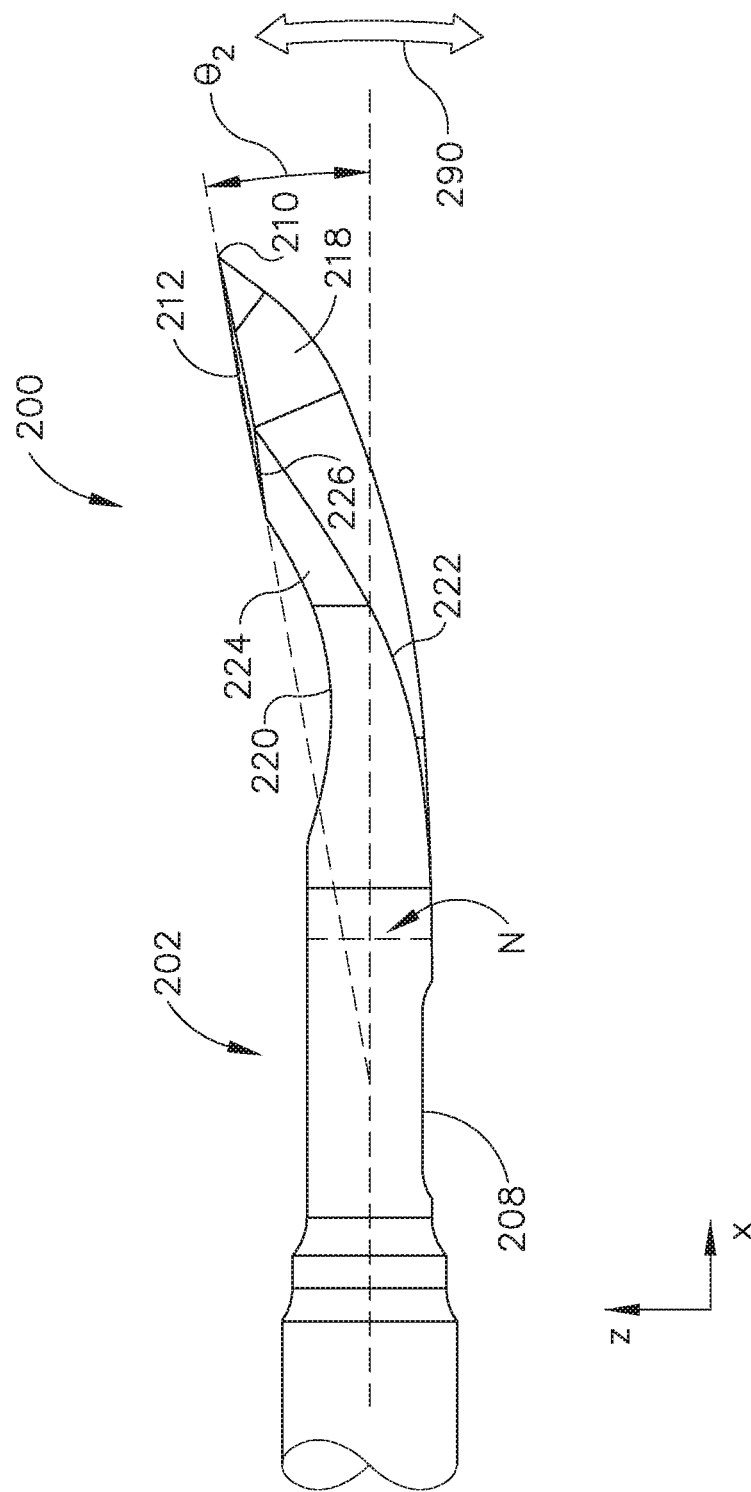
FIG. 11 depicts a side elevational view of the blade of FIG. 4.
Figure 12:
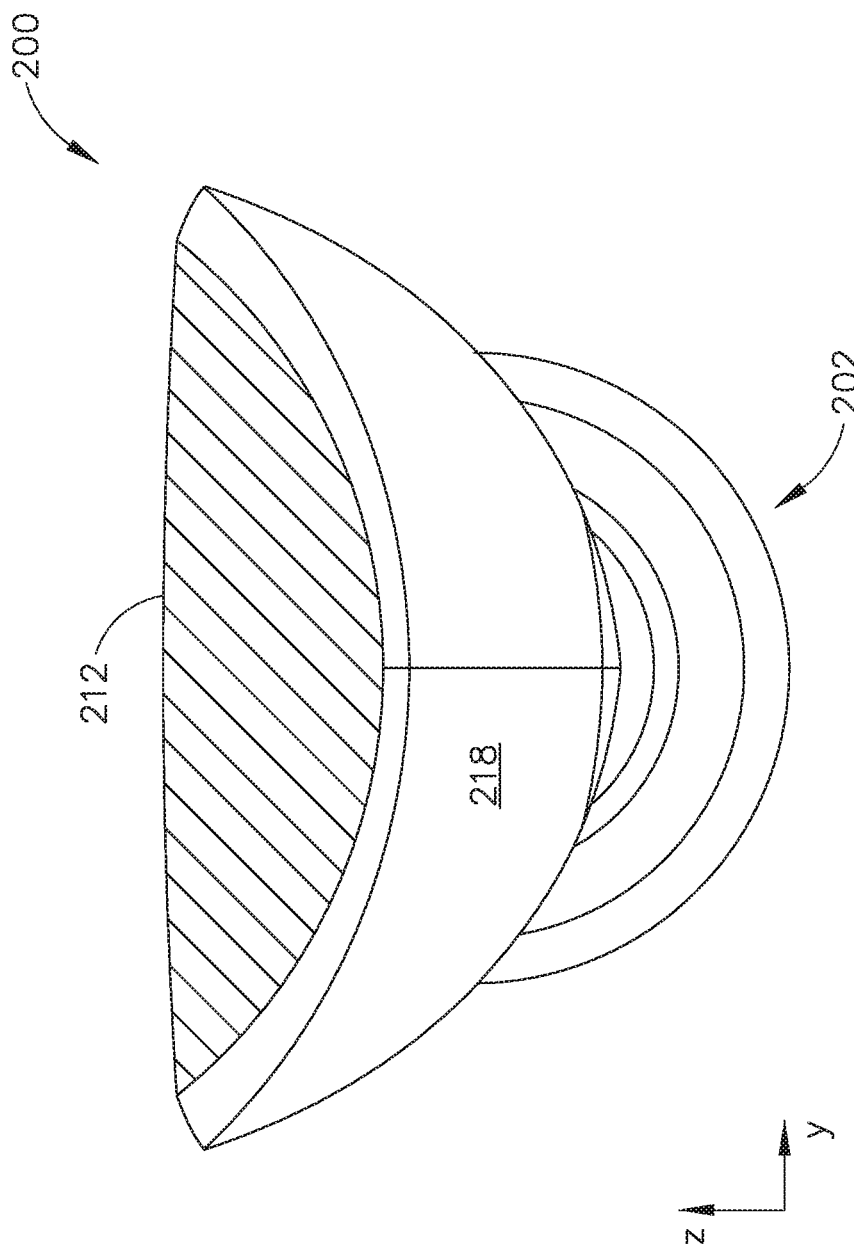
FIG. 12 depicts a cross-sectional view of the blade of FIG. 4, taken along line 12-12 of FIG. 8.

As best seen in FIG. 11, first face (212) defines an angle ($\theta_2$) with the longitudinal axis (LA) along the x-z plane. By way of example only, angle ($\theta_2$) may be approximately 9.2 degrees; or anywhere between approximately 0 degrees and approximately 10 degrees, or any other suitable value. As another merely illustrative example, first face (212) may define an angle ($\theta_2$) with the longitudinal axis (LA) that is the same as the corresponding angle defined by a corresponding face of a conventional Cobb elevator instrument. Alternatively, any other suitable value may be used. It should also be understood that first face (212) need not necessarily be straight along the x-z plane, such that first face (212) generally extends along angle ($\theta_2$). For instance, the center of each edge (210, 214) may be located along a respective line that defines angle ($\theta_2$) with the longitudinal axis (LA), while an intermediate portion of first face (212) bows outwardly in a convex configuration or inwardly in a concave configuration. As best seen in FIG. 12, first face (212) may also provide a convex configuration or a concave configuration along the y-z plane. Alternatively, first face (212) may be flat along the y-z plane.

In the present example, distal edge (210) is used to scrape tissue (e.g., muscle, tendon, ligament, periostium, etc.) from bone, and the radius of curvature of distal edge (210) is configured to prevent blade (200) from gouging bone while blade (200) performs such scraping. Such scraping may include movement of blade (200) along the longitudinal axis (LA) defined by waveguide (202), in the y direction, in the z direction, in an angular movement (arrow (290) in FIG. 11) about a pitch axis passing through the longitudinal axis (LA), and/or in an angular movement (arrow (292) in FIG. 8) about a yaw axis passing through the longitudinal axis (LA). The pitch and/or yaw axes may be located at a position along the longitudinal axis (LA) where the operator is gripping the instrument. Other suitable scraping motions will be apparent to those of ordinary skill in the art in view of the teachings herein. In some instances, blade (200) is ultrasonically inactive during such scraping operations. In some other instances, blade (200) is activated during such scraping operations. It should also be understood that first face (212) may be used as a coagulation flat. In other words, when the operator encounters a bleeder in tissue at the surgical site, first face (212) may be pressed against the bleeder while blade (200) is activated. This may coagulate or seal the bleeder/tissue.

Blade (200) of the present example also includes a pair of lateral edges (220, 230) extending proximally from edge (214) and another pair of lateral edges (222, 232) extending proximally from edge (210). As best seen in FIG. 8, edges (222, 232) are symmetric about the longitudinal axis (LA) of waveguide (202). In particular, edges (222, 232) each define the same angle ($\theta_1$) with the longitudinal axis (LA) along the x-y plane and are oriented such that the distance between edges (222, 232) increases along the length of blade (200) in the x direction. By way of example only, angle ($\theta_1$) may be between approximately 5 degrees and approximately 25 degrees. Alternatively, any other suitable value may be used. It should also be understood that edges (222, 232) need not necessarily be straight, such that edges (222, 232) generally extend along angle ($\theta_1$). For instance, the distal and proximal end of each edge (222, 232) may be located along a respective line that defines angle ($\theta_1$) with the longitudinal axis (LA), while an intermediate portion of each edge (222, 232) bows outwardly in a convex configuration or inwardly in a concave configuration.

As best seen in FIG. 11, edge (220) is curved along the x-z plane. It should be understood that edge (230) may be similarly curved. By way of example only, edges (220, 230) may each have a radius of curvature along the x-z plane between approximately 0.4 inches and approximately 0.6 inches. Alternatively, any other suitable radius of curvature may be used along the x-z plane. It should also be understood that edges (220, 230) may have different respective radii of curvature along the x-z plane. As also seen in FIG. 11, edge (222) is also curved along the x-z plane. It should be understood that edge (232) may be similarly curved. By way of example only, edges (222, 232) may each have a radius of curvature along the x-z plane between approximately 0.5 inches and approximately 1.0 inches. Alternatively, any other suitable radius of curvature may be used along the x-z plane. It should also be understood that edges (222, 232) may have different respective radii of curvature along the x-z plane. As also seen in FIG. 11, the radius of curvature for edge (222) along the x-z plane is different from the radius of curvature of edge (220) along the x-z plane. In some other versions, edges (220, 222) may have the same radius of curvature along the x-z plane.

Figure 13:
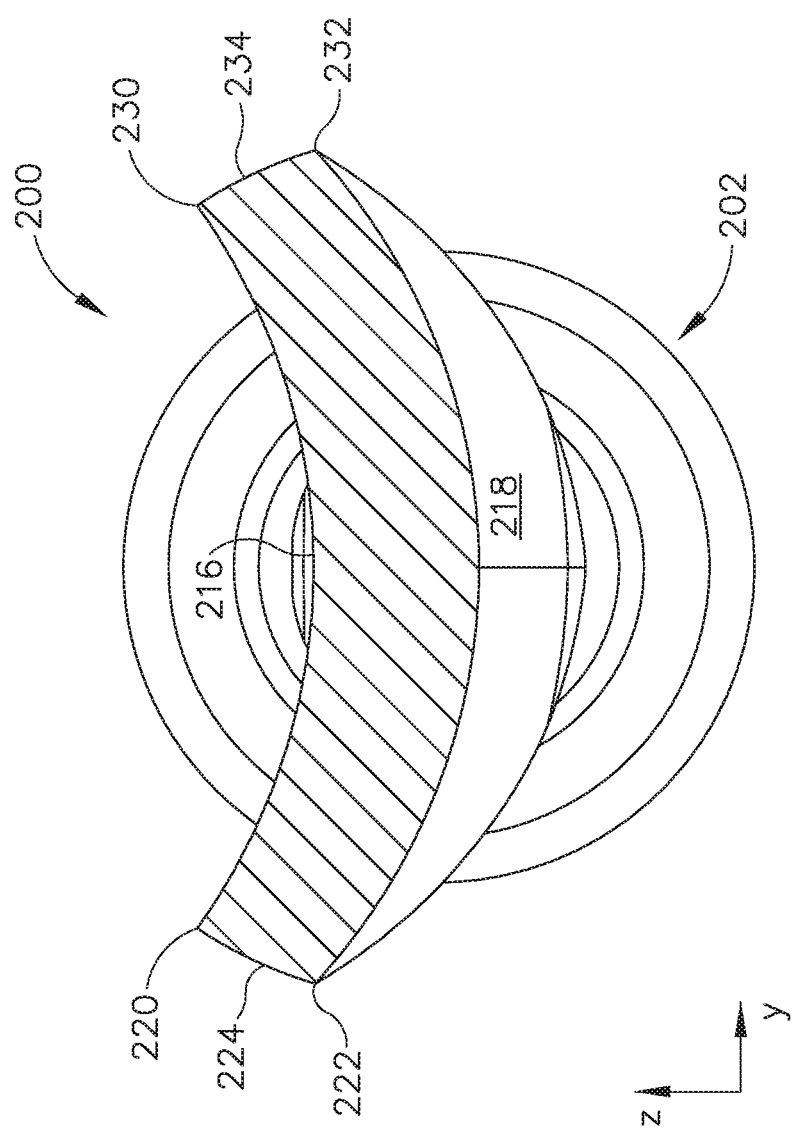
FIG. 13 depicts a cross-sectional view of the blade of FIG. 4, taken along line 13-13 of FIG. 8.

Edges (220, 222) partially bound a laterally presented second face (224); while edges (230, 232) partially bound a laterally presented third face (234). Faces (224, 234) are on opposite sides of blade (200) along the y axis. Faces (224, 234) are oriented obliquely and/or curved along the x-y plane (FIG. 8), along the x-z plane (FIG. 11), and along the y-z plane (FIG. 13). Second face (224) is distally bound by an edge (226), which extends from edge (210) to edge (214). Third face (234) is bound by an edge (236), which extends from edge (210) to edge (214). Edges (226, 236) further bound first face (212), such that first face (212) is fully bound by edges (210, 214, 226, 236). As best seen in FIG. 13, and by comparing FIG. 8 with FIG. 9, faces (224, 234) are oriented upwardly and outwardly. In some versions, faces (224, 234) are flat. In some other versions, faces (224, 234) are convex along the y-z plane. In still other versions, faces (224, 234) are concave along the y-z plane. As yet another merely illustrative alternative, faces (224, 234) may each have at least one region that is convex along the y-z plane and at least one region that is concave along the y-z plane; or some other combination of convex, concave, and/or flat regions.

It should be understood that edges (220, 230, 222, 232) may be used to perform side cutting of tissue with blade (200). For instance, with tissue positioned against any one or more of edges (220, 230, 222, 232), blade (200) may be moved along the y axis, along the z axis, in an angular movement (arrow (290) in FIG. 11) about a pitch axis passing through the longitudinal axis (LA), and/or in an angular movement (arrow (292) in FIG. 8) about a yaw axis passing through the longitudinal axis (LA). Other suitable side cutting motions will be apparent to those of ordinary skill in the art in view of the teachings herein. The pitch and/or yaw axes may be located at a position along the longitudinal axis (LA) where the operator is gripping the instrument. In some instances, blade (200) is ultrasonically inactive during such side cutting operations. In some other instances, blade (200) is activated during such side cutting operations.

Figure 14:
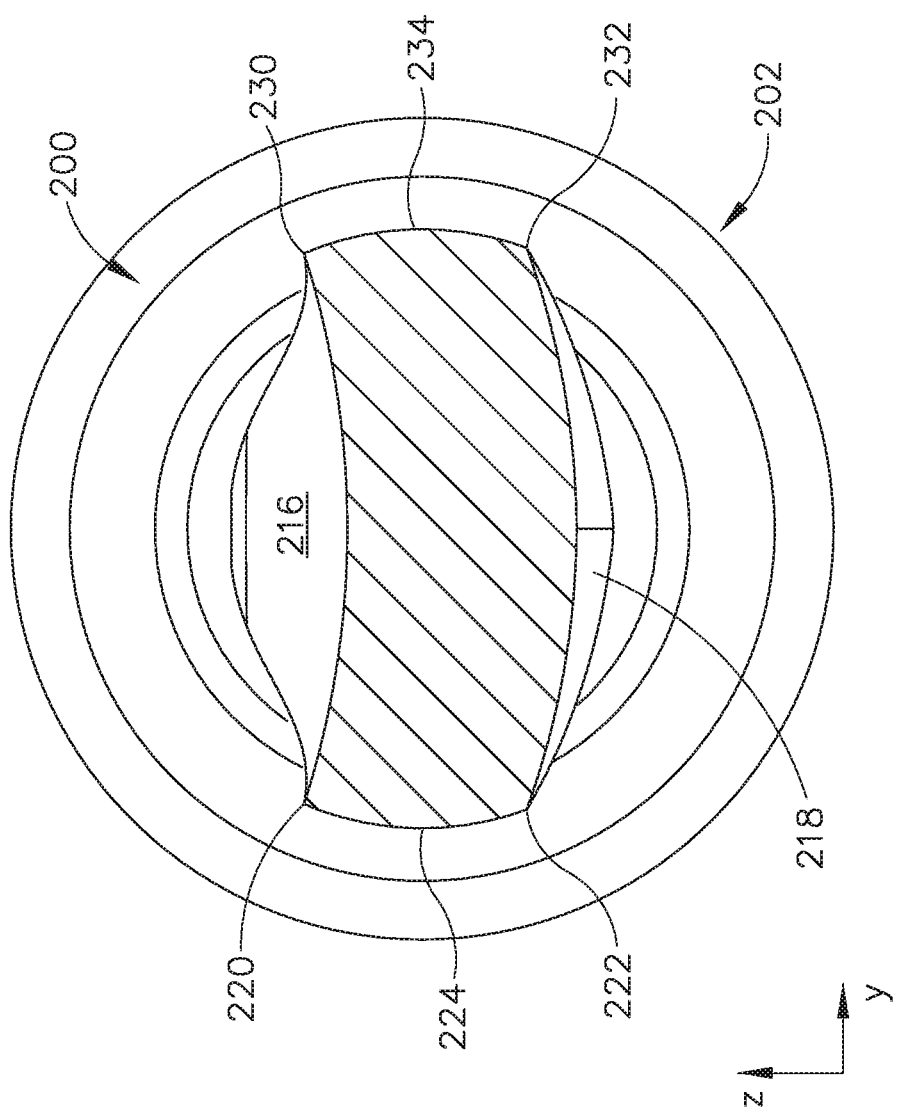
FIG. 14 depicts a cross-sectional view of the blade of FIG. 4, taken along line 14-14 of FIG. 8.
Figure 15:
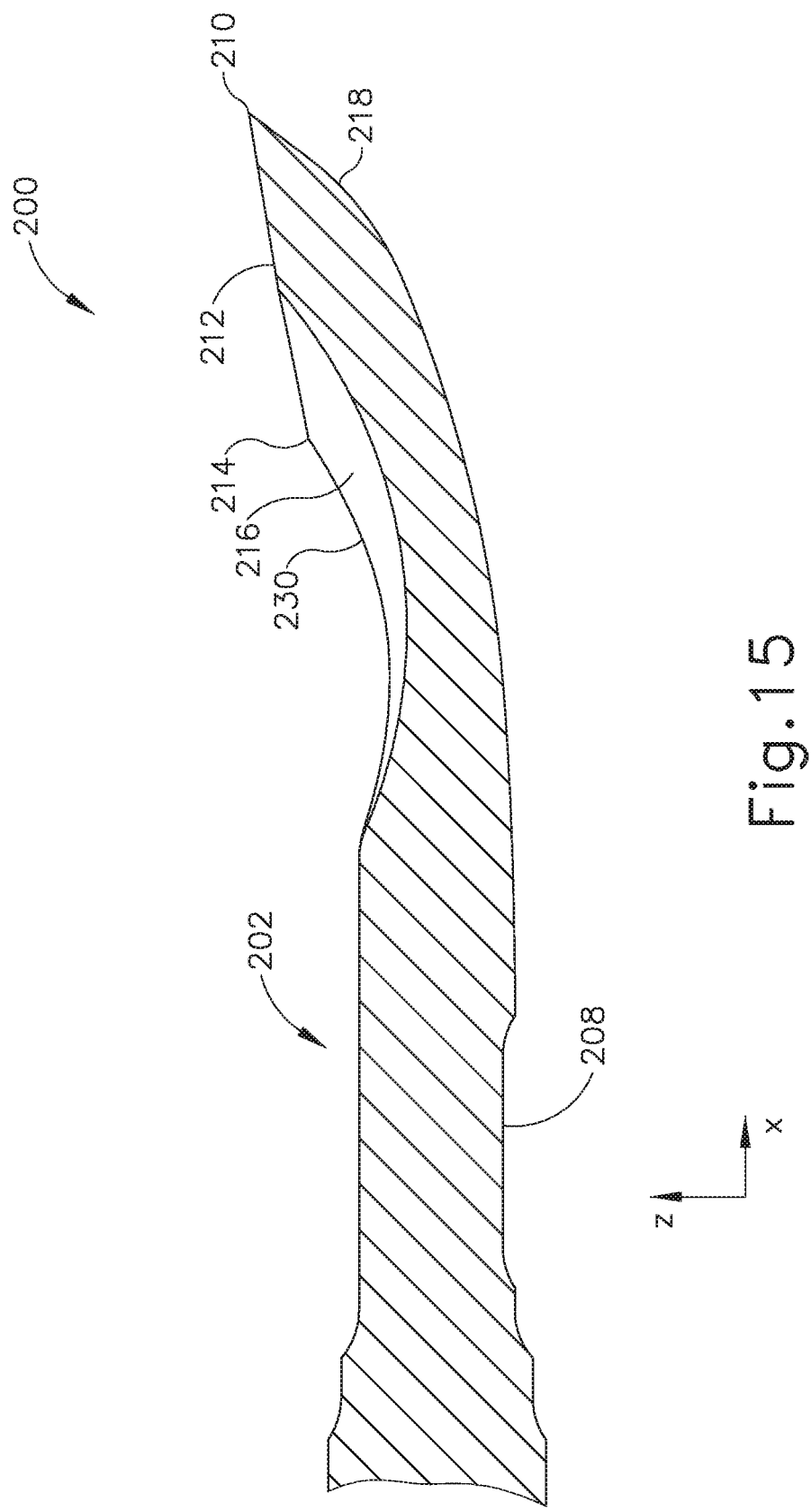
FIG. 15 depicts a cross-sectional view of the blade of FIG. 4, taken along line 15-15 of FIG. 8.

Blade (200) of the present example also includes a laterally presented, concave fourth face (216) and a laterally presented, convex fifth face (218). As best seen in FIGS. 13-15, faces (216, 218) are on opposite sides of blade (200) along the z axis. The concavity of fourth face (216) is configured to allow tissue to gather within the recess provided by fourth face (216) as the tissue is scraped from bone by distal edge (210). Fifth face (218) is configured to provide a blunt camming surface to promote blunt dissection with blade (200). It should also be understood that fifth face (218) may be used to provide coagulation. In other words, when the operator encounters a bleeder in tissue at the surgical site, fifth face (218) may be pressed against the bleeder while blade (200) is activated. This may coagulate or seal the bleeder/tissue.

In some versions, faces (216, 218) have the same radius of curvature along the x-z plane. By way of example only, the radius of curvature of faces (216, 218) along the x-z plane is between approximately 0.4 inches and approximately 0.6 inches. In some versions, the curvature of fourth face (216) and/or fifth face (218) along the x-z plane varies along the length of face (216, 218). By way of example only, the radius of curvature for fifth face (218) along the x-z plane may start at approximately 3.5 inches at the distal end of blade (200), then smoothly transition to a radius of curvature of approximately 1.25 inches, then smoothly transition to a radius of curvature of approximately 0.25 inches. As another merely illustrative example, fourth face (216) and/or fifth face (218) may have a curvature along the x-z plane that is the same as the curvature of a corresponding faces a conventional Cobb elevator instrument. Alternatively, any other suitable radius or radii of curvature may be used along the x-z plane. It should also be understood that faces (216, 218) may have different respective radii of curvature along the x-z plane.

Similarly, faces (216, 218) may have the same radius of curvature along the y-z plane. By way of example only, the radius of curvature of faces (216, 218) along the y-z plane is between approximately 0.4 inches and approximately 0.6 inches. In some versions, the curvature of fourth face (216) and/or fifth face (218) along the y-z plane varies along the width of face (216, 218). As another merely illustrative example, fourth face (216) and/or fifth face (218) may have a curvature along the y-z plane that is the same as the curvature of a corresponding faces a conventional Cobb elevator instrument. Alternatively, any other suitable radius or radii of curvature may be used along the y-z plane. It should also be understood that faces (216, 218) may have different respective radii of curvature along the y-z plane. In versions where first face (212) is curved along the y-z plane, the radius defining the curvature of first face (212) along the y-z plane may be greater than the radius defining the curvature of fourth face (216) along the y-z plane. Likewise, the radius defining the curvature of first face (212) along the y-z plane may be greater than the radius defining the curvature of fifth face (218) along the y-z plane.

Figure 16:
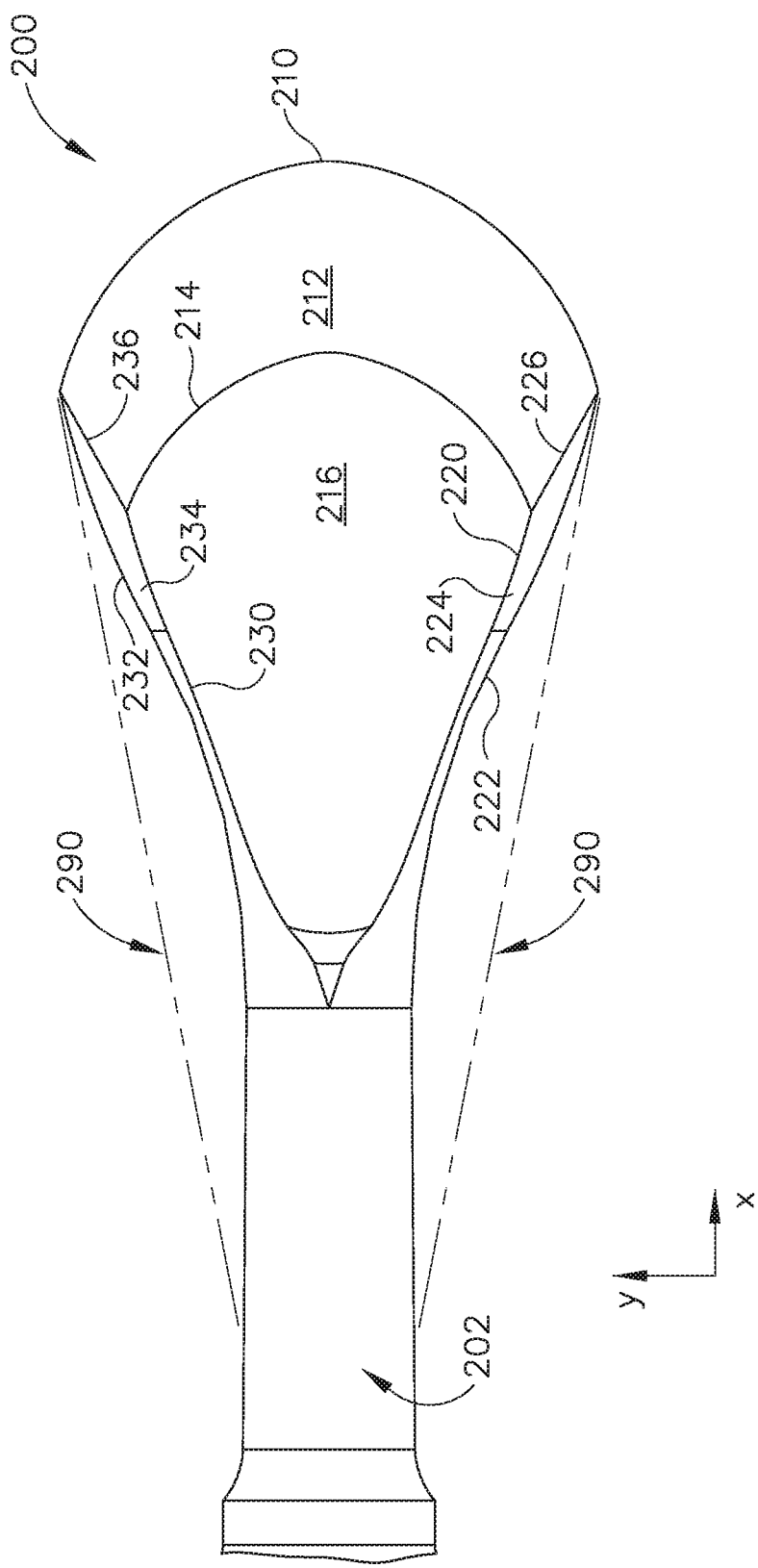
FIG. 16 depicts a top plan view of the blade of FIG. 4, with a Cobb elevator instrument blank profile shown in phantom.
Figure 17:
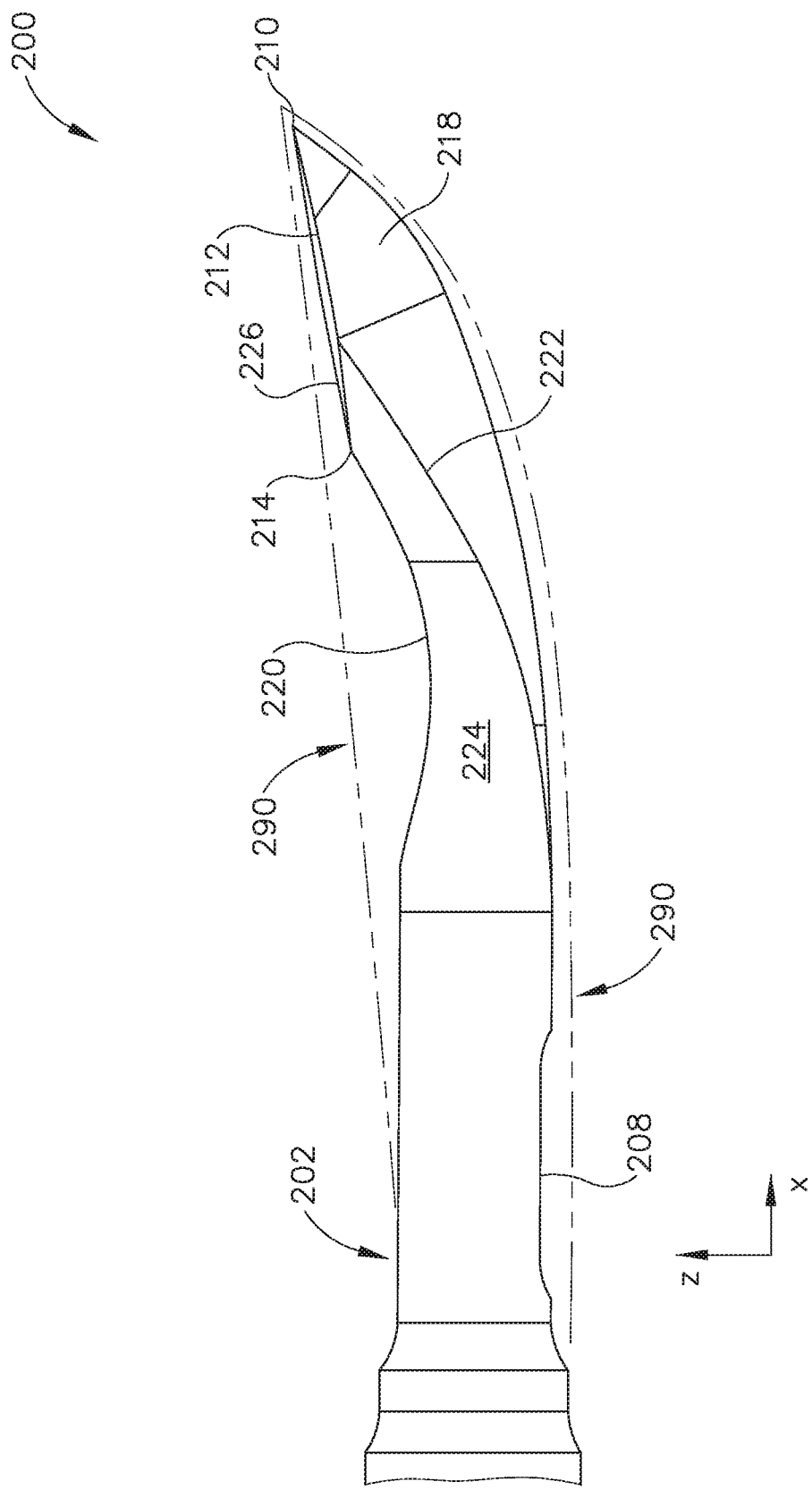
FIG. 17 depicts a side elevational view of the of FIG. 4, with a Cobb elevator instrument blank profile shown in phantom.
Figure 18:
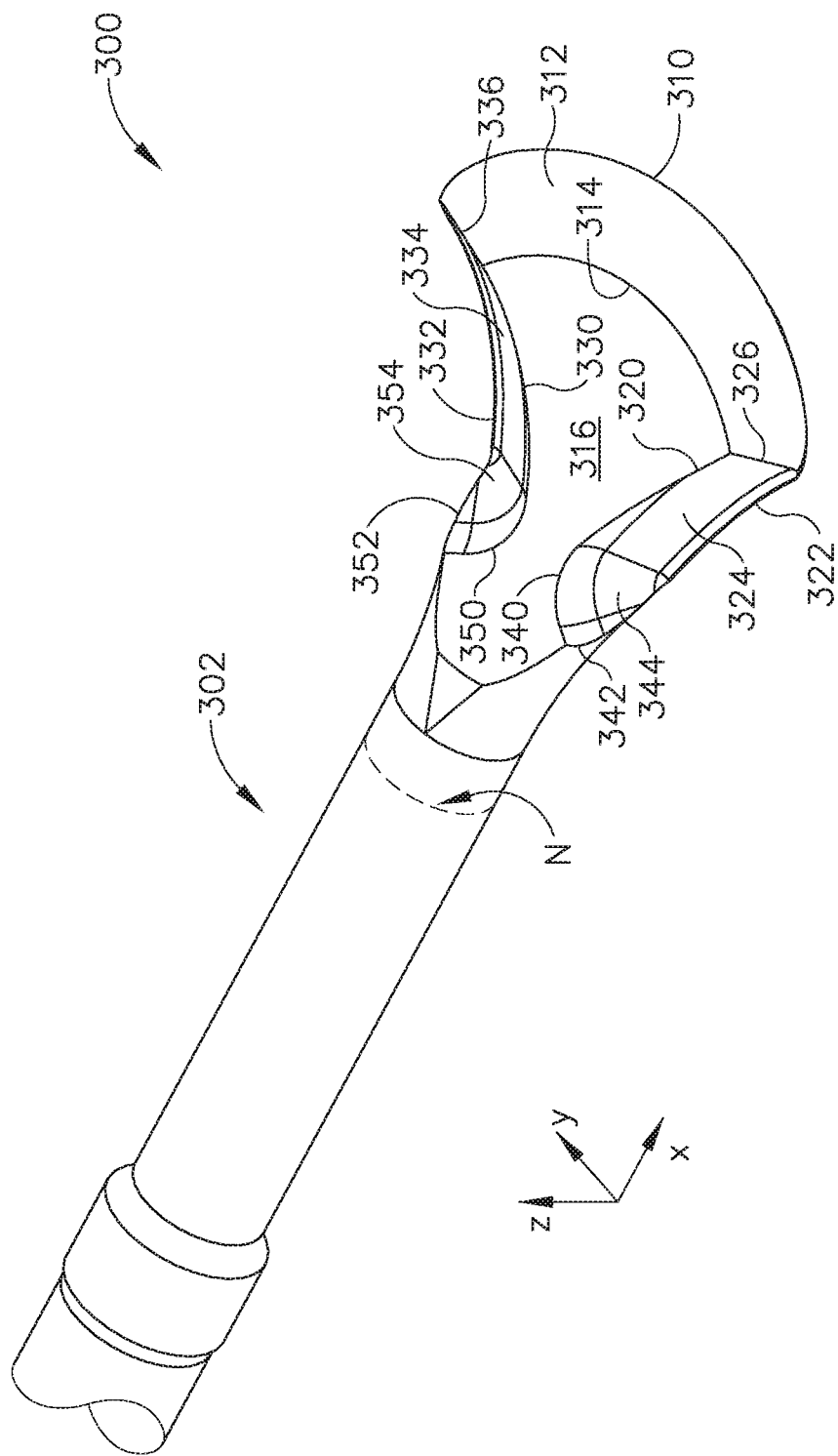
FIG. 18 depicts a top perspective view of another exemplary alternative ultrasonic blade suitable for incorporation in the instrument of FIG. 2.
Figure 19:
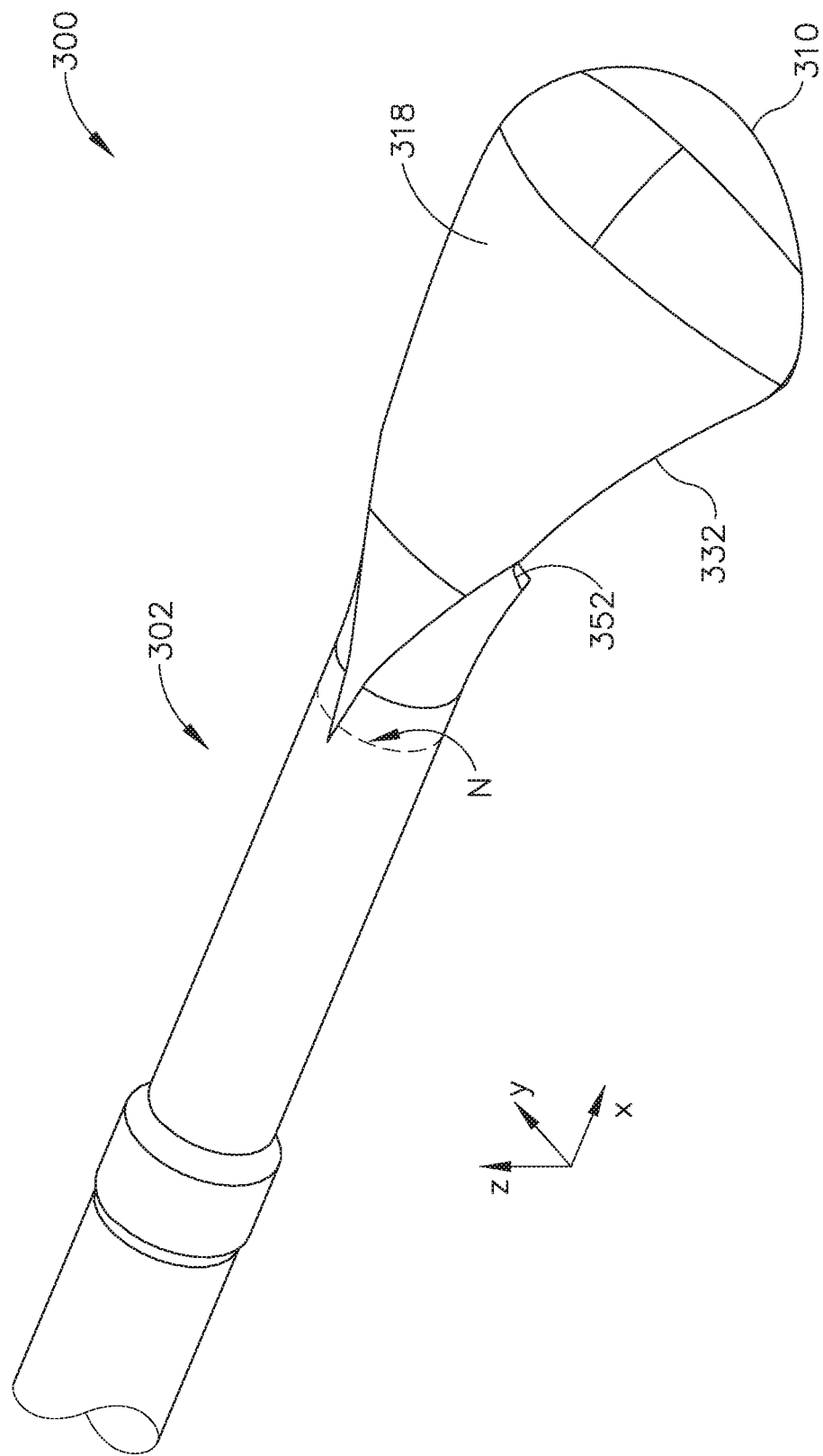
FIG. 19 depicts a bottom perspective view of the blade of FIG. 18.

FIGS. 16-17 show blade (200) of the present example in relation to a Cobb elevator blank (290), which is depicted in phantom lines. It should be understood that blade (200) may be formed by starting with a monolithic piece of metal that is configured in accordance with the Cobb elevator blank (290) and then removing material from that piece of metal until all of the shown and described features of blade (200) are formed. Such removal of material may be carried out in a milling process and/or using any other suitable kind of process(es). In some other versions, blade (200) is formed using a metal injection molded (MIM) process. Still other suitable ways in which blade (200) may be formed will be apparent to those of ordinary skill in the art in view of the teachings herein.

B. Exemplary Ultrasonic Blade with Cobb Tip and Proximal Recesses

FIGS. 18-27 show an exemplary alternative ultrasonic blade (300) and waveguide (302) that may be readily incorporated into instrument (20, 120). In particular, blade (300) and waveguide (302) may be mechanically and acoustically coupled with transducer (26, 126) in place of waveguide (28, 128) and blade (24, 132). In the present example, blade (300) and waveguide (302) are configured such that a distal-most node (N) is located just proximal to blade (300). It should be understood that the distal-most node (N) corresponds to a node associated with resonant ultrasonic vibrations communicated through waveguide (302) and blade (300). When blade (300) is activated with ultrasonic vibrations, the vibrational movement may be along the longitudinal axis (LA). In addition, the vibrational movement may be in an angular movement (arrow (390) in FIG. 23) along the x-z plane, about a pitch axis passing through the longitudinal axis (LA) at the distal-most node (N). Furthermore, the vibrational movement may be in an angular movement (arrow (392) in FIG. 20) along the x-y plane, about a yaw axis passing through the longitudinal axis (LA) at the distal-most node (N). It should therefore be understood that blade (300) may provide non-longitudinal modes of resonance. By way of example only, when blade (300) is activated to vibrate at an ultrasonic frequency, the ratio of lateral displacement of blade (300) from the longitudinal axis (LA) to the longitudinal displacement of blade (300) along the longitudinal axis (LA) is between approximately 0.60 to approximately 0.70. Alternatively, any other suitable ratio disclosed herein (among other ratios) may be used.

Figure 20:
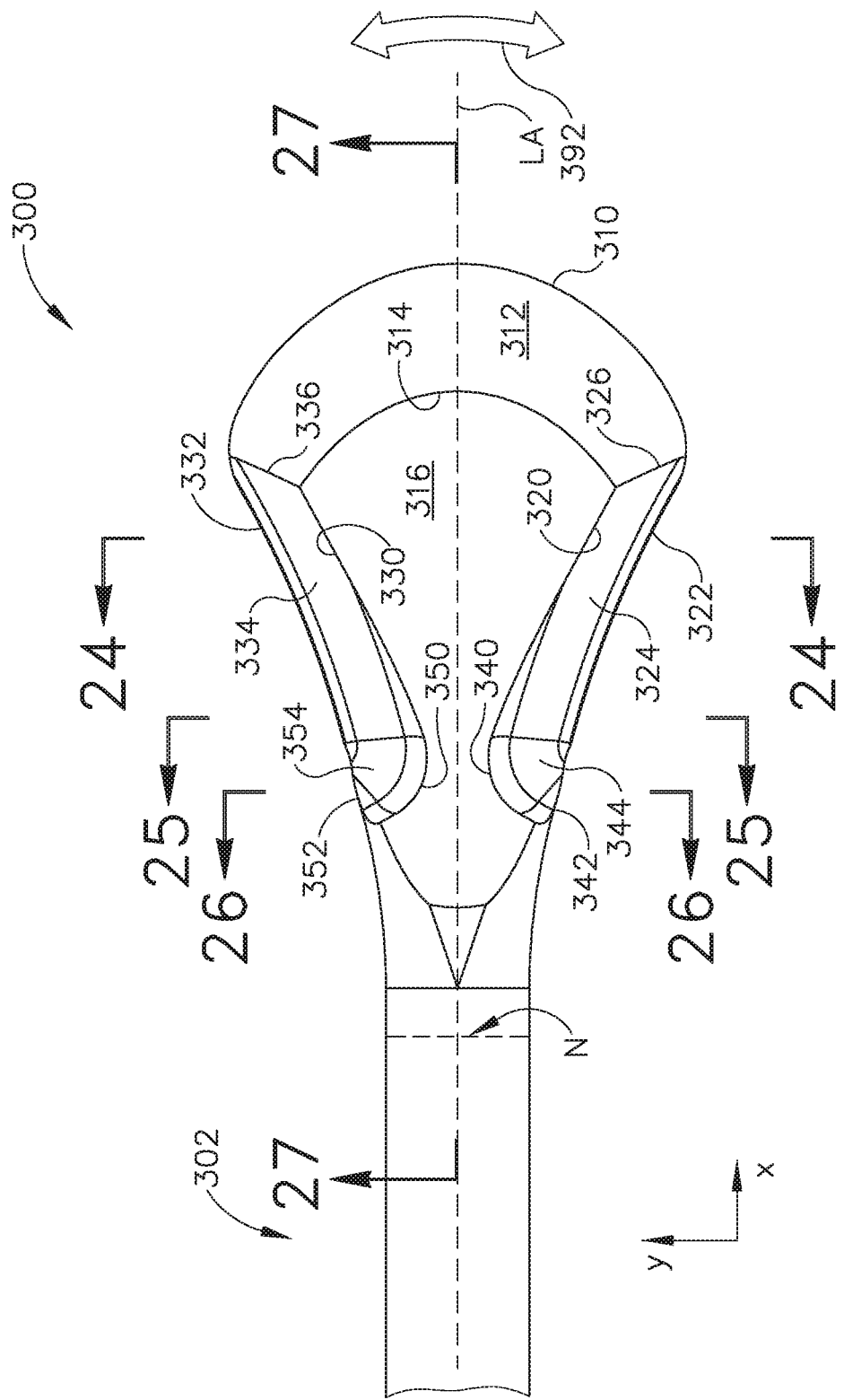
FIG. 20 depicts a top plan view of the blade of FIG. 18.
Figure 21:
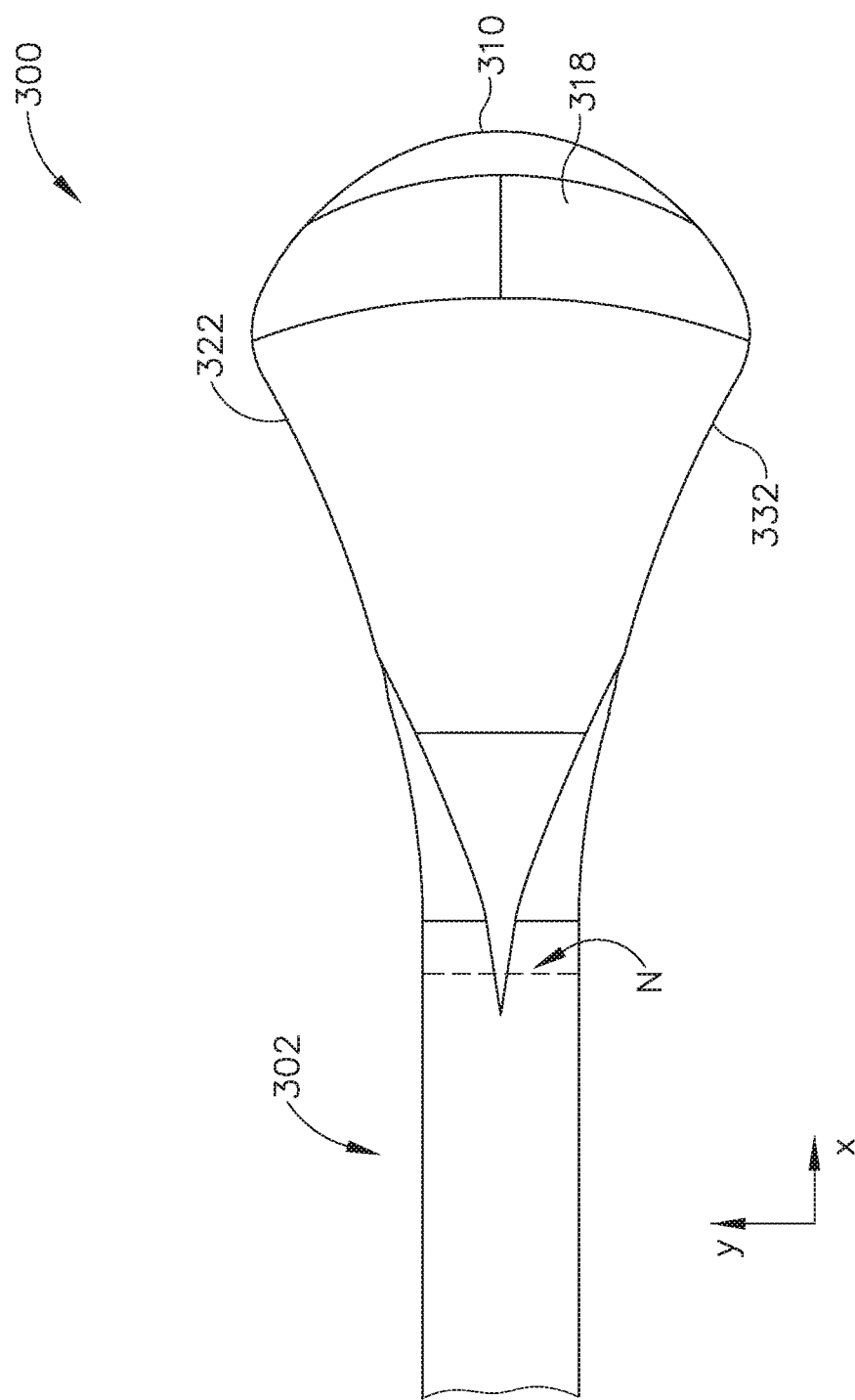
FIG. 21 depicts a bottom plan view of the blade of FIG. 18.

Blade (300) of this example comprises a distally located and laterally presented first face (312). First face (312) is partially bound by a curved distal edge (310) and a curved proximal edge (314). FIGS. 20-21 show the curvature of edges (310, 314) along an x-y plane. In some versions, edges (310, 314) have the same radius of curvature along the x-y plane. By way of example only, the radius of curvature of edges (310, 314) along the x-y plane is between approximately 025 inches and approximately 0.35 inches. As another merely illustrative example, the curvature of edges (310, 314) along the x-y plane may be the same as the curvature along the x-y plane in a distal edge of a conventional Cobb elevator instrument. Alternatively, any other suitable radius of curvature may be used along the x-y plane. It should also be understood that edges (310, 314) may have different respective radii of curvature along the x-y plane.

Figure 22:
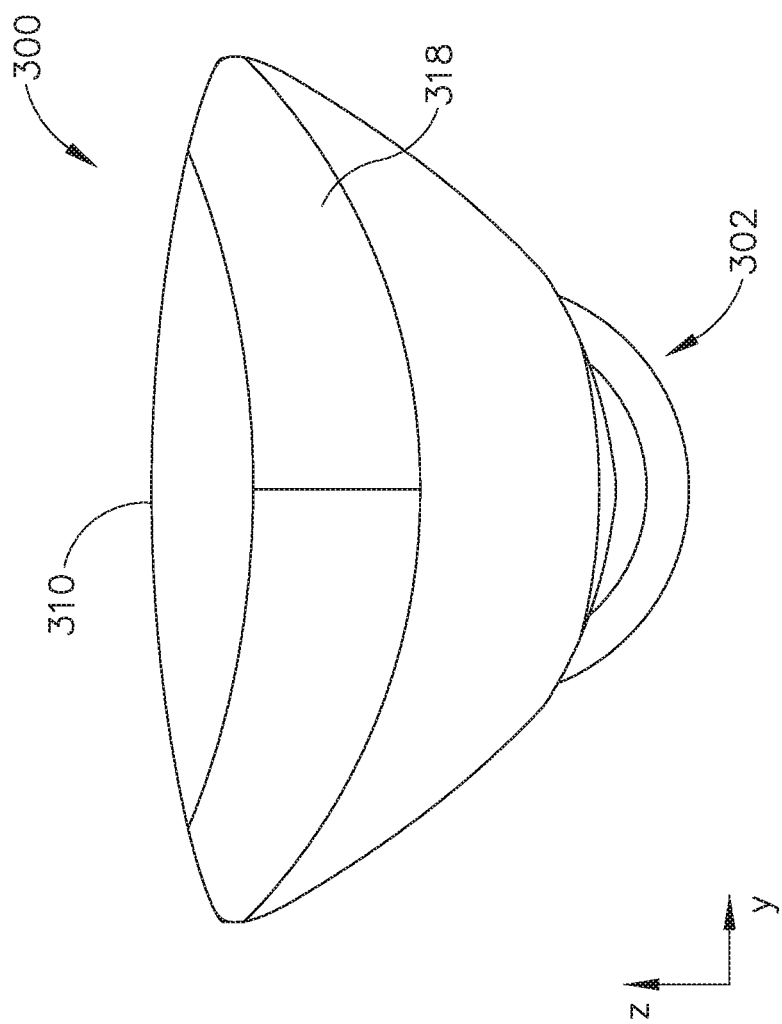
FIG. 22 depicts a front end view of the blade of FIG. 18.

FIG. 22 shows the curvature of distal edge (310) along a y-z plane. In some versions distal edge (310) may have a radius of curvature along the y-z plane between approximately 2.5 inches and approximately 3.5 inches. Proximal edge (314), distal edge (310), and/or first face (312) may have the same radius of curvature along the y-z plane. Alternatively, any other suitable radius of curvature may be used along the y-z plane. It should also be understood that edges (310, 314) and first face (312) may instead be flat along the y-z plane.

Figure 23:
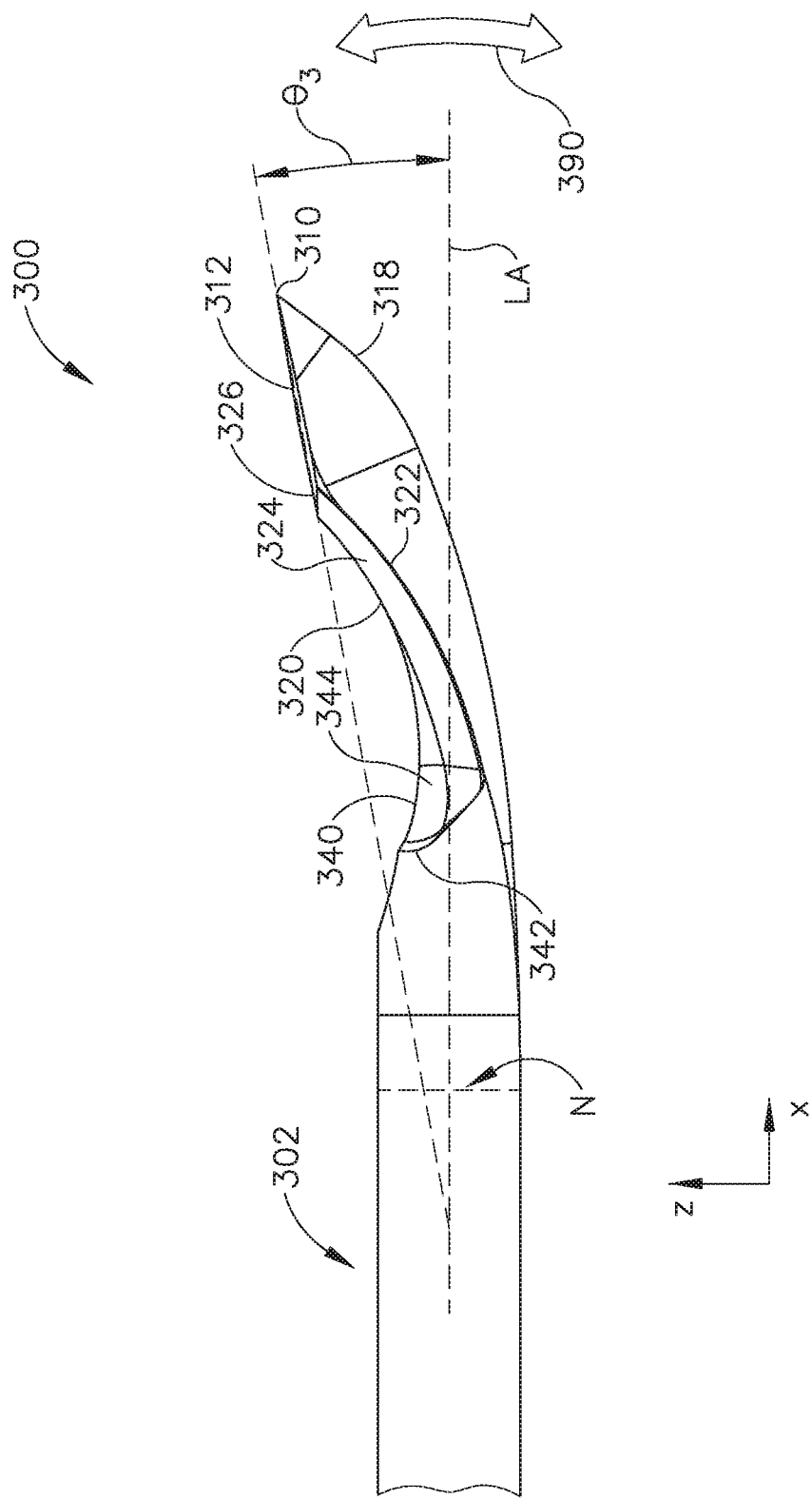
FIG. 23 depicts a side elevational view of the blade of FIG. 18.

As best seen in FIG. 23, first face (212) defines an angle ($\theta_3$) with the longitudinal axis (LA) along the x-z plane. By way of example only, angle ($\theta_3$) may be between approximately 0 degrees and approximately 10 degrees. As another merely illustrative example, first face (312) may define an angle ($\theta_3$) with the longitudinal axis (LA) that is the same as the corresponding angle defined by a corresponding face of a conventional Cobb elevator instrument. Alternatively, any other suitable value may be used. It should also be understood that first face (312) need not necessarily be straight along the x-z plane, such that first face (312) generally extends along angle ($\theta_3$). For instance, the center of each edge (310, 314) may be located along a respective line that defines angle ($\theta_3$) with the longitudinal axis (LA), while an intermediate portion of first face (312) bows outwardly in a convex configuration or inwardly in a concave configuration. First face (312) may also provide a convex configuration or a concave configuration along the y-z plane. Alternatively, first face (312) may be flat along the y-z plane.

In the present example, distal edge (310) is used to scrape tissue (e.g., muscle, tendon, ligament, periostium, etc.) from bone, and the radius of curvature of distal edge (310) is configured to prevent blade (300) from gouging bone while blade (300) performs such scraping. Such scraping may include movement of blade (300) along the longitudinal axis (LA) defined by waveguide (302), in the y direction, in the z direction, in an angular movement (arrow (390) in FIG. 23) about a pitch axis passing through the longitudinal axis (LA), and/or in an angular movement (arrow (392) in FIG. 20) about a yaw axis passing through the longitudinal axis (LA). The pitch and/or yaw axes may be located at a position along the longitudinal axis (LA) where the operator is gripping the instrument. Other suitable scraping motions will be apparent to those of ordinary skill in the art in view of the teachings herein. In some instances, blade (300) is ultrasonically inactive during such scraping operations. In some other instances, blade (300) is activated during such scraping operations. It should also be understood that first face (312) may be used as a coagulation flat. In other words, when the operator encounters a bleeder in tissue at the surgical site, first face (312) may be pressed against the bleeder while blade (300) is activated. This may coagulate or seal the bleeder/tissue.

Blade (300) of the present example also includes a pair of lateral edges (320, 330) extending proximally from edge (314) and another pair of lateral edges (322, 332) extending proximally from edge (310). As best seen in FIG. 20, edges (320, 330) are symmetric about the longitudinal axis (LA) of waveguide (302) in this example, in particular, edges (320, 330) each define concave curves and are oriented such that the distance between edges (320, 330) increases along the length of blade (300) in the x direction. By way of example only, the radius of curvature for each edge (320, 330) along the x-y plane may be between approximately 0.75 inches and approximately 1.25 inches. Alternatively, any other suitable curvature may be used. It should also be understood that edges (320, 330) need not necessarily be curved, such that edges (320, 330) may be substantially straight.

Figure 24:
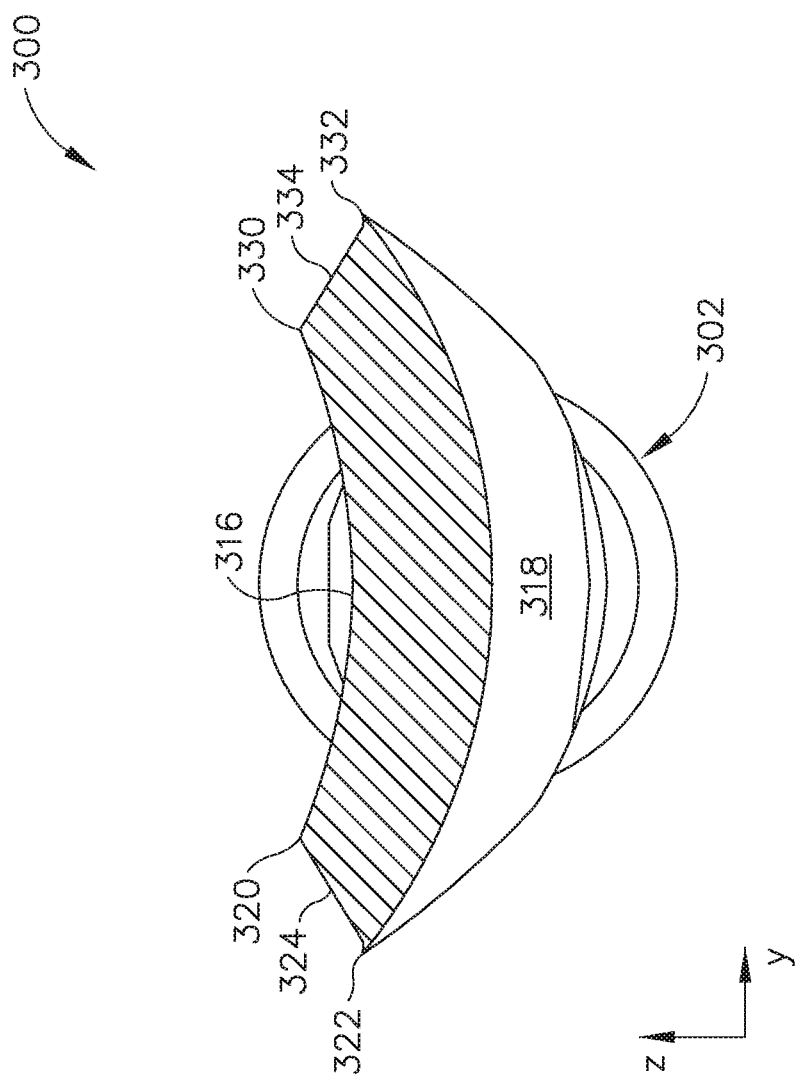
FIG. 24 depicts a cross-sectional view of the blade of FIG. 18, taken along line 24-24 of FIG. 20.
Figure 25:
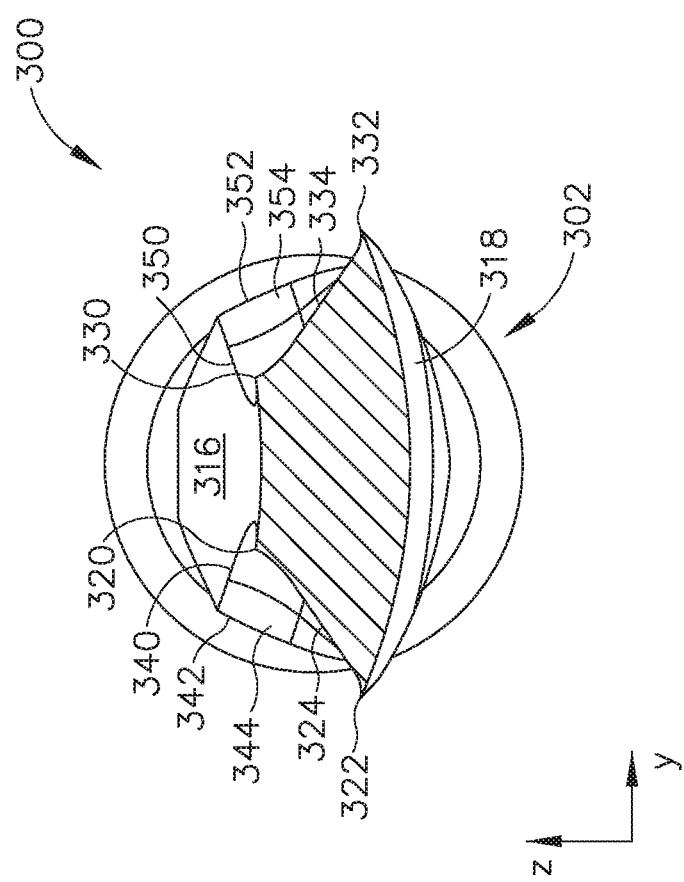
FIG. 25 depicts a cross-sectional view of the blade of FIG. 18, taken along line 25-25 of FIG. 20.
Figure 26:
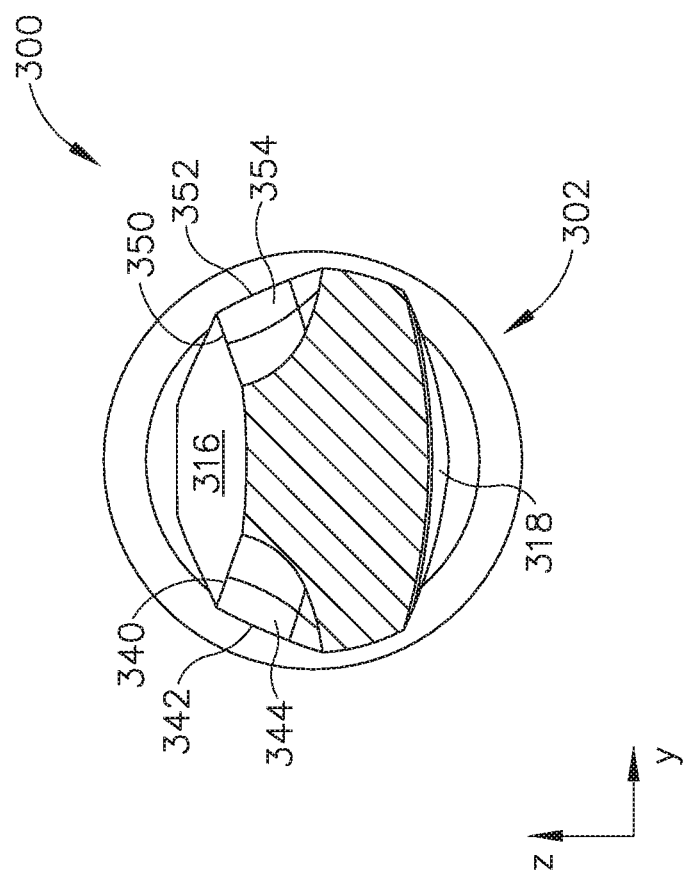
FIG. 26 depicts a cross-sectional view of the blade of FIG. 18, taken along line 26-26 of FIG. 20.
Figure 27:
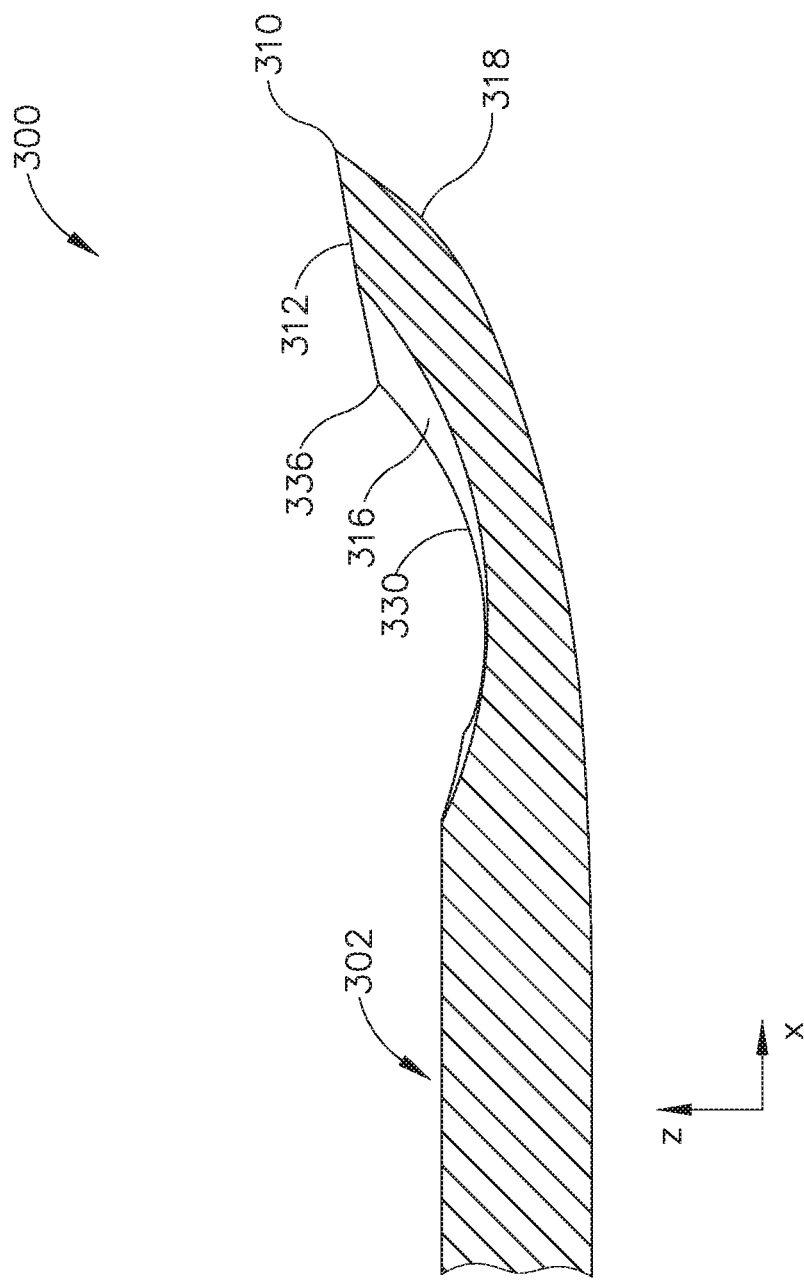
FIG. 27 depicts a cross-sectional view of the blade of FIG. 18, taken along line 27-27 of FIG. 20.
Figure 28:
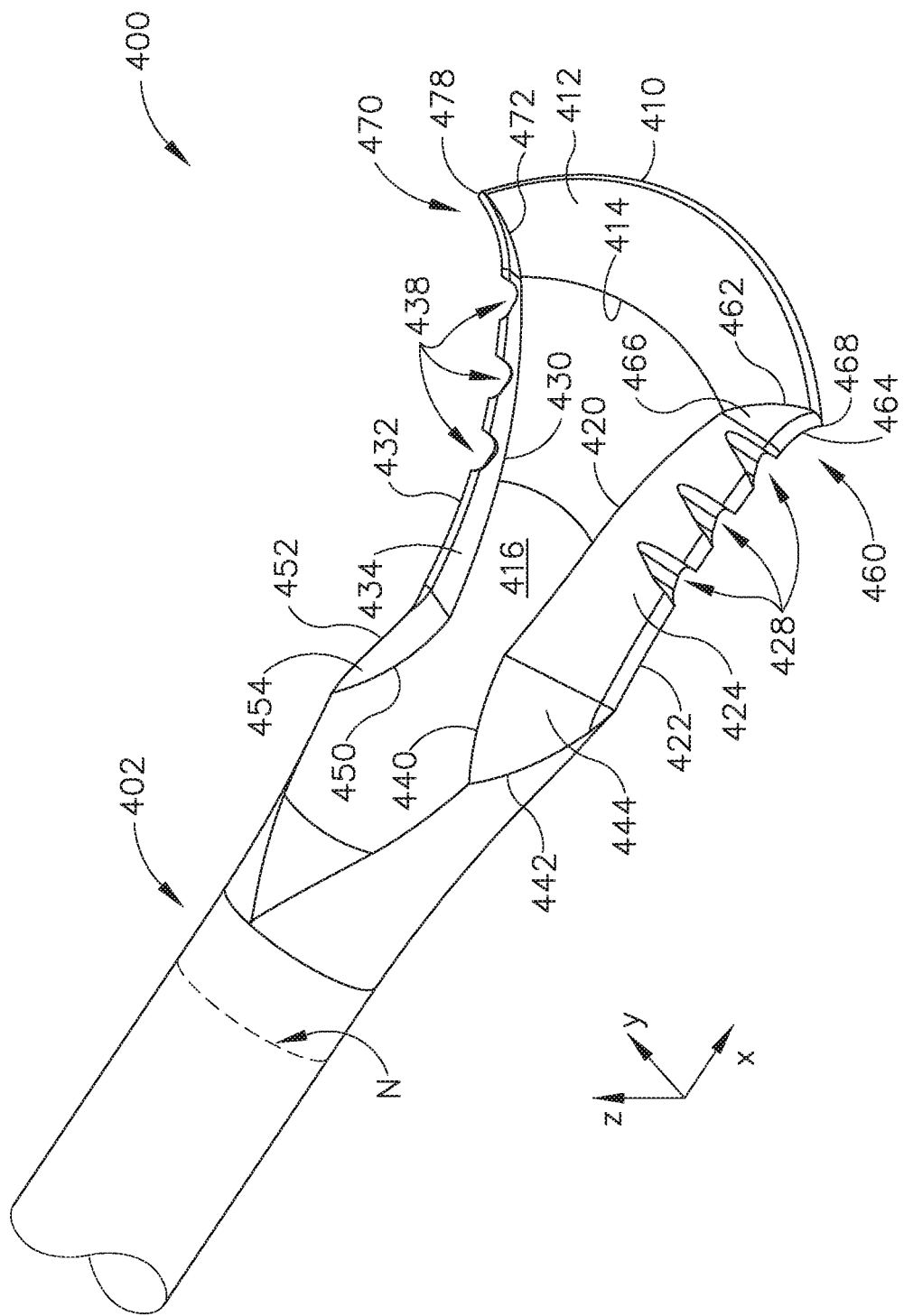
FIG. 28 depicts a top perspective view of another exemplary alternative ultrasonic blade suitable for incorporation in the instrument of FIG. 2.
Figure 29:
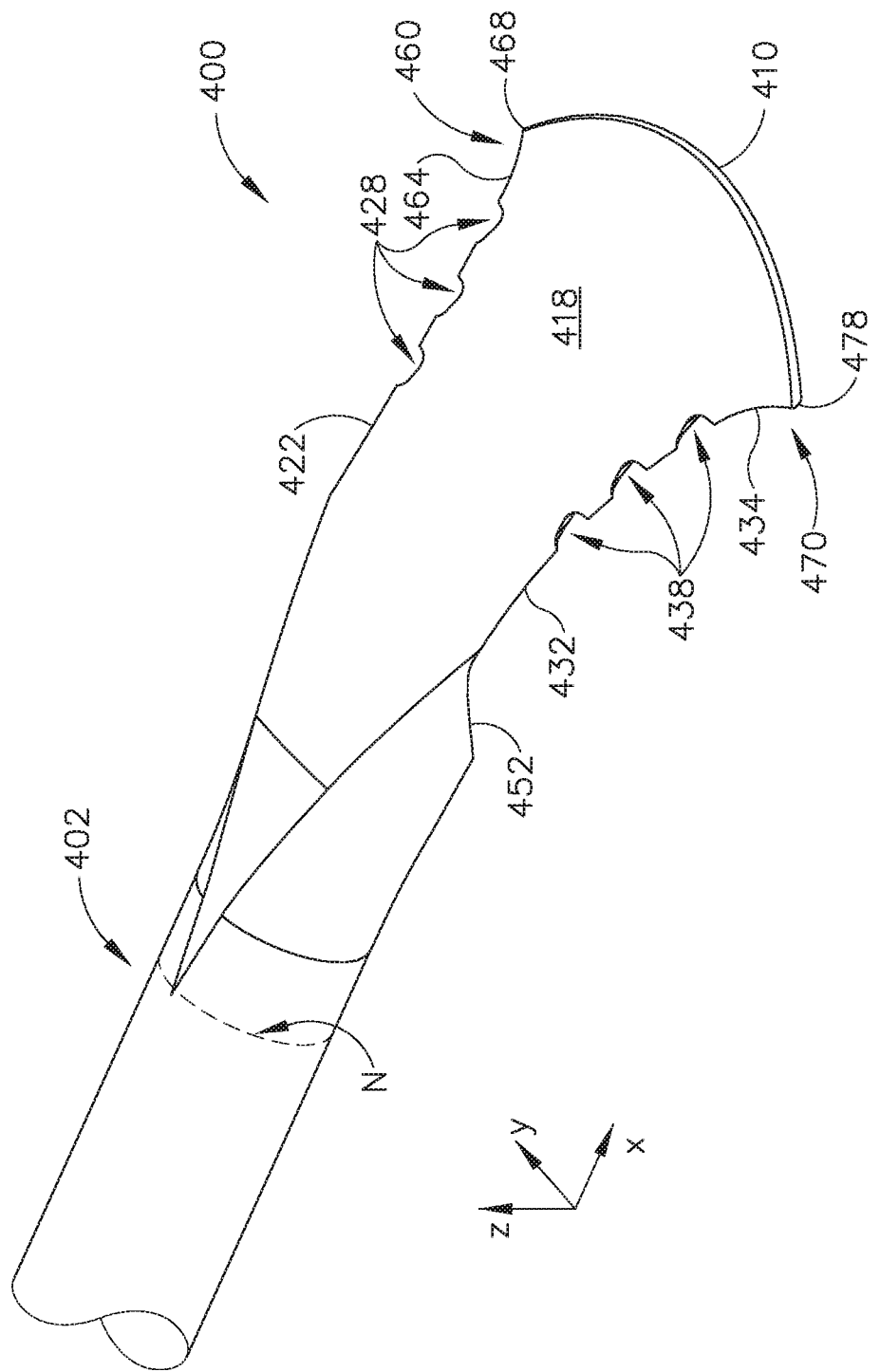
FIG. 29 depicts a bottom perspective view of the blade of FIG. 28.

Edges (322, 332) are also symmetric about the longitudinal axis (LA) of waveguide (302) in this example. In particular, edges (322, 332) each define concave curves and are oriented such that the distance between edges (322, 332) increases along the length of blade (300) in the x direction. By way of example only, the radius of curvature for each edge (322, 332) along the x-y plane may be between approximately 0.75 inches and approximately 1.25 inches. Alternatively, any other suitable curvature may be used. It should also be understood that edges (322, 332) need not necessarily be curved, such that edges (322, 332) may be substantially straight. As best seen in FIGS. 24-25, edges (322, 332) have a sharp configuration along at least part of their length. Such sharp configurations may assist in tissue dissection, such as in the side cutting motion referred to below.

As best seen in FIG. 23, edge (320) is curved along the x-z plane. It should be understood that edge (330) may be similarly curved. By way of example only, edges (320, 330) may each have a radius of curvature along the x-z plane between approximately 0.4 inches and approximately 0.6 inches. Alternatively, any other suitable radius of curvature may be used along the x-z plane. It should also be understood that edges (320, 330) may have different respective radii of curvature along the x-z plane. As also seen in FIG. 23, edge (322) is also curved along the x-z plane. It should be understood that edge (332) may be similarly curved. By way of example only, edges (322, 332) may each have a radius of curvature along the x-z plane between approximately 0.5 inches and approximately 1.0 inches. Alternatively, any other suitable radius of curvature may be used along the x-z plane. It should also be understood that edges (322, 332) may have different respective radii of curvature along the x-z plane. As also seen in FIG. 23, the radius of curvature for edge (322) along the x-z plane is different from the radius of curvature of edge (320) along the x-z plane. In some other versions, edges (320, 322) may have the same radius of curvature along the x-z plane.

Edges (320, 322) partially bound a laterally presented second face (324); while edges (330, 332) partially bound a laterally presented third face (334). Faces (324, 334) are on opposite sides of blade (300) along the y axis. Faces (324, 334) are oriented obliquely and/or curved along the x-y plane (FIG. 20), along the x-z plane (FIG. 23), and along the y-z plane (FIG. 24). Second face (324) is distally bound by an edge (326), which extends from edge (310) to edge (314). Third face (334) is bound by an edge (336), which extends from edge (310) to edge (314). Edges (326, 336) further bound first face (312), such that first face (312) is fully bound by edges (310, 314, 326, 336). As best seen in FIGS. 24-25, and by comparing FIG. 20 with FIG. 21, faces (324, 334) are oriented upwardly and outwardly. In some versions, faces (324, 334) are flat. In some other versions, faces (324, 334) are convex along the y-z plane. In still other versions, faces (324, 334) are concave along the y-z plane. As yet another merely illustrative alternative, faces (324, 334) may each have at least one region that is convex along the y-z plane and at least one region that is concave along the y-z plane; or some other combination of convex, concave, and/or flat regions.

As best seen in FIGS. 20, 23, and 25-26, blade (300) of this example further includes a proximal convex edge (340) and an adjacent proximal edge (342), which together partially bound a convex fourth face (344). Proximal convex edge (340) extends continuously from edge (320) described above. In some versions, edge (320) is substantially straight in the x-y plane while edge (340) is curved in the x-y plane. In versions where edge (320) has a radius of curvature along the x-y plane, edge (340) has a radius of curvature along the x-y plane that is less than the radius of curvature of edge (320) along the x-y plane. By way of example only, edge (340) may have a radius of curvature along the x-y plane of between approximately 0.03 inches and approximately 0.06 inches. Alternatively, any other suitable radius of curvature may be used along the x-y plane. Fourth face (344) extends continuously from second face (322). The combination of faces (322, 344) is thus fully bound by edges (320, 326, 322, 342, 340).

Similarly, blade (300) includes a proximal convex edge (350) and an adjacent proximal edge (352), which together partially bound a convex fifth face (354). Proximal convex edge (350) extends continuously from edge (330) described above. In some versions, edge (320) is substantially straight in the x-y plane while edge (350) is curved in the x-y plane. In versions where edge (330) has a radius of curvature along the x-y plane, edge (350) has a radius of curvature along the x-y plane that is less than the radius of curvature of edge (330) along the x-y plane. By way of example only, edge (350) may have a radius of curvature along the x-y plane of between approximately 0.03 inches and approximately 0.06 inches. Alternatively, any other suitable radius of curvature may be used along the x-y plane. Fourth face (354) extends continuously from second face (332). The combination of faces (332, 354) is thus fully bound by edges (330, 336, 332, 352, 350).

It should be understood that edges (320, 330, 322, 332, 340, 350) may be used to perform side cutting of tissue with blade (300). As one or more edges (320, 330, 322, 332, 340, 350) cut tissue, the corresponding face (344, 354) may assist in driving the tissue distally and outwardly away from blade (300). For or instance, with tissue positioned against any one or more of edges (320, 330, 322, 332, 340, 350), blade (300) may be moved along the y axis, along the z axis, in an angular movement (arrow (390) in FIG. 23) about a pitch axis passing through the longitudinal axis (LA), and/or in an angular movement (arrow (392) in FIG. 20) about a yaw axis passing through the longitudinal axis (LA). Other suitable side cutting motions will be apparent to those of ordinary skill in the art in view of the teachings herein. The pitch and/or yaw axes may be located at a position along the longitudinal axis (LA) where the operator is gripping the instrument. In some instances, blade (300) is ultrasonically inactive during such side cutting operations. In some other instances, blade (300) is activated during such side cutting operations.

Blade (300) of the present example also includes a laterally presented, concave sixth face (316) and a laterally presented, convex seventh face (318). As best seen in FIGS. 24-27, faces (316, 318) are on opposite sides of blade (300) along the z axis. The concavity of sixth face (316) is configured to allow tissue to gather within the recess provided by sixth face (316) as the tissue is scraped from bone by distal edge (310). Seventh face (318) is configured to provide a blunt camming surface to promote blunt dissection with blade (300). It should also be understood that seventh face (318) may be used to provide coagulation. In other words, when the operator encounters a bleeder in tissue at the surgical site, seventh face (318) may be pressed against the bleeder while blade (300) is activated. This may coagulate or seal the bleeder/tissue.

In some versions, faces (316, 318) have the same radius of curvature along the x-z plane. By way of example only, the radius of curvature of faces (316, 318) along the x-z plane is between approximately 1.0 inches and approximately 1.5 inches. In some versions, the curvature of sixth face (316) and/or seventh face (318) along the x-z plane varies along the length of face (316, 318). As another merely illustrative example, sixth face (316) and/or seventh face (318) may have a curvature along the x-z plane that is the same as the curvature of a corresponding faces a conventional Cobb elevator instrument. Alternatively, any other suitable radius or radii of curvature may be used along the x-z plane. It should also be understood that faces (316, 318) may have different respective radii of curvature along the x-z plane.

Similarly, faces (316, 318) may have the same radius of curvature along the y-z plane. Alternatively, in the present example faces (316, 318) have different radii of curvature. By way of example only, the radius of curvature of face (316) along the y-z plane is between approximately 0.5 inches and approximately 0.6 inches; while the radius of curvature of face (318) along the y-z plane is between approximately 0.25 inches and approximately 0.45 inches. In some versions, the curvature of sixth face (316) and/or seventh face (318) along the y-z plane varies along the width of face (316, 318). As another merely illustrative example, sixth face (316) and/or seventh face (318) may have a curvature along the y-z plane that is the same as the curvature of a corresponding faces a conventional Cobb elevator instrument. Alternatively, any other suitable radius or radii of curvature may be used along the y-z plane. It should also be understood that faces (316, 318) may have different respective radii of curvature along the y-z plane.

C. Exemplary Ultrasonic Blade with Cobb Tip and Lateral Serrations

FIGS. 28-37 show an exemplary alternative ultrasonic blade (400) and waveguide (402) that may be readily incorporated into instrument (20, 120). In particular, blade (400) and waveguide (402) may be mechanically and acoustically coupled with transducer (26, 126) in place of waveguide (28, 128) and blade (24, 132). In the present example, blade (400) and waveguide (402) are configured such that a distal-most node (N) is located just proximal to blade (400). It should be understood that the distal-most node (N) corresponds to a node associated with resonant ultrasonic vibrations communicated through waveguide (402) and blade (400). When blade (400) is activated with ultrasonic vibrations, the vibrational movement may be along the longitudinal axis (LA). In addition, the vibrational movement may be in an angular movement (arrow (490) in FIG. 33) along the x-z plane, about a pitch axis passing through the longitudinal axis (LA) at the distal-most node (N). Furthermore, the vibrational movement may be in an angular movement (arrow (492) in FIG. 30) along the x-y plane, about a yaw axis passing through the longitudinal axis (LA) at the distal-most node (N), it should therefore be understood that blade (400) may provide non-longitudinal modes of resonance. By way of example only, when blade (400) is activated to vibrate at an ultrasonic frequency, the ratio of lateral displacement of blade (400) from the longitudinal axis (LA) to the longitudinal displacement of blade (400) along the longitudinal axis (LA) is between approximately 0.70 to approximately 0.80. Alternatively, any other suitable ratio disclosed herein (among other ratios) may be used.

Figure 30:
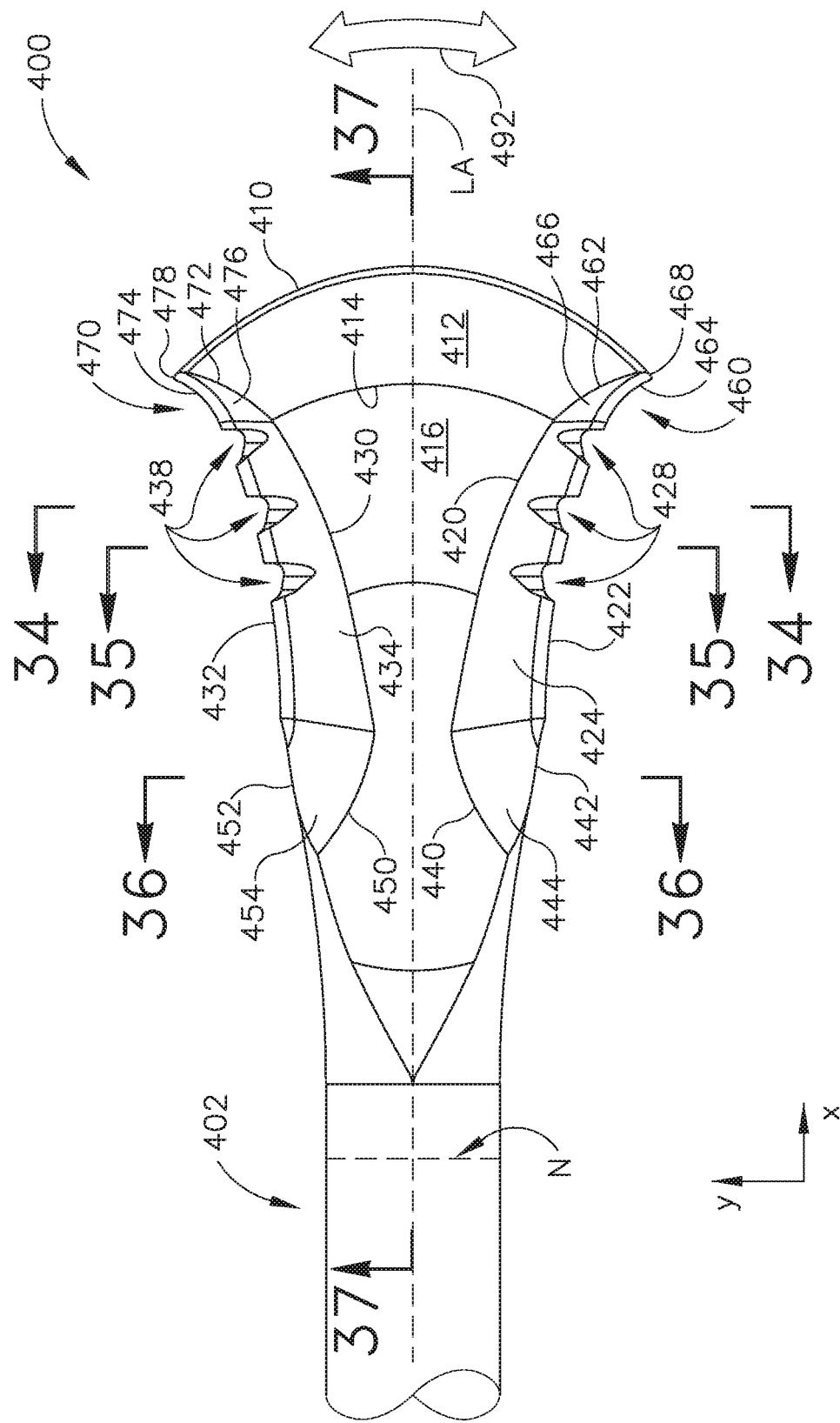
FIG. 30 depicts a top plan view of the blade of FIG. 28.
Figure 31:
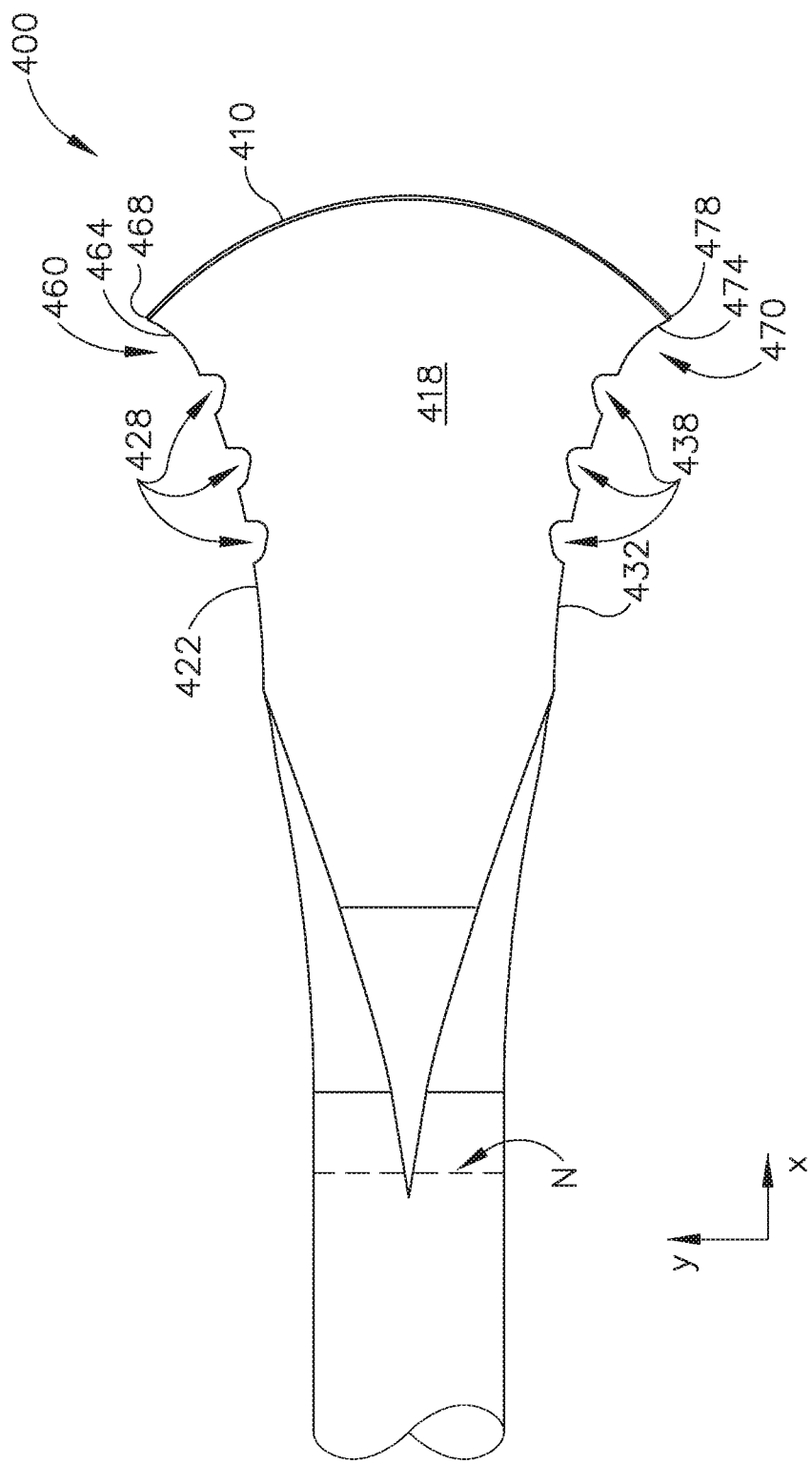
FIG. 31 depicts a bottom plan view of the blade of FIG. 28.

Blade (400) of this example comprises a distally located and laterally presented first face (412). First face (412) is partially bound by a curved distal edge (410) and a curved proximal edge (414). FIGS. 30-31 show the curvature of edges (410, 414) along an x-y plane. In some versions, edges (410, 414) have the same radius of curvature along the x-y plane. By way of example only, the radius of curvature of edges (410, 414) along the x-y plane is between approximately 0.20 inches and approximately 0.35 inches. As another merely illustrative example, the curvature of edges (410, 414) along the x-y plane may be the same as the curvature along the x-y plane in a distal edge of a conventional Cobb elevator instrument. Alternatively, any other suitable radius of curvature may be used along the x-y plane. It should also be understood that edges (410, 414) may have different respective radii of curvature along the x-y plane.

Figure 32:
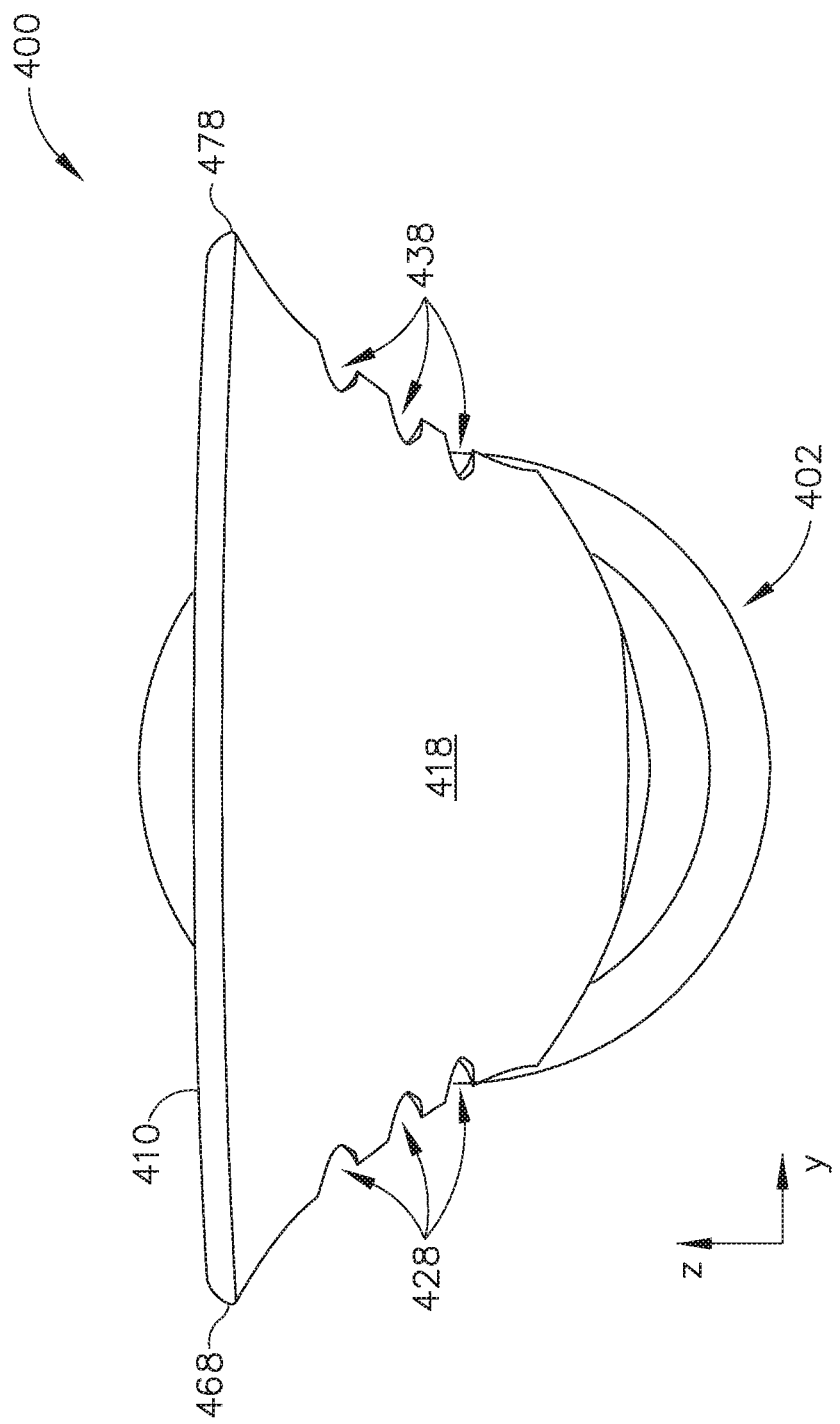
FIG. 32 depicts a front end view of the blade of FIG. 28.

FIG. 32 shows the profile of distal edge (410) along a y-z plane. In the present example, distal edge (410) is flat along the y-z plane. In some other versions distal edge (410) has a non-zero radius of curvature along the y-z plane. Proximal edge (414) and first face (410) may have the same radius of curvature along the y-z plane. Alternatively, any other suitable radius of curvature may be used along the y-z plane. It should also be understood that edges (410, 414) and first face (412) may be flat along the y-z plane.

Figure 33:
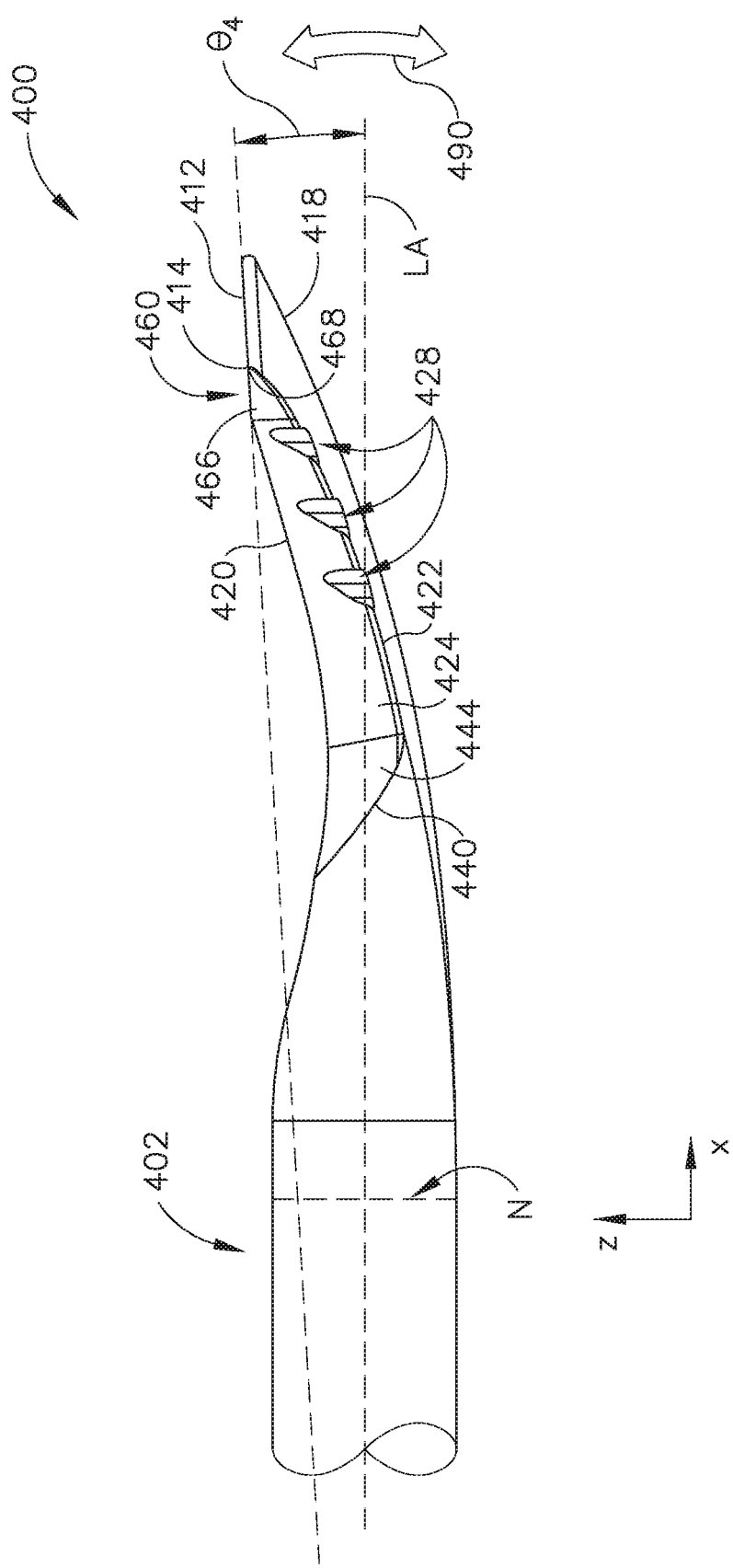
FIG. 33 depicts a side elevational view of the blade of FIG. 28.

As best seen in FIG. 33, first face (412) defines an angle ($\theta_4$) with the longitudinal axis (LA) along the x-z plane. By way of example only, angle ($\theta_4$) may be between approximately 0 degrees and approximately 10 degrees. As another merely illustrative example, first face (412) may define an angle ($\theta_4$) with the longitudinal axis (LA) that is the same as the corresponding angle defined by a corresponding face of a conventional Cobb elevator instrument. Alternatively, any other suitable value may be used. It should also be understood that first face (412) need not necessarily be straight along the x-z plane, such that first face (412) generally extends along angle ($\theta_4$). For instance, the center of each edge (410, 414) may be located along a respective line that defines angle ($\theta_4$) with the longitudinal axis (LA), while an intermediate portion of first face (412) bows outwardly in a convex configuration or inwardly in a concave configuration. First face (412) may also provide a convex configuration or a concave configuration along the y-z plane. Alternatively, first face (412) may be flat along the y-z plane.

In the present example, distal edge (410) is used to scrape tissue (e.g., muscle, tendon, ligament, periostium, etc.) from bone, and the radius of curvature of distal edge (410) is configured to prevent blade (400) from gouging bone while blade (400) performs such scraping. Such scraping may include movement of blade (400) along the longitudinal axis (LA) defined by waveguide (402), in the y direction, in the z direction, in an angular movement (arrow (490) in FIG. 33) about a pitch axis passing through the longitudinal axis (LA), and/or in an angular movement (arrow (492) in FIG. 30) about a yaw axis passing through the longitudinal axis (LA). The pitch and/or yaw axes may be located at a position along the longitudinal axis (LA) where the operator is gripping the instrument. Other suitable scraping motions will be apparent to those of ordinary skill in the art in view of the teachings herein. In some instances, blade (400) is ultrasonically inactive during such scraping operations. In some other instances, blade (400) is activated during such scraping operations. It should also be understood that first face (412) may be used as a coagulation flat. In other words, when the operator encounters a bleeder in tissue at the surgical site, first face (412) may be pressed against the bleeder while blade (400) is activated. This may coagulate or seal the bleeder/tissue.

Blade (400) of the present example also includes a pair of lateral edges (420, 430) extending proximally from edge (414) and another pair of lateral edges (422, 432) extending proximally from edge (410). As best seen in FIG. 30, edges (420, 430) are symmetric about the longitudinal axis (LA) of waveguide (402) in this example. In particular, edges (420, 430) each define concave curves and are oriented such that the distance between edges (420, 430) increases along the length of blade (400) in the x direction. By way of example only, the radius of curvature for each edge (420, 430) along the x-y plane may be part of a transitioning variable radius that transitions from approximately 0.25 inches to approximately 2.50 inches. Alternatively, any other suitable curvature may be used. It should also be understood that edges (420, 430) need not necessarily be curved, such that edges (420, 430) may be substantially straight.

Figure 34:
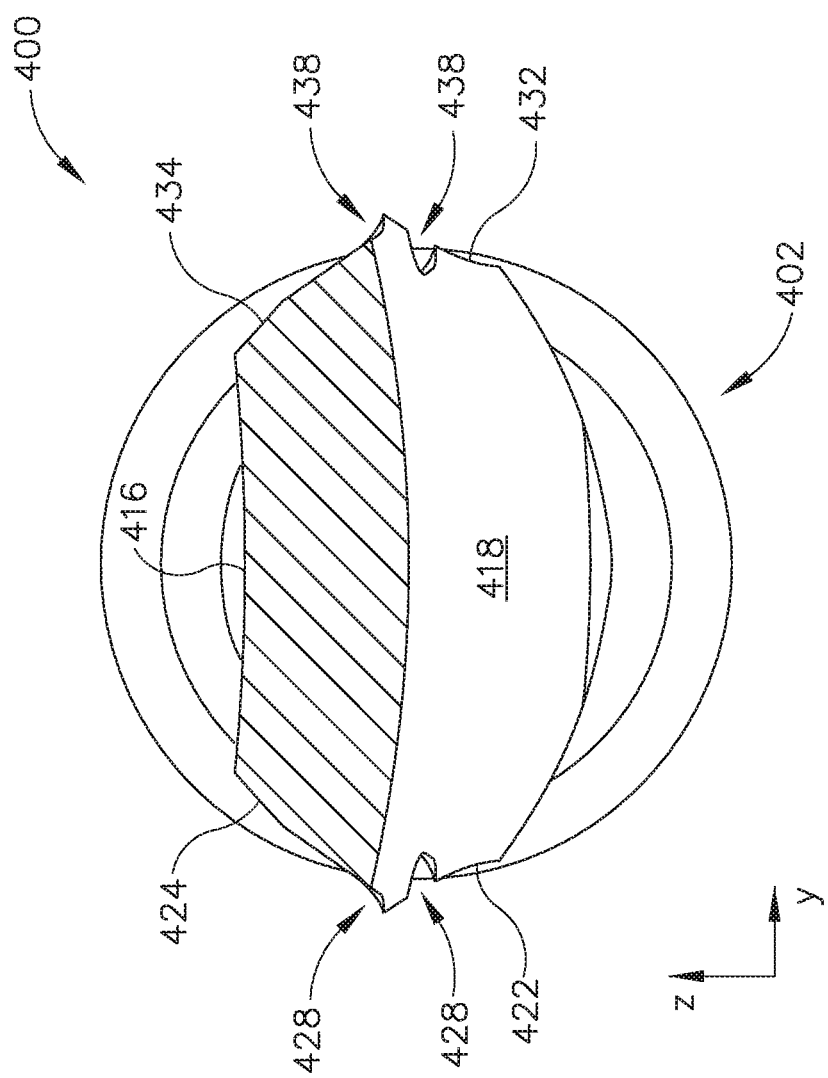
FIG. 34 depicts a cross-sectional view of the blade of FIG. 28, taken along line 34-34 of FIG. 30.
Figure 35:
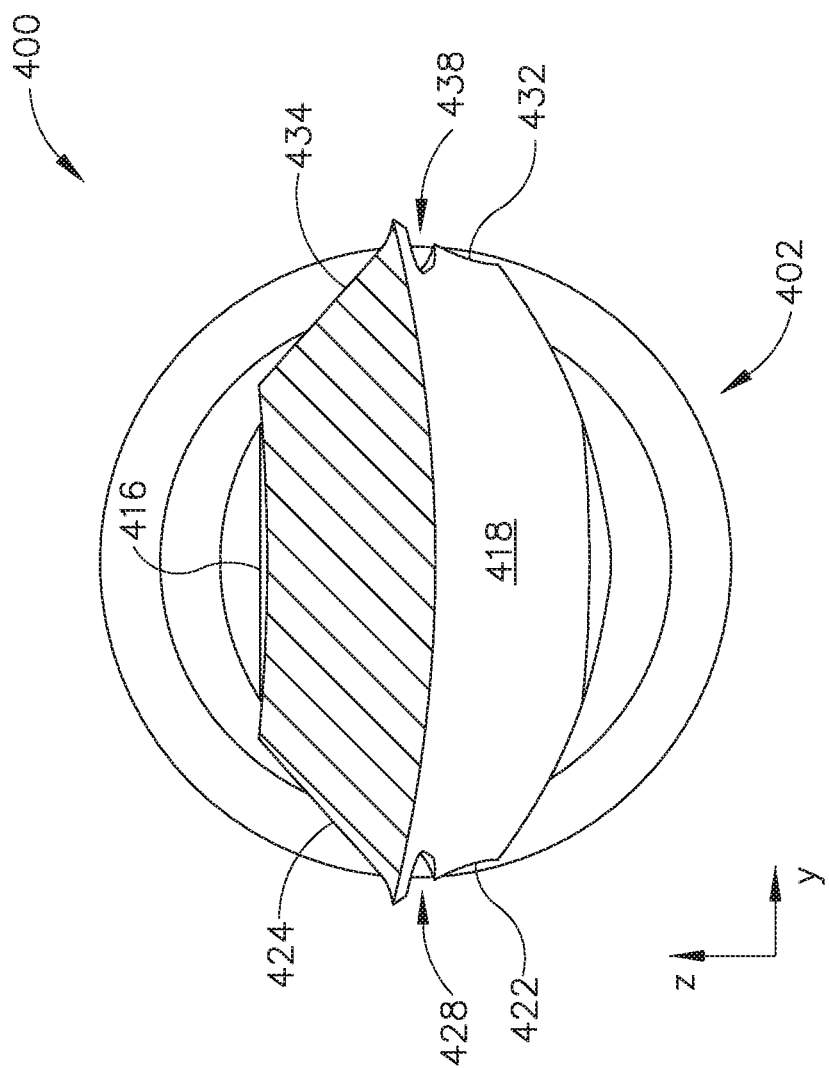
FIG. 35 depicts a cross-sectional view of the blade of FIG. 28, taken along line 35-35 of FIG. 30.

Edges (422, 432) are also symmetric about the longitudinal axis (LA) of waveguide (402) in this example. In particular, edges (422, 432) each define concave curves and are oriented such that the distance between edges (422, 432) increases along the length of blade (400) in the x direction. By way of example only, the radius of curvature for each edge (422, 432) along the x-y plane may be part of a transitioning variable radius that transitions from approximately 0.25 inches to approximately 2.50 inches. Alternatively, any other suitable curvature may be used. It should also be understood that edges (422, 432) need not necessarily be curved, such that edges (422, 432) may be substantially straight. As best seen in FIGS. 34-35, edges (422, 432) have a sharp configuration along at least part of their length. Such sharp configurations may assist in tissue dissection, such as in the side cutting motion referred to below. Edges (422, 432) of the present example also have concave serrations (428, 438), which may further assist in tissue dissection as edges (422, 432) are dragged against tissue. While each set of serrations (428, 438) comprises three recesses in this example, any other suitable number of recesses may be used. In addition, while serrations (428, 438) are formed by arcuate concave recesses in the present example, serrations (428, 438) may instead have a sawtooth configuration and/or any other suitable kind of configuration.

As best seen in FIG. 33, edge (420) is curved along the x-z plane. It should be understood that edge (430) may be similarly curved. By way of example only, edges (420, 430) may each have a radius of curvature along the x-z plane between approximately 0.4 inches and approximately 0.6 inches. Alternatively, any other suitable radius of curvature may be used along the x-z plane. It should also be understood that edges (420, 430) may have different respective radii of curvature along the x-z plane. As also seen in FIG. 33, edge (422) is also curved along the x-z plane. It should be understood that edge (432) may be similarly curved. By way of example only, edges (422, 432) may each have a radius of curvature along the x-z plane between approximately 0.5 inches and approximately 1.0 inches. Alternatively, any other suitable radius of curvature may be used along the x-z plane. It should also be understood that edges (422, 432) may have different respective radii of curvature along the x-z plane. As also seen in FIG. 33, the radius of curvature for edge (422) along the x-z plane is different from the radius of curvature of edge (420) along the x-z plane. In some other versions, edges (420, 422) may have the same radius of curvature along the x-z plane.

Edges (420, 422) partially bound a laterally presented second face (424); while edges (430, 432) partially bound a laterally presented third face (434). Faces (424, 434) are on opposite sides of blade (400) along the y axis. Faces (424, 434) are oriented obliquely and/or curved along the x-y plane (FIG. 30), along the x-z plane (FIG. 33), and along the y-z plane (FIG. 35). As best seen in FIGS. 34-35, and by comparing FIG. 30 with 31, faces (424, 434) are oriented upwardly and outwardly. In some versions, faces (424, 434) are flat. In some other versions, faces (424, 434) are convex along the y-z plane. In still other versions, faces (424, 434) are concave along the y-z plane. As yet another merely illustrative alternative, faces (424, 434) may each have at least one region that is convex along the y-z plane and at least one region that is concave along the y-z plane; or some other combination of convex, concave, and/or flat regions.

Figure 36:
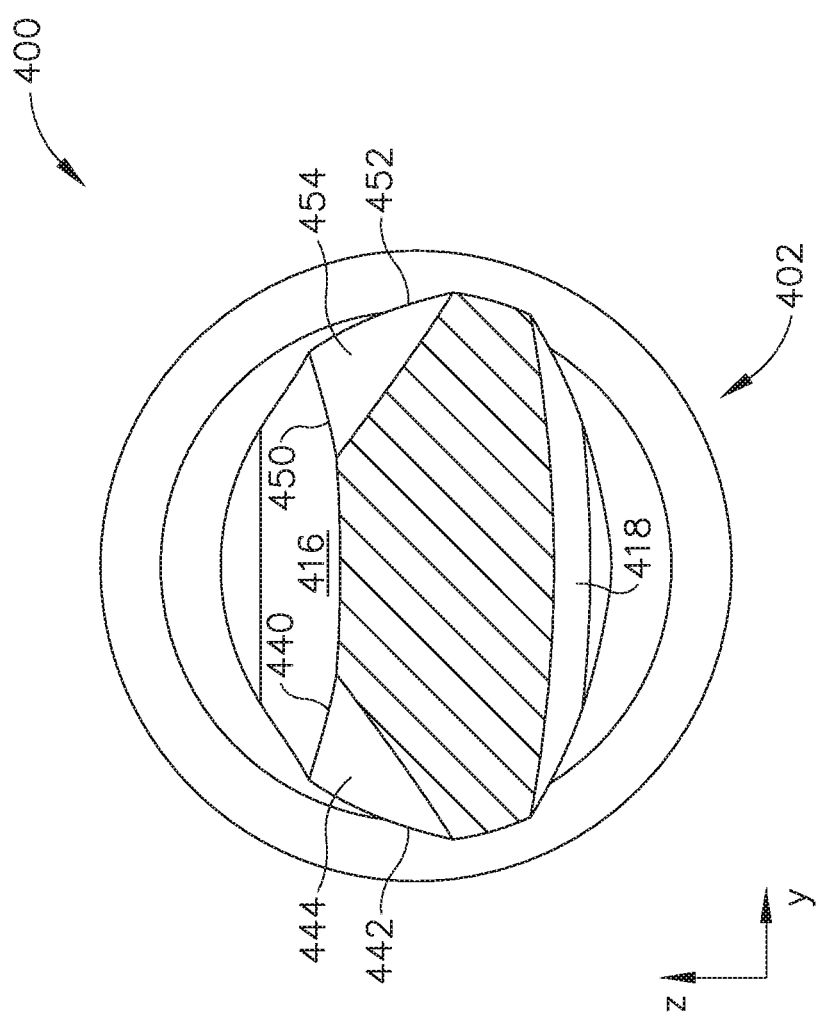
FIG. 36 depicts a cross-sectional view of the blade of FIG. 28, taken along line 36-36 of FIG. 30.
Figure 37:
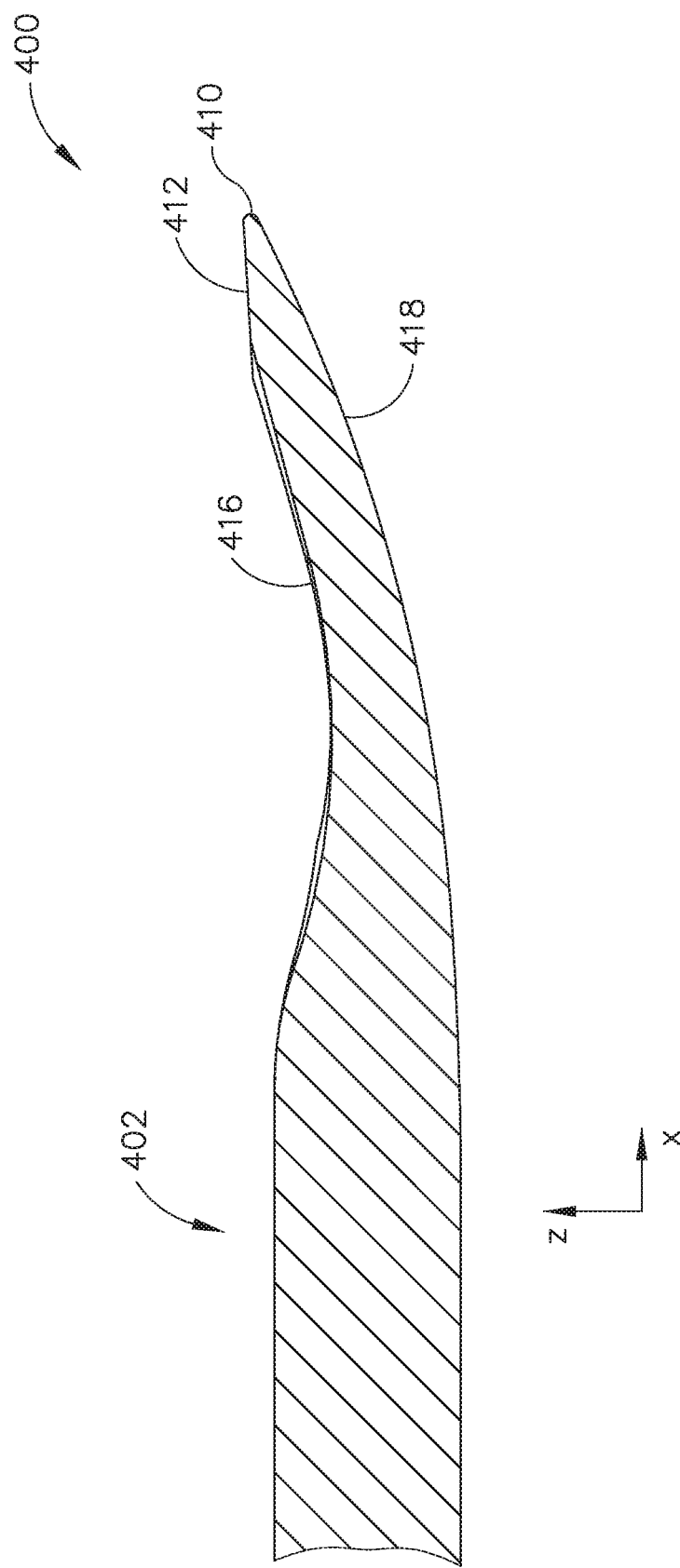
FIG. 37 depicts a cross-sectional view of the blade of FIG. 28, taken along line 37-37 of FIG. 30.
Figure 38:
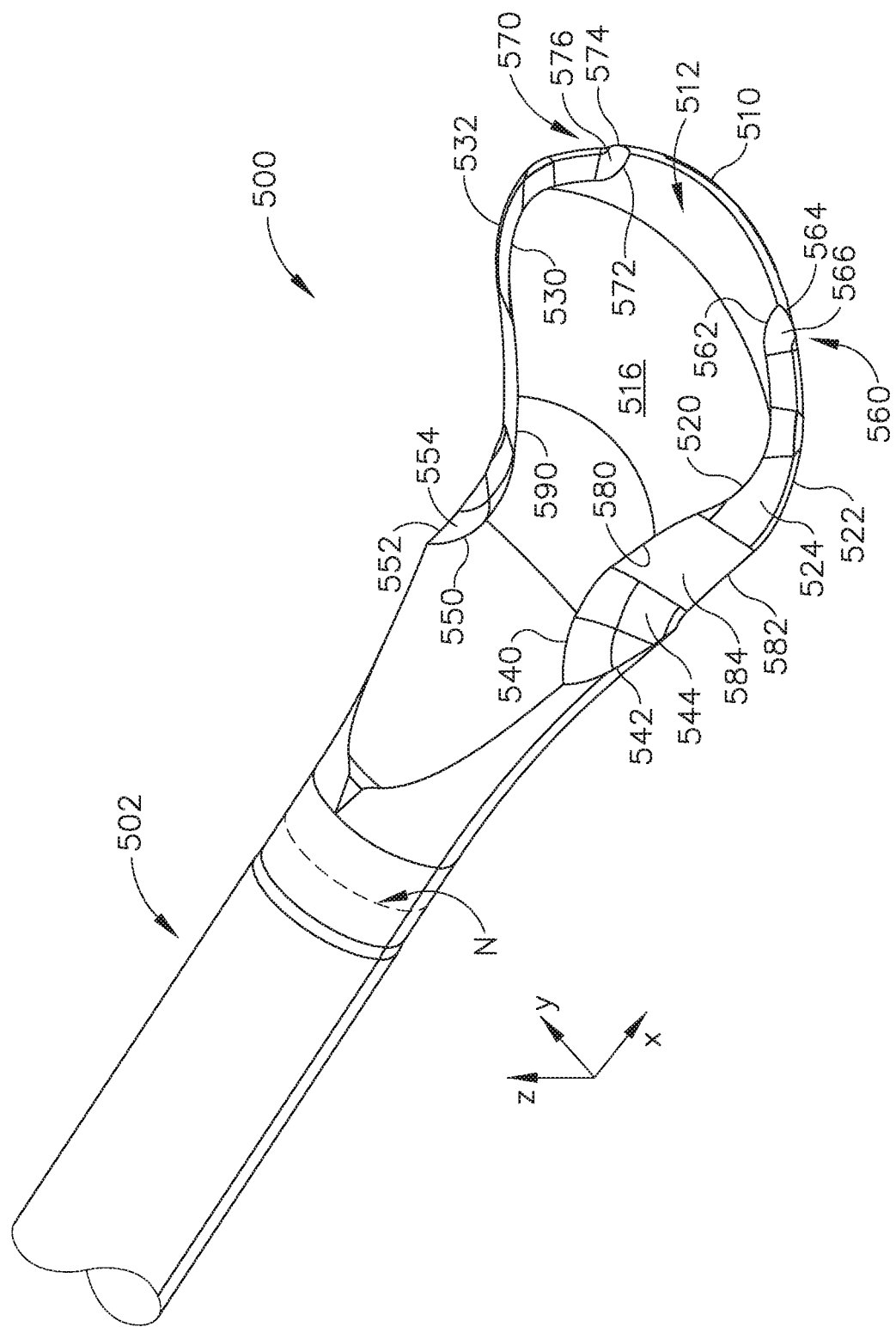
FIG. 38 depicts a top perspective view of another exemplary alternative ultrasonic blade suitable for incorporation in the instrument of FIG. 2.

As best seen in FIGS. 30, 33, and 36, blade (400) of this example further includes a proximal convex edge (440) and an adjacent proximal edge (442), which together partially bound a convex fourth face (444). Proximal convex edge (440) extends continuously from edge (420) described above. In some versions, edge (420) is substantially straight in the x-y plane while edge (440) is curved in the x-y plane. In versions where edge (420) has a radius of curvature along the x-y plane, edge (440) has a radius of curvature along the x-y plane that is less than the radius of curvature of edge (420) along the x-y plane. By way of example only, edge (440) may have a radius of curvature along the x-y plane between approximately 0.10 inches and approximately 0.15 inches. Alternatively, any other suitable radius of curvature may be used along the x-y plane. Fourth face (444) extends continuously from second face (424).

Similarly, blade (400) includes a proximal convex edge (450) and an adjacent proximal edge (452), which together partially bound a convex fifth face (454). Proximal convex edge (450) extends continuously from edge (430) described above. In some versions, edge (420) is substantially straight in the x-y plane while edge (450) is curved in the x-y plane. In versions where edge (430) has a radius of curvature along the x-y plane, edge (450) has a radius of curvature along the x-y plane that is less than the radius of curvature of edge (430) along the x-y plane. By way of example only, edge (450) may have a radius of curvature along the x-y plane between approximately 0.10 inches and approximately 0.15 inches. Alternatively, any other suitable radius of curvature may be used along the x-y plane. Fourth face (454) extends continuously from second face (432).

Blade (400) of the present example further comprises a pair of distal hook portions (460, 470) on opposite ends of distal edge (410). Hook portion (460) comprises a first concave edge (462) and a second concave edge (464). In some versions, edge (420) is substantially straight in the x-y plane while edge (462) is curved in the x-y plane. In versions where edge (420) has a radius of curvature along the x-y plane, edge (462) has a radius of curvature along the x-y plane that is less than the radius of curvature of edge (420) along the x-y plane. The radius of curvature for edge (462) is also less than the radius of curvature for edge (440) in this example. By way of example only, edge (462) may have a radius of curvature along the x-y plane between approximately 0.020 inches and approximately 0.100 inches. Alternatively, any other suitable radius of curvature may be used along the x-y plane.

Similarly, in some versions edge (422) is substantially straight in the x-y plane while edge (464) is curved in the x-y plane. In versions where edge (422) has a radius of curvature along the x-y plane, edge (464) has a radius of curvature along the x-y plane that is less than the radius of curvature of edge (422) along the x-y plane. The radius of curvature for edge (464) is also less than the radius of curvature for edge (442) in this example. By way of example only, edge (464) may have a radius of curvature along the x-y plane between approximately 0.020 inches and approximately 0.100 inches. Alternatively, any other suitable radius of curvature may be used along the x-y plane.

Edges (462, 464) distally converge with distal edge (410) at a sharp point (468). Edges (462, 464) also partially bound a hook face (466). Edge (462) extends continuously from edge (420). Edge (464) extends continuously from edge (422). Face (466) extends continuously from face (422). The combination of faces (422, 444, 466) is thus fully bound by edges (420, 462, 464, 422, 442, 440).

Hook portion (470) comprises a first concave edge (472) and a second concave edge (474). In some versions, edge (430) is substantially straight in the x-y plane while edge (472) is curved in the x-y plane. In versions where edge (430) has a radius of curvature along the x-y plane, edge (472) has a radius of curvature along the x-y plane that is less than the radius of curvature of edge (430) along the x-y plane. The radius of curvature for edge (472) is also less than the radius of curvature for edge (450) in this example. By way of example only, edge (472) may have a radius of curvature along the x-y plane between approximately 0.020 inches and approximately 0.100 inches. Alternatively, any other suitable radius of curvature may be used along the x-y plane.

Similarly, in some versions edge (432) is substantially straight in the x-y plane while edge (474) is curved in the x-y plane. In versions where edge (432) has a radius of curvature along the x-y plane, edge (474) has a radius of curvature along the x-y plane that is less than the radius of curvature of edge (432) along the x-y plane. The radius of curvature for edge (474) is also less than the radius of curvature for edge (452) in this example. By way of example only, edge (474) may have a radius of curvature along the x-y plane of between approximately 0.020 inches and approximately 0.100 inches. Alternatively, any other suitable radius of curvature may be used along the x-y plane.

Edges (472, 474) distally converge with distal edge (410) at a sharp point (478). Edges (472, 474) also partially bound a hook face (476). Edge (472) extends continuously from edge (430). Edge (474) extends continuously from edge (432). Face (476) extends continuously from face (432). The combination of faces (432, 454, 476) is thus fully bound by edges (430, 472, 474, 432, 452, 450).

It should be understood that edges (420, 430, 422, 432, 440, 450, 462, 464, 472, 474) and serrations (428, 438) may be used to perform side cutting of tissue with blade (400). By way of example only, serrations (428, 438) may particularly facilitate cutting of tough tissues such as tendons, ligaments, etc. As one or more edges (420, 430, 422, 432, 440, 450, 462, 464, 472, 474) and/or serrations (428, 438) cut tissue, the corresponding face (444, 454) may assist in driving the tissue distally and outwardly away from blade (400). It should also be understood that hook portions (460, 470) may assist in grabbing tissue and guiding the tissue proximally toward edges (422, 432) and serrations (428, 438) for cutting. For instance, with tissue positioned against any one or more of edges (420, 430, 422, 432, 440, 450, 462, 464, 472, 474) and/or serrations (428, 438), blade (400) may be moved along the y axis, along the z axis, in an angular movement (arrow (490) in FIG. 33) about a pitch axis passing through the longitudinal axis (LA), and/or in an angular movement (arrow (492) in FIG. 30) about a yaw axis passing through the longitudinal axis (LA). Other suitable side cutting motions will be apparent to those of ordinary skill in the art in view of the teachings herein. The pitch and/or yaw axes may be located at a position along the longitudinal axis (LA) where the operator is gripping the instrument. In some instances, blade (400) is ultrasonically inactive during such side cutting operations. In some other instances, blade (400) is activated during such side cutting operations.

Blade (400) of the present example also includes a laterally presented, concave eighth face (416) and a laterally presented, convex ninth face (418). As best seen in FIGS. 34-37, faces (416, 418) are on opposite sides of blade (400) along the z axis. The concavity of eighth face (416) is configured to allow tissue to gather within the recess provided by eighth face (416) as the tissue is scraped from bone by distal edge (410). Ninth face (418) is configured to provide a blunt camming surface to promote blunt dissection with blade (400). It should also be understood that ninth face (418) may be used to provide coagulation. In other words, when the operator encounters a bleeder in tissue at the surgical site, ninth face (418) may be pressed against the bleeder while blade (400) is activated. This may coagulate or seal the bleeder/tissue.

In some versions, faces (416, 418) have the same radius of curvature along the x-z plane. Alternatively, in the present examples (416, 418) have different radii of curvature along the x-z plane. By way of example only, the radius of curvature of face (416) along the x-z plane is between approximately 0.4 inches and approximately 0.6 inches; while the radius of curvature of face (418) along the x-z plane is between approximately 0.25 inches and approximately 0.45 inches. In some versions, the curvature of eighth face (416) and/or ninth face (418) along the x-z plane varies along the length of face (416, 418). As another merely illustrative example, eighth face (416) and/or ninth face (418) may have a curvature along the x-z plane that is the same as the curvature of a corresponding faces a conventional Cobb elevator instrument. Alternatively, any other suitable radius or radii of curvature may be used along the x-z plane. It should also be understood that faces (416, 418) may have different respective radii of curvature along the x-z plane.

Similarly, faces (416, 418) may have the same radius of curvature along the y-z plane. Alternatively, in the present example faces (416, 418) have different radii of curvature along the y-z plane. By way of example only, the radius of curvature of face (416) along the y-z plane is between approximately 0.4 inches and approximately 0.6 inches; while the radius of curvature of face (418) along the y-z plane is between approximately 0.25 inches and approximately 0.45 inches. In some versions, the curvature of eighth face (416) and/or ninth face (418) along the y-z plane varies along the width of face (416, 418). As another merely illustrative example, eighth face (416) and/or ninth face (418) may have a curvature along the y-z plane that is the same as the curvature of a corresponding faces a conventional Cobb elevator instrument. Alternatively, any other suitable radius or radii of curvature may be used along the y-z plane. It should also be understood that faces (416, 418) may have different respective radii of curvature along the y-z plane.

D. Exemplary Ultrasonic Blade with Cobb Tip and Distal Serrations

FIGS. 38-46 show an exemplary alternative ultrasonic blade (500) and waveguide (502) that may be readily incorporated into instrument (20, 120). In particular, blade (500) and waveguide (502) may be mechanically and acoustically coupled with transducer (26, 126) in place of waveguide (28, 128) and blade (24, 132). In the present example, blade (500) and waveguide (502) are configured such that a distal-most node (N) is located just proximal to blade (500). It should be understood that the distal-most node (N) corresponds to a node associated with resonant ultrasonic vibrations communicated through waveguide (502) and blade (500). When blade (500) is activated with ultrasonic vibrations, the vibrational movement may be along the longitudinal axis (LA). In addition, the vibrational movement may be in an angular movement (arrow (596) in FIG. 43) along the x-z plane, about a pitch axis passing through the longitudinal axis (LA) at the distal-most node (N). Furthermore, the vibrational movement may be in an angular movement (arrow (598) in FIG. 40) along the x-y plane, about a yaw axis passing through the longitudinal axis (LA) at the distal-most node (N). It should therefore be understood that blade (500) may provide non-longitudinal modes of resonance. By way of example only, when blade (500) is activated to vibrate at an ultrasonic frequency, the ratio of lateral displacement of blade (500) from the longitudinal axis (LA) to the longitudinal displacement of blade (500) along the longitudinal axis (LA) is between approximately 0.46 to approximately 0.55. Alternatively, any other suitable ratio disclosed herein (among other ratios) may be used.

Figure 40:
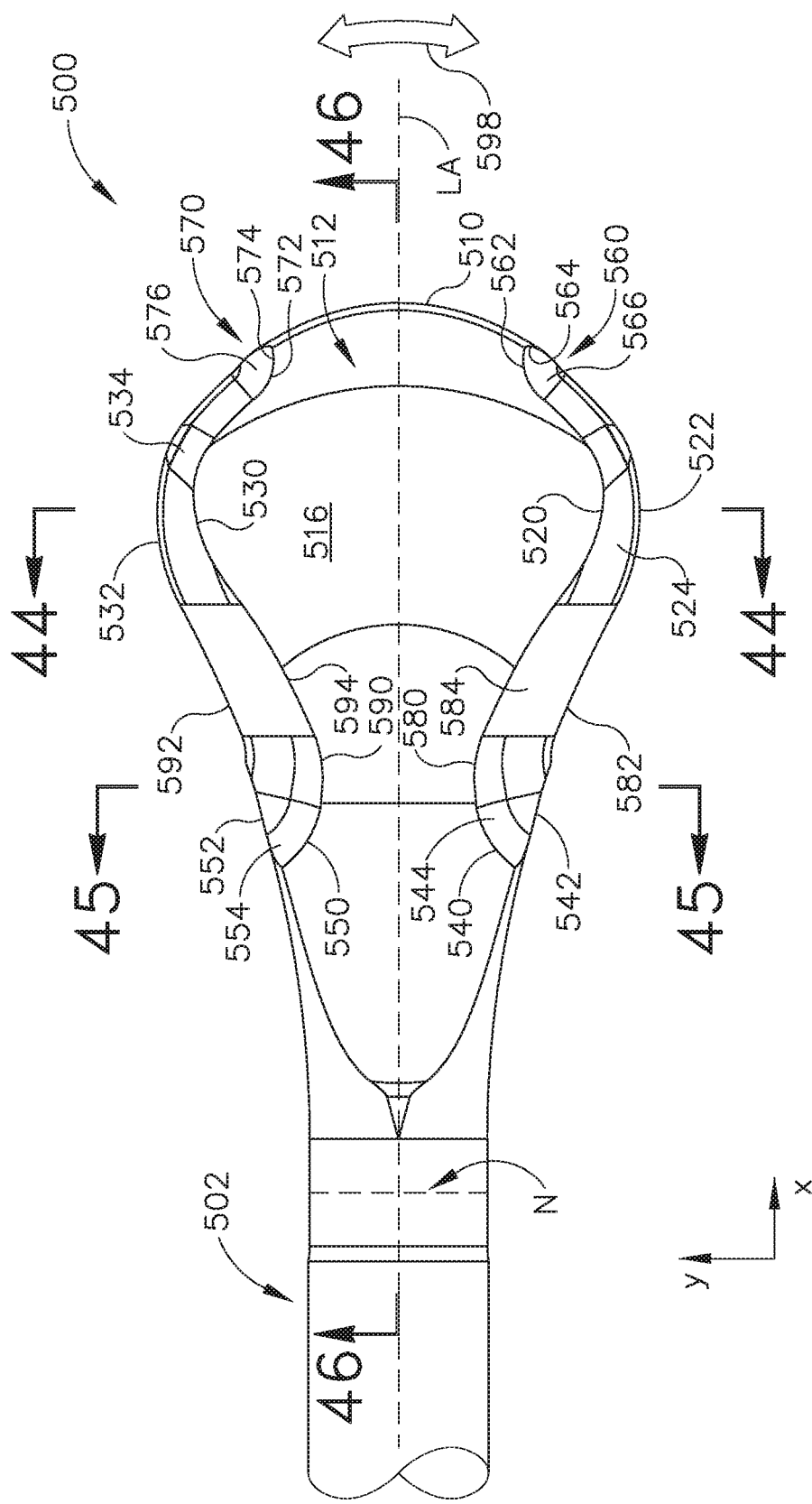
FIG. 40 depicts a top plan view of the blade of FIG. 38.
Figure 41:
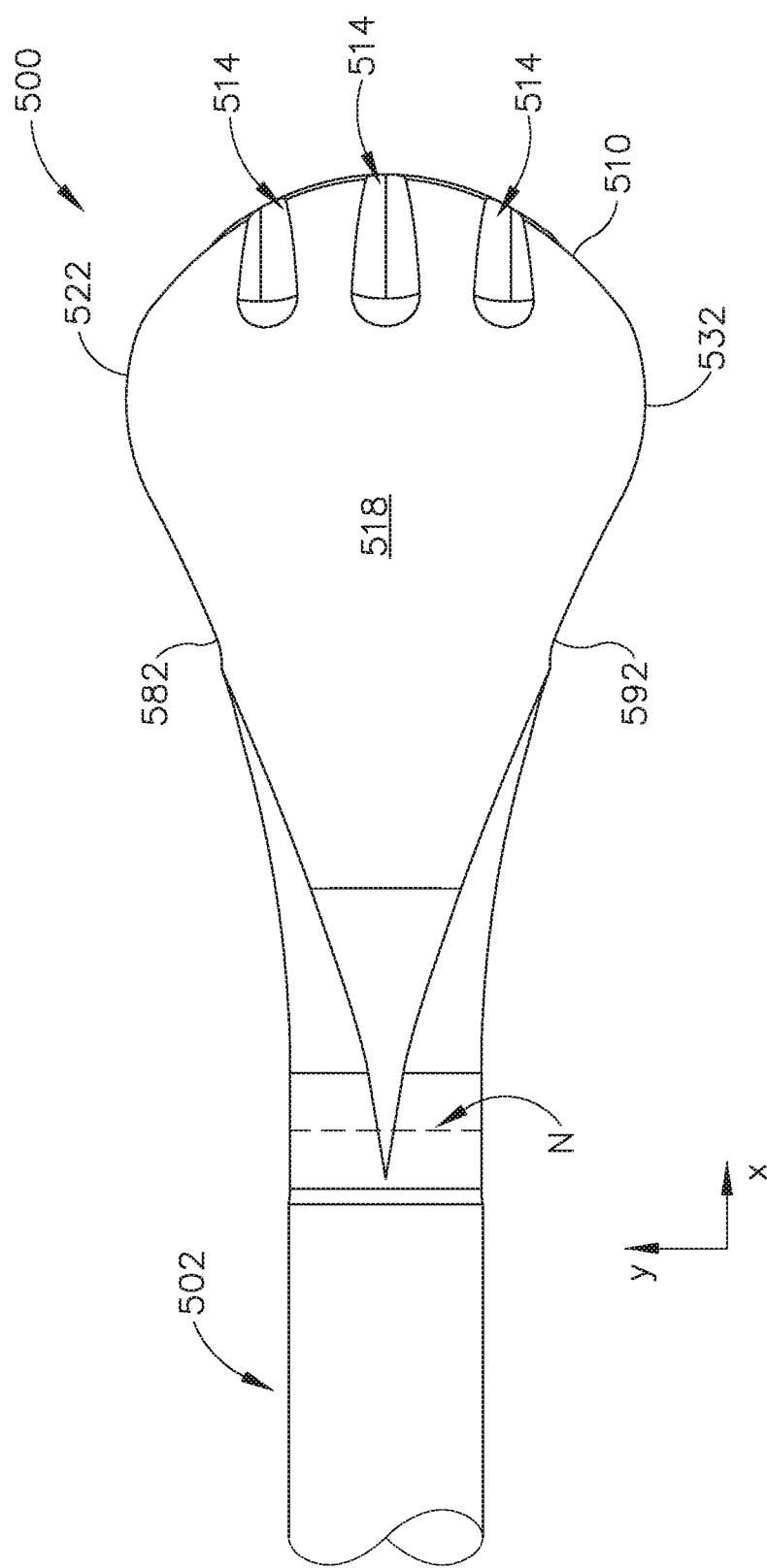
FIG. 41 depicts a bottom plan view of the blade of FIG. 38.

Blade (500) of this example comprises a distally located and laterally presented first face (512). First face (512) is partially bound by a curved distal edge (510). FIGS. 40-41 show the curvature of edge (510) along an x-y plane. By way of example only, the radius of curvature of edges (510) along the x-y plane is between approximately 0.1 inches and approximately 0.3 inches. As another merely illustrative example, the curvature of edges (510, 514) along the x-y plane may be the same as the curvature along the x-y plane in a distal edge of a conventional Cobb elevator instrument. Alternatively, any other suitable radius of curvature may be used along the x-y plane. It should also be understood that edges (510, 514) may have different respective radii of curvature along the x-y plane. As shown in FIG. 32, distal edge (510) is substantially flat along a y-z plane.

Figure 39:
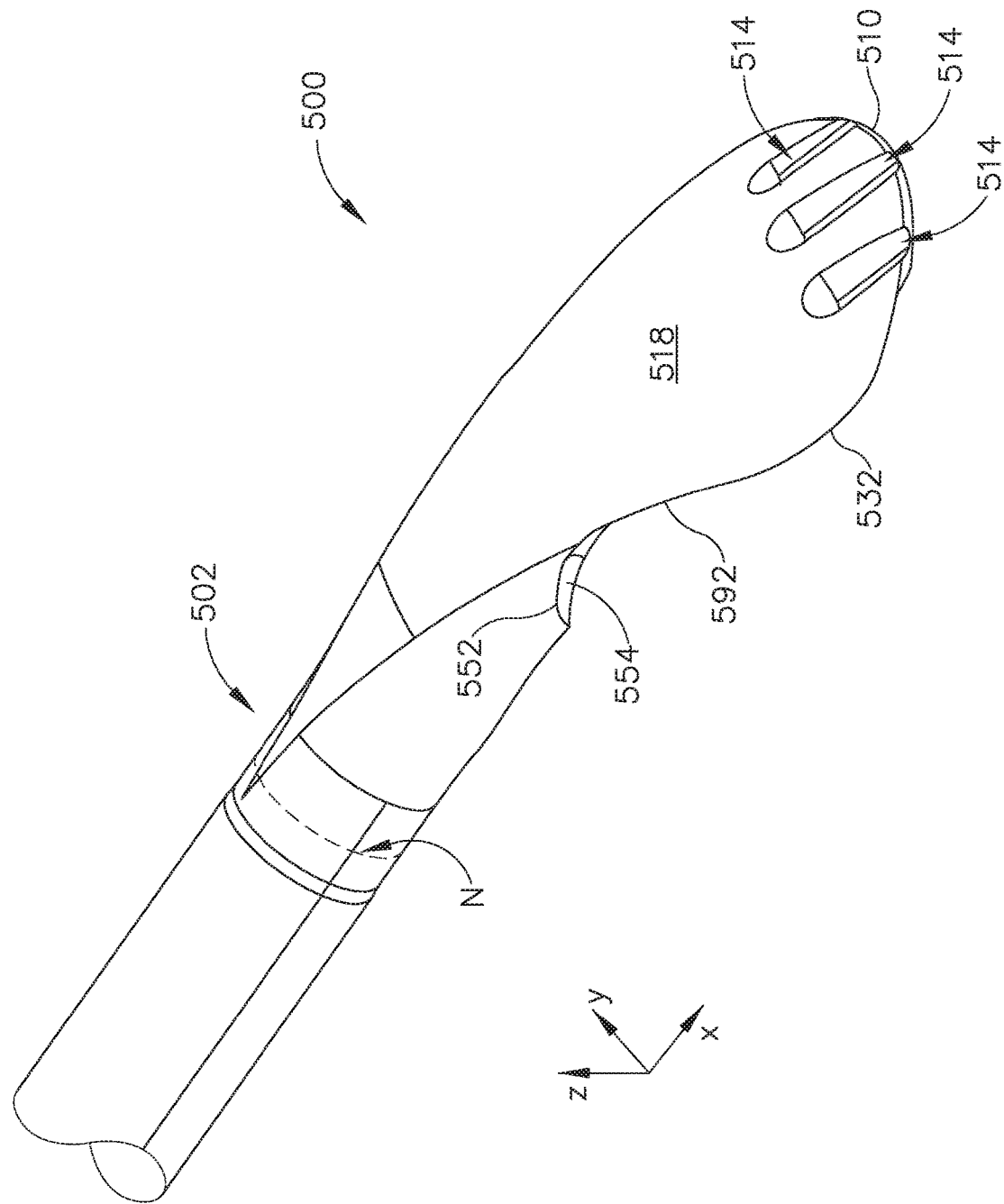
FIG. 39 depicts a bottom perspective view of the blade of FIG. 38.
Figure 42:
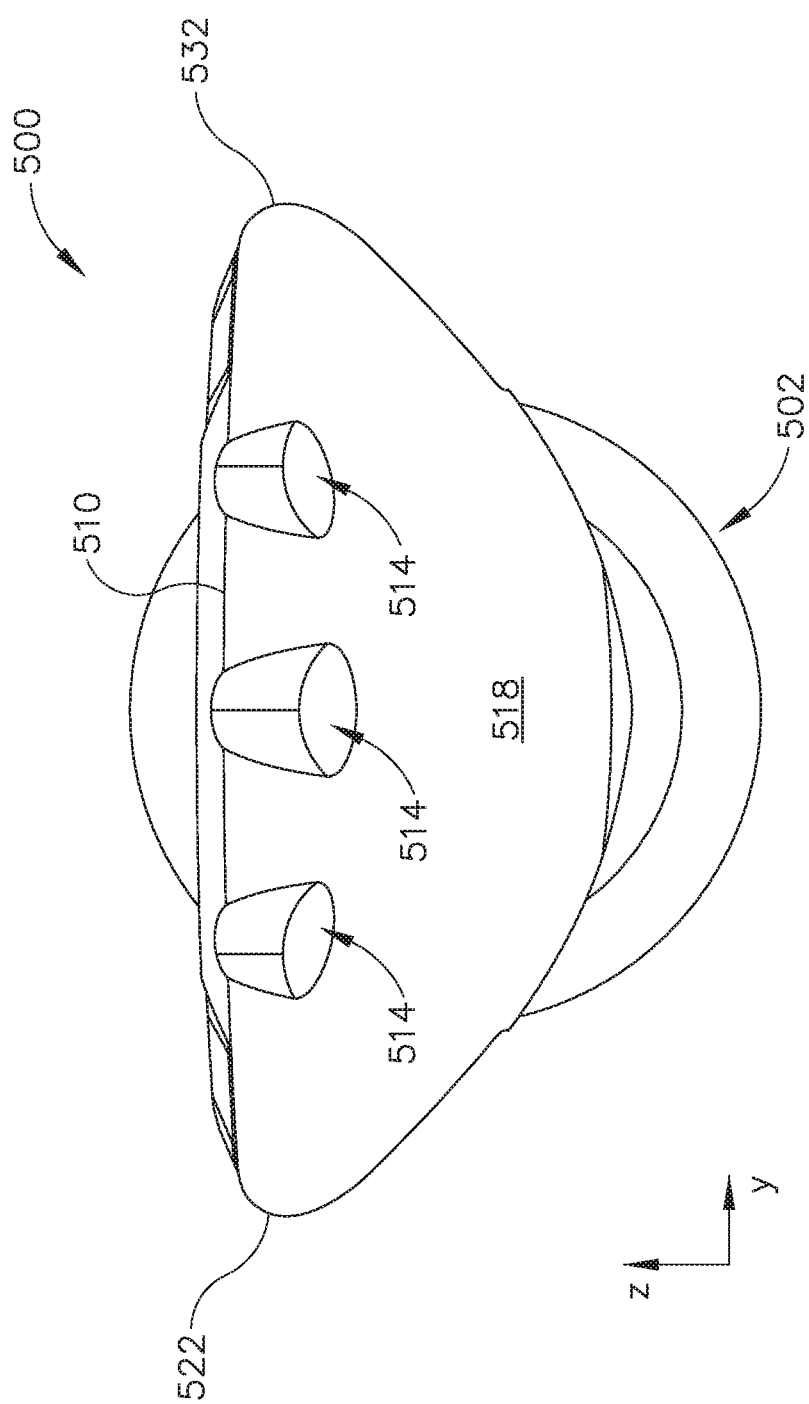
FIG. 42 depicts a front end view of the blade of FIG. 38.

As also best seen in FIGS. 39 and 41-42, distal edge (510) of the present example includes concave serrations (514), which may further assist in tissue dissection or separation as edge (510) is dragged against tissue. While serrations (514) comprise three recesses in this example, any other suitable number of recesses may be used. In addition, while serrations (514) are formed by arcuate concave recesses in the present example, serrations (514) may instead have a sawtooth configuration and/or any other suitable kind of configuration.

Figure 43:
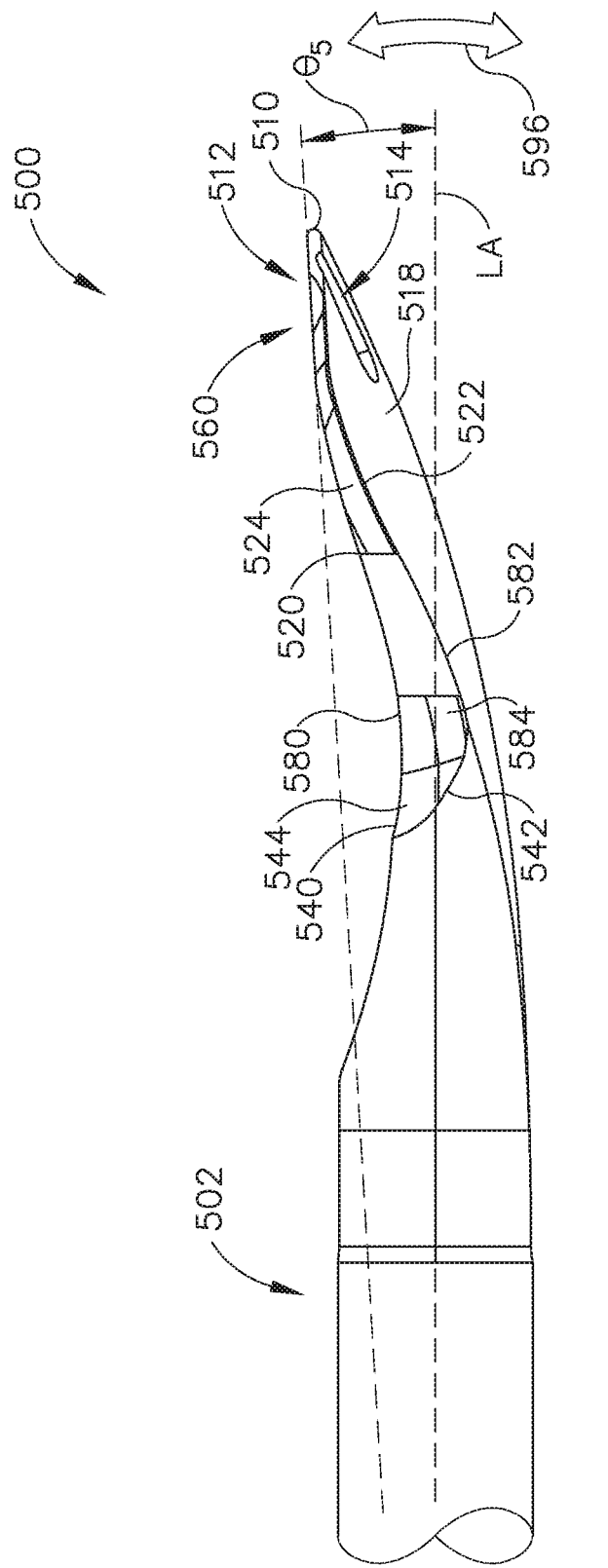
FIG. 43 depicts a side elevational view of the blade of FIG. 38.

As best seen in FIG. 43, first face (5112) defines an angle ($\theta_5$) with the longitudinal axis (LA) along the x-z plane. By way of example only, angle ($\theta_5$) may be between approximately 0 degrees and approximately 10 degrees. As another merely illustrative example, first face (512) may define an angle ($\theta_5$) with the longitudinal axis (LA) that is the same as the corresponding angle defined by a corresponding face of a conventional Cobb elevator instrument. Alternatively, any other suitable value may be used. It should also be understood that first face (512) need not necessarily be straight along the x-z plane, such that first face (512) generally extends along angle ($\theta_5$). For instance, the center of edge (510) may be located along a respective line that defines angle ($\theta_5$) with the longitudinal axis (LA), while an intermediate portion of first face (512) bows outwardly in a convex configuration or inwardly in a concave configuration. First face (512) may also provide a convex configuration or a concave configuration along the y-z plane. Alternatively, first face (512) may be flat along the y-z plane.

In the present example, distal edge (510) is used to scrape tissue (e.g., muscle, tendon, ligament, periosteum, etc.) from bone, and the radius of curvature of distal edge (510) is configured to prevent blade (500) from gouging bone while blade (500) performs such scraping. Such scraping may include movement of blade (500) along the longitudinal axis (LA) defined by waveguide (502), in the y direction, in the z direction, in an angular movement (arrow (596) in FIG. 43) about a pitch axis passing through the longitudinal axis (LA), and/or in an angular movement (arrow (598) in FIG. 40) about a yaw axis passing through the longitudinal axis (LA). The pitch and/or yaw axes may be located at a position along the longitudinal axis (LA) where the operator is gripping the instrument. Other suitable scraping motions will be apparent to those of ordinary skill in the art in view of the teachings herein. Serrations (514) may further assist in such scraping operations by promoting dissection of tissue. In some instances, blade (500) is ultrasonically inactive during such scraping operations. In some other instances, blade (500) is activated during such scraping operations. It should also be understood that first face (512) may be used as a coagulation flat. In other words, when the operator encounters a bleeder in tissue at the surgical site, first face (512) may be pressed against the bleeder while blade (500) is activated. This may coagulate or seal the bleeder/tissue.

Blade (500) of the present example also includes a pair of lateral edges (520, 530) and another pair of lateral edges (522, 532). As best seen in FIG. 40, edges (520, 530) are symmetric about the longitudinal axis (LA) of waveguide (502) in this example. In particular, edges (520, 530) each define convex curves and are oriented such that the distance between edges (520, 530) increases along the length of blade (500) in the x direction. By way of example only, the radius of curvature for each edge (520, 530) along the x-y plane may be between approximately 0.050 inches and approximately 0.375 inches. Alternatively, any other suitable curvature may be used. It should also be understood that edges (520, 530) need not necessarily be curved, such that edges (520, 530) may be substantially straight.

Edges (522, 532) are also symmetric about the longitudinal axis (LA) of waveguide (502) in this example. In particular, edges (522, 532) each define convex curves and are oriented such that the distance between edges (522, 532) increases along the length of blade (500) in the x direction. By way of example only, the radius of curvature for each edge (522, 532) along the x-y plane may be between approximately 0.10 inches and approximately 0.25 inches. Alternatively, any other suitable curvature may be used. It should also be understood that edges (522, 532) need not necessarily be curved, such that edges (522, 532) may be substantially straight. Edges (522, 532) may also have a sharp configuration along at least part of their length. Such sharp configurations may assist in tissue dissection, such as in the side cutting motion referred to below.

As best seen in FIG. 43, edge (520) is curved along the x-z plane. It should be understood that edge (530) may be similarly curved. By way of example only, edges (520, 530) may each have a radius of curvature along the x-z plane between approximately 0.4 inches and approximately 0.6 inches. Alternatively, any other suitable radius of curvature may be used along the x-z plane. It should also be understood that edges (520, 530) may have different respective radii of curvature along the x-z plane. As also seen in FIG. 43, edge (522) is also curved along the x-z plane. It should be understood that edge (532) may be similarly curved. By way of example only, edges (522, 532) may each have a radius of curvature along the x-z plane between approximately 0.3 inches and approximately 0.6 inches. Alternatively, any other suitable radius of curvature may be used along the x-z plane. It should also be understood that edges (522, 532) may have different respective radii of curvature along the x-z plane. As also seen in FIG. 43, the radius of curvature for edge (522) along the x-z plane is different from the radius of curvature of edge (520) along the x-z plane. In some other versions, edges (520, 522) may have the same radius of curvature along the x-z plane.

Figure 44:
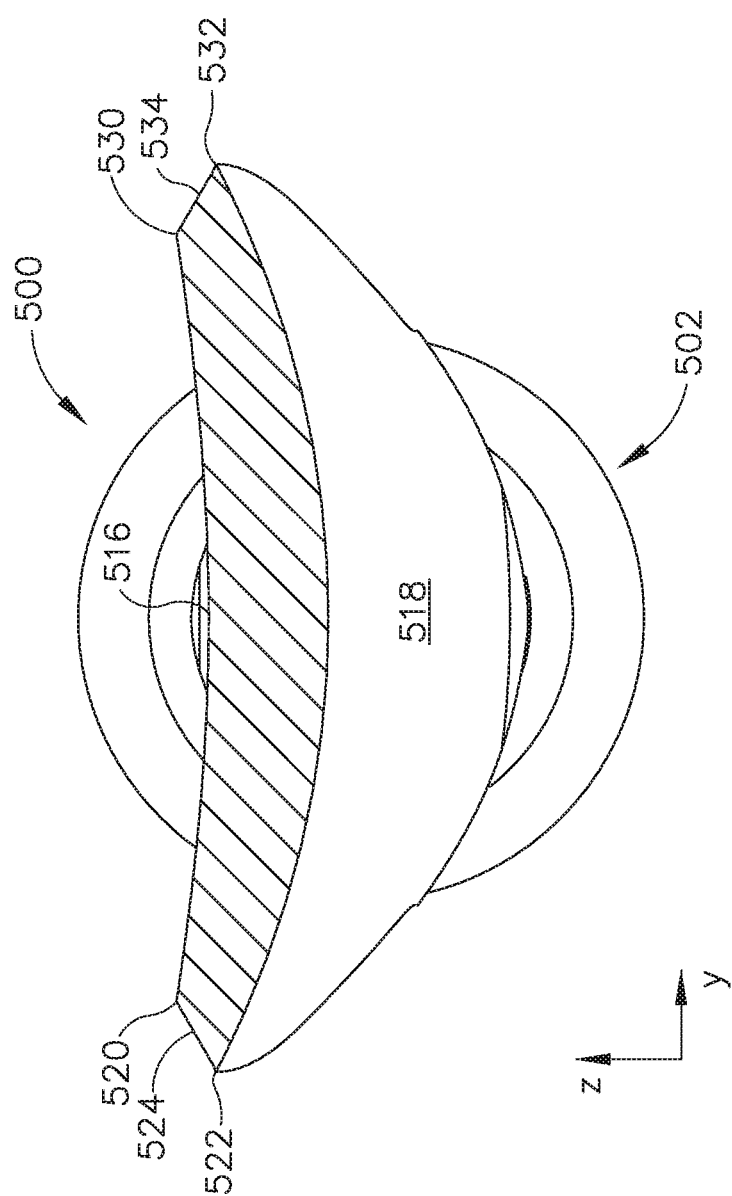
FIG. 44 depicts a cross-sectional view of the blade of FIG. 38, taken along line 44-44 of FIG. 40.

Edges (520, 522) partially bound a laterally presented second face (524); while edges (530, 532) partially bound a laterally presented third face (534). Faces (524, 534) are oriented obliquely and/or curved along the x-y plane (FIG. 40), along the x-z plane (FIG. 43), and along the y-z plane (FIG. 44). Faces (524, 534) are on opposite sides of blade (500) along the y axis. As best seen in FIG. 44, and by comparing FIG. 40 with FIG. 41, faces (524, 534) are oriented upwardly and outwardly. In some versions, faces (524, 534) are flat. In some other versions, faces (524, 534) are convex along the y-z plane. In still other versions, faces (524, 534) are concave along the y-z plane. As yet another merely illustrative alternative, faces (524, 534) may each have at least one region that is convex along the y-z plane and at least one region that is concave along the y-z plane; or some other combination of convex, concave, and/or flat regions.

Figure 45:
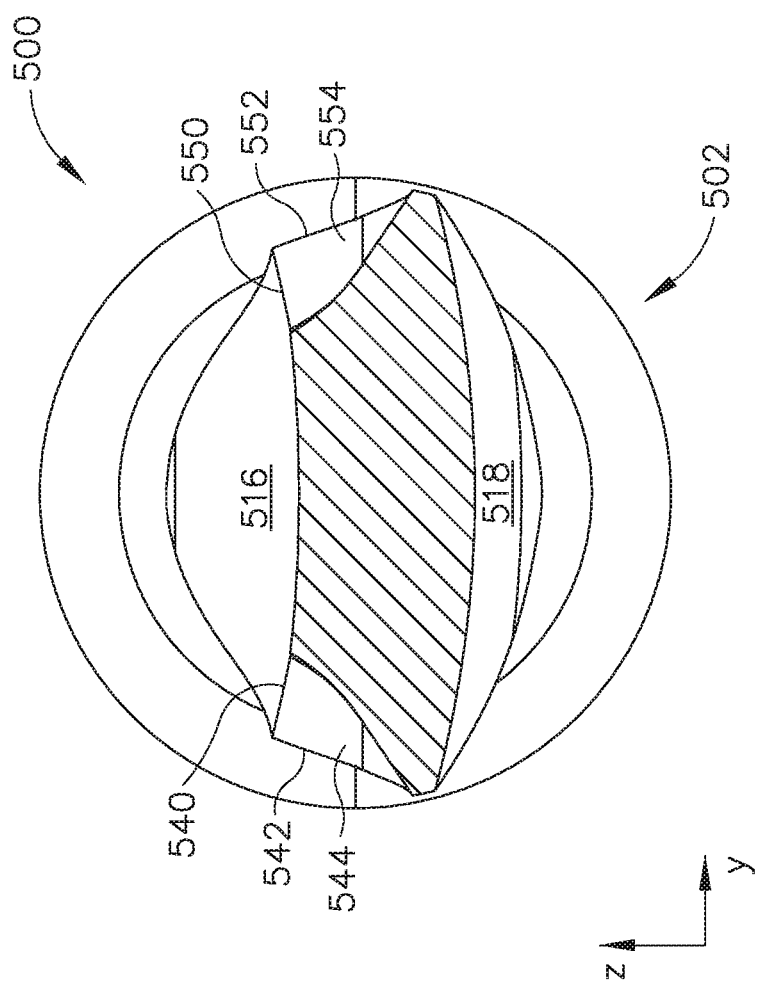
FIG. 45 depicts a cross-sectional view of the blade of FIG. 38, taken along line 45-45 of FIG. 40.

As best seen in FIGS. 40, 43, and 45, blade (500) of this example further includes a proximal convex edge (540) and an adjacent proximal edge (542), which together partially bound a convex fourth face (544). An intervening edge (580) extends continuously between proximal convex edge (540) and edge (520) described above. In some versions, intervening edge (580) is substantially straight in the x-y plane while edge (540) is curved in the x-y plane. In versions where edge (580) has a radius of curvature along the x-y plane, edge (540) has a radius of curvature along the x-y plane that is less than the radius of curvature of edge (580) along the x-y plane. The radius of curvature for edge (540) may also be less than, greater than, or equal to the radius of curvature of edge (520) along the x-y plane. By way of example only, edge (540) may have a radius of curvature along the x-y plane between approximately 0.050 inches and approximately 0.250 inches. Alternatively, any other suitable radius of curvature may be used along the x-y plane. An intervening face (584) extends continuously from fourth face (544) to second face (524). Intervening face (584) is partially bound by intervening edge (580) referred to above and another intervening edge (582), which extends continuously between edge (522) and edge (547).

Similarly, blade (500) includes a proximal convex edge (550) and an adjacent proximal edge (552), which together partially bound a convex fifth face (554). An intervening edge (590) extends continuously between proximal convex edge (550) and edge (530) described above. In some versions, intervening edge (590) is substantially straight in the x-y plane while edge (550) is curved in the x-y plane. In versions where edge (590) has a radius of curvature along the x-y plane, edge (550) has a radius of curvature along the x-y plane that is less than the radius of curvature of edge (590) along the x-y plane. The radius of curvature for edge (550) may also be less than, greater than, or equal to the radius of curvature of edge (530) along the x-y plane. By way of example only, edge (550) may have a radius of curvature along the x-y plane between approximately 0.050 inches and approximately 0.250 inches. Alternatively, any other suitable radius of curvature may be used along the x-y plane. An intervening face (594) extends continuously from fourth face (554) to second face (534). Intervening face (594) is partially bound by intervening edge (590) referred to above and another intervening edge (592), which extends continuously between edge (532) and edge (552).

Blade (500) of the present example further comprises a pair of distal recess portions (560, 570) on opposite ends of distal edge (510). Recess portion (560) comprises a first concave edge (562) and a second concave edge (564). The radius of curvature of edge (562) along the x-y plane may be less than, greater than, or equal to the radius of curvature of edge (520) along the x-y plane. By way of example only, edge (562) may have a radius of curvature along the x-y plane between approximately 0.01 inches and approximately 0.05 inches. Alternatively, any other suitable radius of curvature may be used along the x-y plane. Similarly, the radius of curvature of edge (564) along the x-y plane may be less than, greater than, or equal to the radius of curvature of edge (522) along the x-y plane. Alternatively, any other suitable radius of curvature may be used along the x-y plane.

Edges (562, 564) distally converge with distal edge (510). Edges (562, 564) also partially bound a distal recess face (566). Edge (562) extends continuously from edge (520). Edge (564) extends continuously from edge (522). Face (566) extends continuously from face (522). The combination of faces (522, 544, 584, 564) is thus fully bound by edges (520, 562, 564, 522, 582, 542, 540, 580).

Recess portion (570) comprises a first concave edge (572) and a second concave edge (574). The radius of curvature of edge (572) along the x-y plane may be less than, greater than, or equal to the radius of curvature of edge (530) along the x-y plane. By way of example only, edge (572) may have a radius of curvature along the x-y plane between approximately 0.01 inches and approximately 0.05 inches. Alternatively, any other suitable radius of curvature may be used along the x-y plane. Similarly, the radius of curvature of edge (574) along the x-y plane may be less than, greater than, or equal to the radius of curvature of edge (532) along the x-y plane. Alternatively, any other suitable radius of curvature may be used along the x-y plane.

Edges (572, 574) distally converge with distal edge (510). Edges (572, 574) also partially bound a distal recess face (576). Edge (572) extends continuously from edge (530). Edge (574) extends continuously from edge (532). Face (576) extends continuously from face (532). The combination of faces (532, 554, 594, 574) is thus fully bound by edges (530, 572, 574, 532, 592, 552, 550, 590).

It should be understood that edges (520, 530, 522, 532, 540, 550, 562, 564, 572, 574, 582, 592) may be used to perform side cutting of tissue with blade (500). As one or more edges (520, 530, 522, 532, 540, 550, 562, 564, 572, 574, 582, 592) cut tissue, the corresponding face (544, 554) may assist in driving the tissue distally and outwardly away from blade (500). It should also be understood that recess portions (560, 570) may assist in cutting tissue that is distally located in relation to blade (500); and that faces (566, 576) may further drive cut tissue distally and outwardly away from blade (500). By way of example only, with tissue positioned against any one or more of edges (520, 530, 522, 532, 540, 550, 562, 564, 572, 574, 582, 592), blade (500) may be moved along the y axis, along the z axis, in an angular movement (arrow (596) in FIG. 43) about a pitch axis passing through the longitudinal axis (LA), and/or in an angular movement (arrow (598) in FIG. 40) about a yaw axis passing through the longitudinal axis (LA). Other suitable side cutting motions will be apparent to those of ordinary skill in the art in view of the teachings herein. The pitch and/or yaw axes may be located at a position along the longitudinal axis (LA) where the operator is gripping the instrument. In some instances, blade (500) is ultrasonically inactive during such side cutting operations. In some other instances, blade (500) is activated during such side cutting operations.

Figure 46:
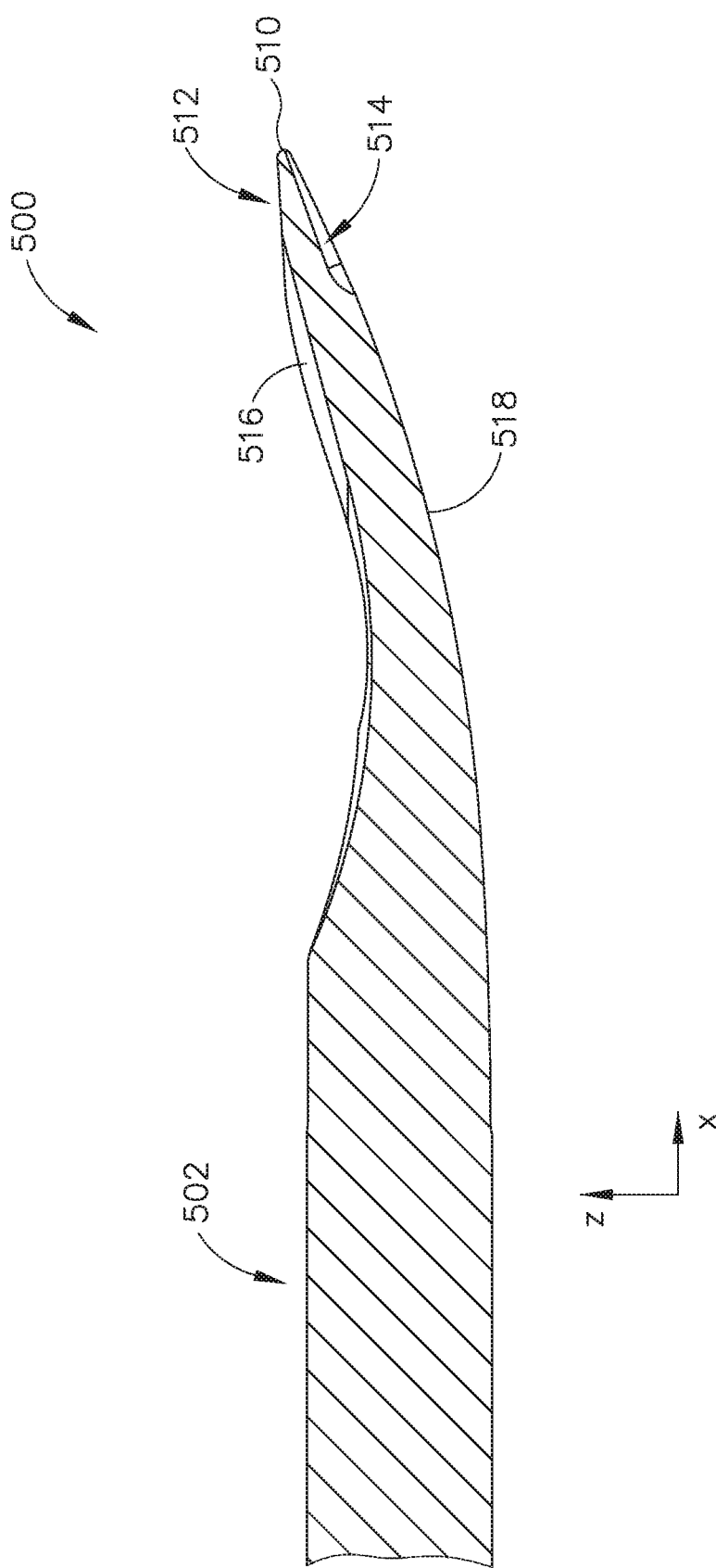
FIG. 46 depicts a cross-sectional view of the blade of FIG. 38, taken along line 46-46 of FIG. 40.
Figure 47:
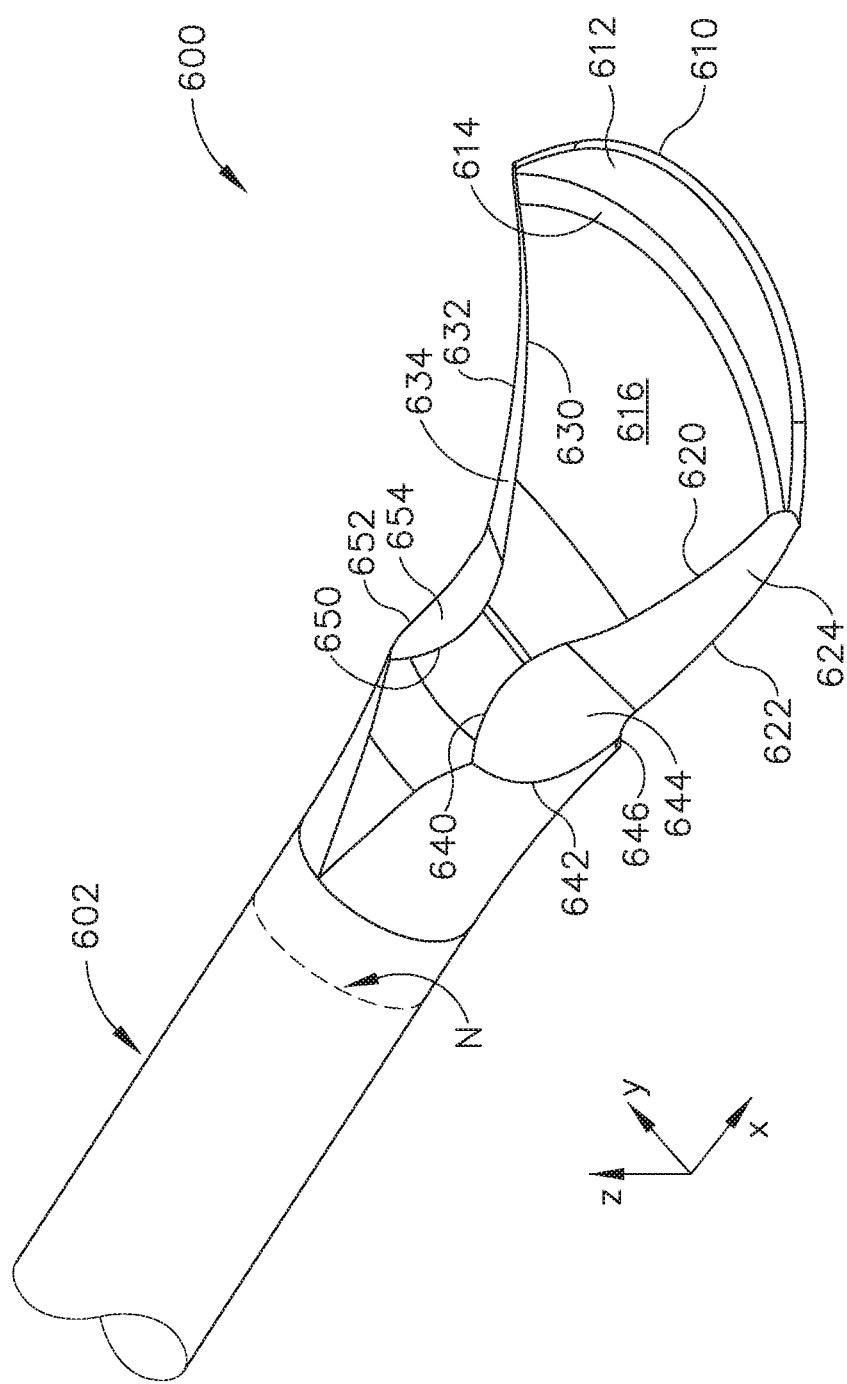
FIG. 47 depicts a top perspective view of another exemplary alternative ultrasonic blade suitable for incorporation in the instrument of FIG. 2.

Blade (500) of the present example also includes a laterally presented, concave eighth face (516) and a laterally presented, convex ninth face (518). As best seen in FIGS. 44-46, faces (516, 518) are on opposite sides of blade (500) along the z axis. As can also be seen in FIGS. 39 and 41-42, the recesses forming serrations (514) in distal edge (510) also extend into face (518). The concavity of eighth face (516) is configured to allow tissue to gather within the recess provided by eighth face (516) as the tissue is scraped from bone by distal edge (510). Ninth face (518) is configured to provide a blunt camming surface to promote blunt dissection with blade (500). It should also be understood that ninth face (518) may be used to provide coagulation. In other words, when the operator encounters a bleeder in tissue at the surgical site, ninth face (518) may be pressed against the bleeder while blade (500) is activated. This may coagulate or seal the bleeder/tissue.

In some versions, faces (516, 518) have the same radius of curvature along the x-z plane. Alternatively, in the present example faces (516, 518) have different radii of curvature along the x-z plane. By way of example only, the radius of curvature of face (516) along the x-z plane is between approximately 0.4 inches and approximately 0.6 inches; while the radius of curvature of face (518) along the x-z plane is between approximately 1.0 inches and approximately 2.0 inches. In some versions, the curvature of eighth face (516) and/or ninth face (518) along the x-z plane varies along the length of face (516, 518). As another merely illustrative example, eighth face (516) and/or ninth face (518) may have a curvature along the x-z plane that is the same as the curvature of a corresponding faces a conventional Cobb elevator instrument. Alternatively, any other suitable radius or radii of curvature may be used along the x-z plane. It should also be understood that faces (516, 518) may have different respective radii of curvature along the x-z plane.

Similarly, faces (516, 518) may have the same radius of curvature along the y-z plane. Alternatively, in the present example faces (516, 518) have different radii of curvature along the y-z plane. By way of example only, the radius of curvature of face (516) along the y-z plane is between approximately 0.4 inches and approximately 0.6 inches; while the radius of curvature of face (518) along the y-z plane is between approximately 0.25 inches and approximately 0.45 inches. In some versions, the curvature of eighth face (516) and/or ninth face (518) along the y-z plane varies along the width of face (516, 518). As another merely illustrative example, eighth face (516) and/or ninth face (518) may have a curvature along the y-z plane that is the same as the curvature of a corresponding faces a conventional Cobb elevator instrument. Alternatively, any other suitable radius or radii of curvature may be used along the y-z plane. It should also be understood that faces (516, 518) may have different respective radii of curvature along the y-z plane.

E. Exemplary Ultrasonic Blade with Cobb Tip and Upper and Lower Proximal Recesses FIGS. 47-55 show an exemplary alternative ultrasonic blade (600) and waveguide (602) that may be readily incorporated into instrument (20, 120). In particular, blade (600) and waveguide (602) may be mechanically and acoustically coupled with transducer (26, 126) in place of waveguide (28, 128) and blade (24, 132). Waveguide (602) includes a flat (606) that is configured and positioned to provide appropriate acoustic tuning of blade (600). In the present example, blade (600) and waveguide (602) are configured such that a distal-most node (N) is located just proximal to blade (600). It should be understood that the distal-most node (N) corresponds to a node associated with resonant ultrasonic vibrations communicated through waveguide (602) and blade (600). When blade (600) is activated with ultrasonic vibrations, the vibrational movement may be along the longitudinal axis (LA). In addition, the vibrational movement may be in an angular movement (arrow (690) in FIG. 52) along the x-z plane, about a pitch axis passing through the longitudinal axis (LA) at the distal-most node (N). Furthermore, the vibrational movement may be in an angular movement (arrow (692) in FIG. 49) along the x-y plane, about a yaw axis passing through the longitudinal axis (LA) at the distal-most node (N). It should therefore be understood that blade (600) may provide non-longitudinal modes of resonance. By way of example only, when blade (600) is activated to vibrate at an ultrasonic frequency, the ratio of lateral displacement of blade (600) from the longitudinal axis (LA) to the longitudinal displacement of blade (600) along the longitudinal axis (LA) is between approximately 0.60 to approximately 0.65. Alternatively, any other suitable ratio disclosed herein (among other ratios) may be used.

Figure 49:
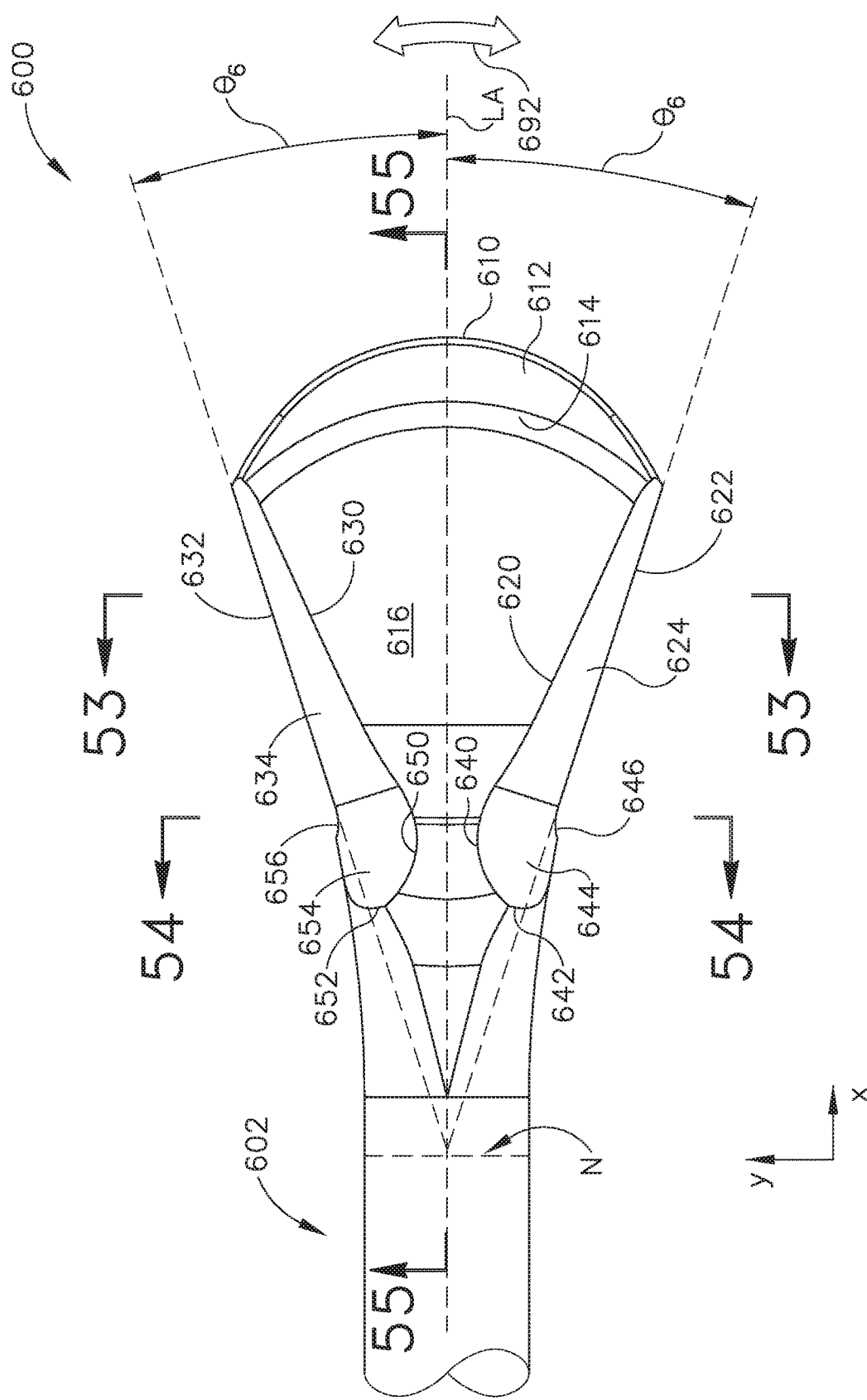
FIG. 49 depicts a top plan view of the blade of FIG. 47.
Figure 50:
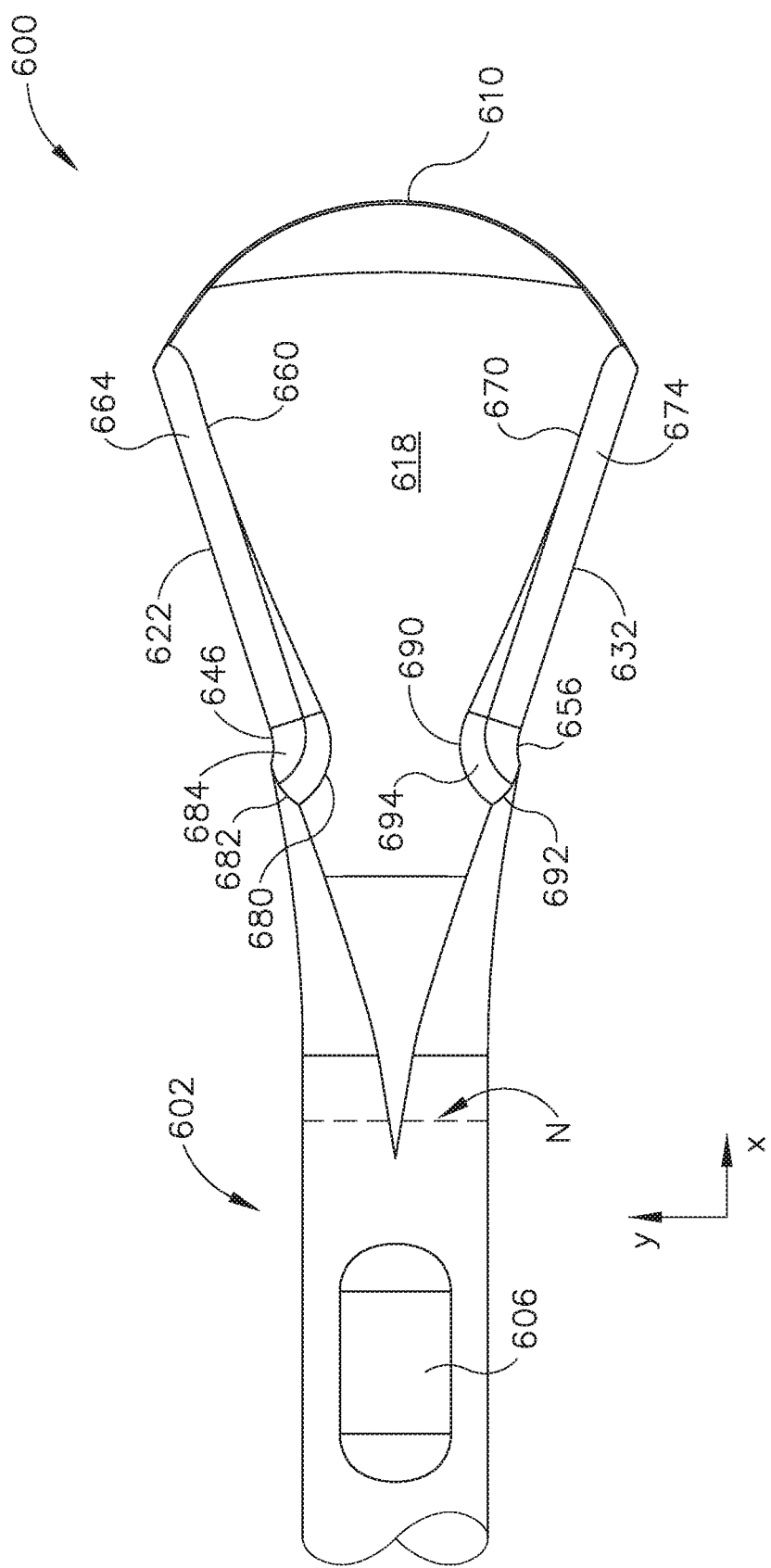
FIG. 50 depicts a bottom plan view of the blade of FIG. 47.

Blade (600) of this example comprises a distally located and laterally presented first face (612). First face (612) is partially bound by a curved distal edge (610) and a curved proximal edge (614). FIGS. 49-50 show the curvature of edges (610, 614) along an x-y plane. In some versions, edges (610, 614) have the same radius of curvature along the x-y plane. Alternatively, in the present example edges (610, 614) have different radii of curvature along the x-y plane. By way of example only, the radius of curvature of edge (610) along the x-y plane is between approximately 0.10 inches and approximately 0.25 inches; while the radius of curvature of edge (614) along the x-y plane is between approximately 0.180 inches and approximately 0.300 inches. As another merely illustrative example, the curvature of edges (610, 614) along the x-y plane may be the same as the curvature along the x-y plane in a distal edge of a conventional Cobb elevator instrument. Alternatively, any other suitable radius of curvature may be used along the x-y plane. It should also be understood that edges (610, 614) may have different respective radii of curvature along the x-y plane.

Figure 51:
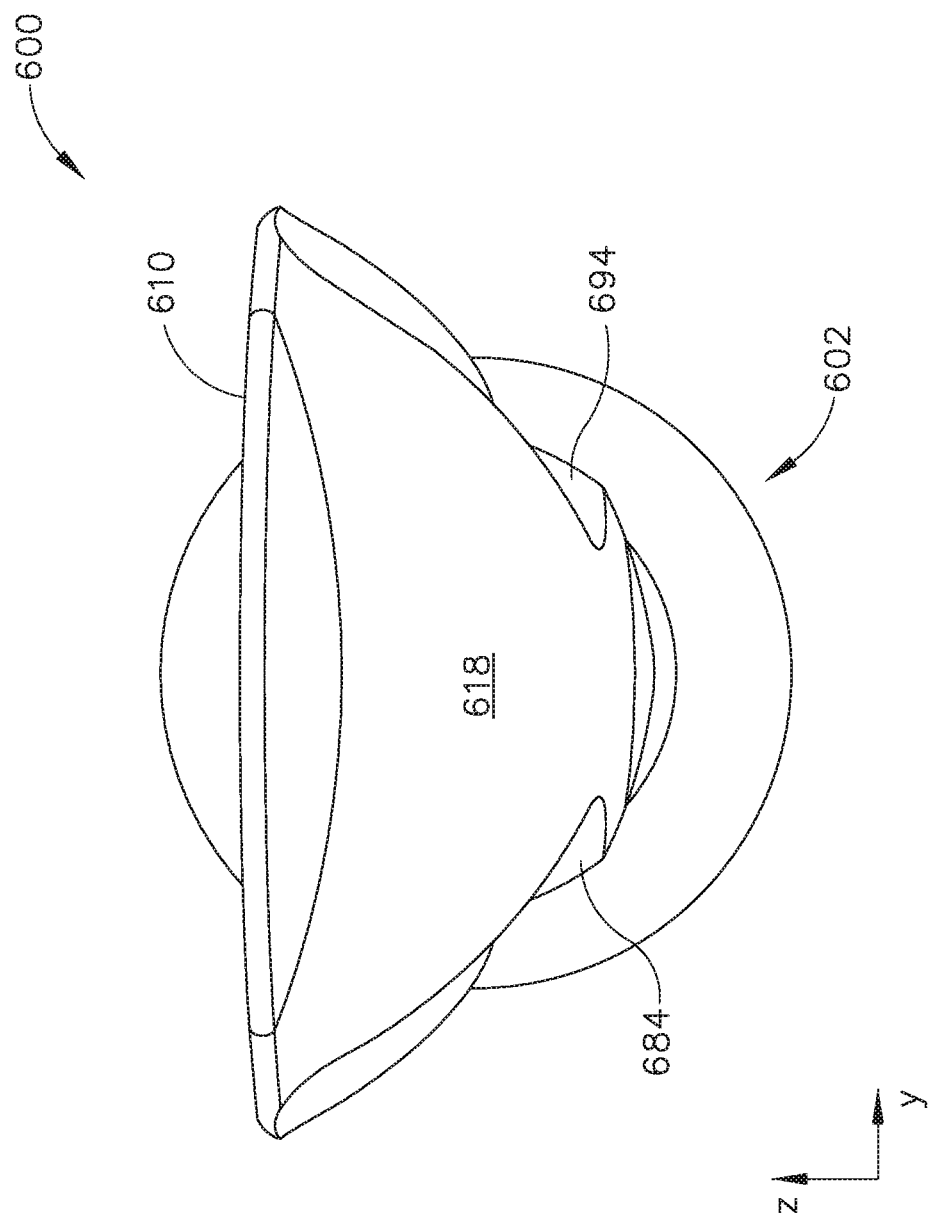
FIG. 51 depicts a front end view of the blade of FIG. 47.

FIG. 51 shows the profile of distal edge (610) along a y-z plane. In the present example, distal edge (610) is flat along the y-z plane. In some other versions distal edge (610) has a non-zero radius of curvature along the y-z plane. Proximal edge (614), distal edge (610), and/or first face (612) may have the same radius of curvature along the y-z plane. Alternatively, any other suitable radius of curvature may be used along the y-z plane, including wherein first face (612) is convex with respect to the y-z plane. It should also be understood that edges (610, 614) and first face (612) may be flat along the y-z plane.

Figure 52:
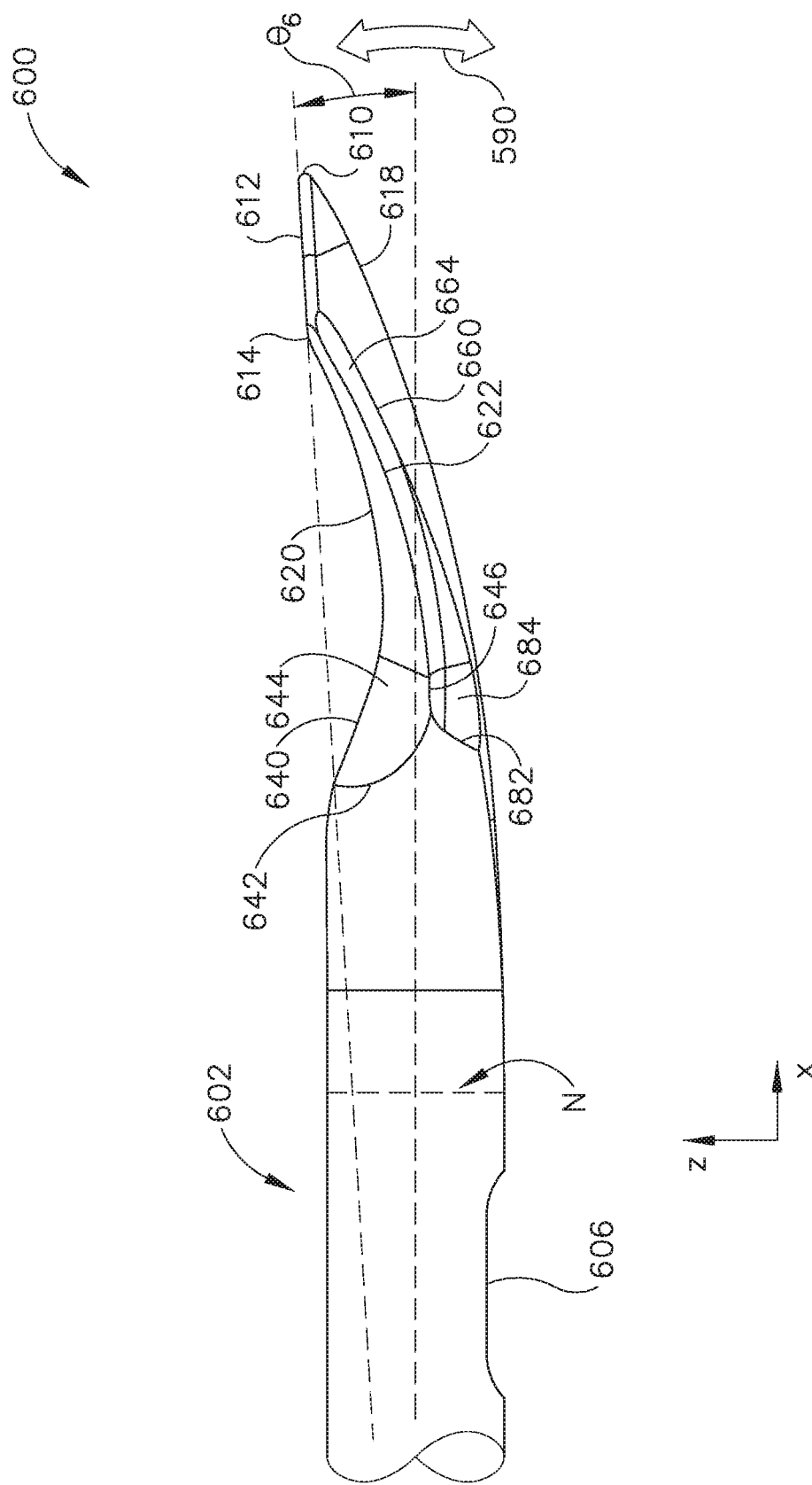
FIG. 52 depicts a side elevational view of the blade of FIG. 47.

As best seen in FIG. 52, first face (612) defines an angle ($\theta_7$) with the longitudinal axis (LA) along the x-z plane. By way of example only, angle ($\theta_7$) may be between approximately 0 degrees and approximately 10 degrees. As another merely illustrative example, first face (612) may define an angle ($\theta_7$) with the longitudinal axis (LA) that is the same as the corresponding angle defined by a corresponding face of a conventional Cobb elevator instrument. Alternatively, any other suitable value may be used. It should also be understood that first face (612) need not necessarily be straight along the x-z plane, such that first face (612) generally extends along angle ($\theta_7$). For instance, the center of each edge (610, 614) may be located along a respective line that defines angle ($\theta_7$) with the longitudinal axis (LA), while an intermediate portion of first face (612) bows outwardly in a convex configuration or inwardly in a concave configuration. First face (612) may also provide a convex configuration or a concave configuration along the y-z plane. Alternatively, first face (612) may be flat along the y-z plane.

In the present example, distal edge (610) is used to scrape tissue (e.g., muscle, tendon, ligament, periostium, etc.) from bone, and the radius of curvature of distal edge (610) is configured to prevent blade (600) from gouging bone while blade (600) performs such scraping. Such scraping may include movement of blade (600) along the longitudinal axis (LA) defined by waveguide (602), in the y direction, in the z direction, in an angular movement (arrow (690) in FIG. 52) about a pitch axis passing through the longitudinal axis (LA), and/or in an angular movement (arrow (692) in FIG. 49) about a yaw axis passing through the longitudinal axis (LA). The pitch and/or yaw axes may be located at a position along the longitudinal axis (LA) where the operator is gripping the instrument. Other suitable scraping motions will be apparent to those of ordinary skill in the art in view of the teachings herein. In some instances, blade (600) is ultrasonically inactive during such scraping operations. In some other instances, blade (600) is activated during such scraping operations. It should also be understood that first face (612) may be used as a coagulation flat. In other words, when the operator encounters a bleeder in tissue at the surgical site, first face (612) may be pressed against the bleeder while blade (600) is activated. This may coagulate or seal the bleeder/tissue.

Blade (600) of the present example also includes a pair of lateral edges (620, 630) extending proximally from edge (614) and another pair of lateral edges (622, 632) extending proximally from edge (610). As best seen in FIG. 49, edges (622, 632) are symmetric about the longitudinal axis (LA) of waveguide (602) in this example. In particular, edges (622, 632) each define the same angle ($\theta_6$) with the longitudinal axis (LA) along the x-y plane and are oriented such that the distance between edges (622, 632) increases along the length of blade (600) in the x direction. By way of example only, angle ($\theta_6$) may be between approximately 15 degrees and approximately 25 degrees. Alternatively, any other suitable value may be used. It should also be understood that edges (622, 632) need not necessarily be straight, such that edges (622, 632) generally extend along angle ($\theta_6$). For instance, the distal and proximal end of each edge (622, 632) may be located along a respective line that defines angle ($\theta_6$) with the longitudinal axis (LA), while an intermediate portion of each edge (622, 632) bows outwardly in a convex configuration or inwardly in a concave configuration along the x-y plane.

Edges (620, 630) are also symmetric about the longitudinal axis (LA) of waveguide (602) in this example. In particular, edges (620, 630) each define the same angle with the longitudinal axis (LA) along the x-y plane and are oriented such that the distance between edges (620, 630) increases along the length of blade (600) in the x direction. By way of example only, the angle defined between each edge (620, 630) and the longitudinal axis (LA) along the x-y plane may be between approximately 20 degrees and approximately 30 degrees. Alternatively, any other suitable value may be used. It should also be understood that edges (620, 630) need not necessarily be straight. For instance, the distal and proximal end of each edge (620, 630) may be located along a respective line that defines an angle with the longitudinal axis (LA), while an intermediate portion of each edge (620, 630) bows outwardly in a convex configuration or inwardly in a concave configuration along the x-y plane.

Figure 53:
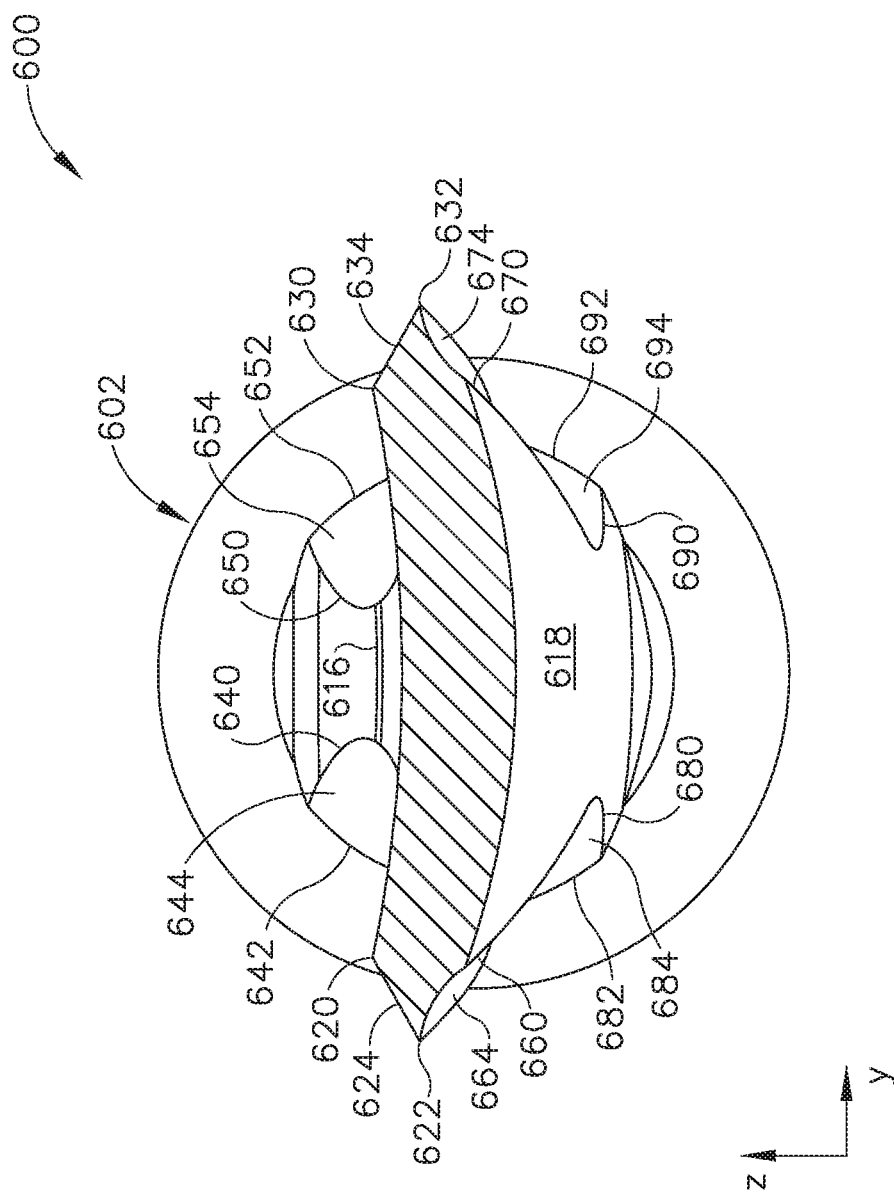
FIG. 53 depicts a cross-sectional view of the blade of FIG. 47, taken along line 53-53 of FIG. 49.

Edges (620, 622) partially bound a laterally presented second face (624); while edges (630, 632) partially bound a laterally presented third face (634). Faces (624, 634) are on opposite sides of blade (600) along the y axis. Faces (624, 634) are oriented obliquely and/or curved along the x-y plane (FIG. 49), along the x-z plane (FIG. 52), and along the y-z plane (FIG. 53). Edges (620, 622) distally converge at one end of distal edge (610); while edges (630, 632) distally converge at the other end of distal edge (610). Edges (610, 614) also converge and terminate at the same positions where edges (620, 622) converge and terminate and where edges (630, 632) converge and terminate. First face (612) is thus partially bound by edges (610, 614) with respect to the upper and lower orientations, partially bound by edge (620) proximate one end of distal edge (610), and partially bound by edge (630) proximate the other end of distal edge (610). As best seen in FIG. 53, and by comparing FIG. 49 with FIG. 50, faces (624, 634) are oriented upwardly and outwardly. In some versions, faces (624, 634) are flat. In some other versions, faces (624, 634) are convex along the y-z plane. In still other versions, faces (624, 634) are concave along the y-z plane. As yet another merely illustrative alternative, faces (624, 634) may each have at least one region that is convex along the y-z plane and at least one region that is concave along the y-z plane; or some other combination of convex, concave, and/or flat regions.

Figure 54:
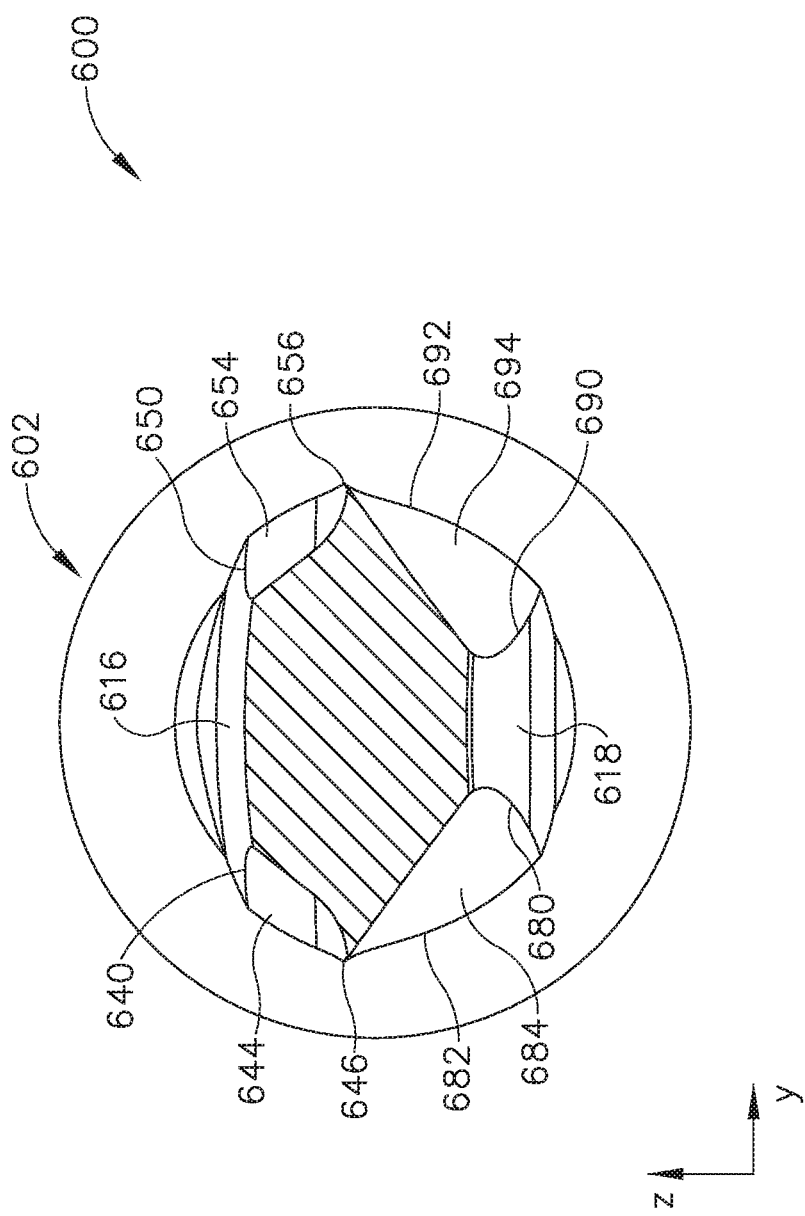
FIG. 54 depicts a cross-sectional view of the blade of FIG. 47, take along line 54-54 of FIG. 49.

As best seen in FIGS. 49, 52, and 54, blade (600) of this example further includes a proximal convex edge (640) and an adjacent proximal edge (642), which together partially bound a convex fourth face (644). Proximal convex edge (640) extends continuously from edge (620) described above. In some versions, edge (620) is substantially straight in the x-y plane while edge (640) is curved in the x-y plane. In versions where edge (620) has a radius of curvature along the x-y plane, edge (640) has a radius of curvature along the x-y plane that is less than the radius of curvature of edge (620) along the x-y plane. By way of example only, edge (640) may have a radius of curvature along the x-y plane between approximately 0.01 inches and approximately 0.10 inches. Alternatively, any other suitable radius of curvature may be used along the x-y plane. Fourth face (644) extends continuously from second face (624). The combination of faces (624, 644) is thus fully bound by edges (620, 622, 642, 640).

Similarly, blade (600) includes a proximal convex edge (650) and an adjacent proximal edge (652), which together partially bound a convex fifth face (654). Proximal convex edge (650) extends continuously from edge (630) described above. In some versions, edge (620) is substantially straight in the x-y plane while edge (650) is curved in the x-y plane. In versions where edge (630) has a radius of curvature along the x-y plane, edge (650) has a radius of curvature along the x-y plane that is less than the radius of curvature of edge (630) along the x-y plane. By way of example only, edge (650) may have a radius of curvature along the x-y plane between approximately 0.01 inches and approximately 0.10 inches. Alternatively, any other suitable radius of curvature may be used along the x-y plane. Fourth face (654) extends continuously from second face (632). The combination of faces (632, 654) is thus fully bound by edges (630, 632, 652, 650).

As best seen in FIGS. 48, 50, 52, and 54, the underside of blade (600) includes a pair of lateral edges (660, 670), which are symmetric about the longitudinal axis (LA) of waveguide (602) in this example. In particular, edges (660, 670) each define the same angle with the longitudinal axis (LA) along the x-y plane and are oriented such that the distance between edges (660, 670) increases along the length of blade (600) in the x direction. By way of example only, the angle defined between each edge (660, 670) and the longitudinal axis (LA) along the x-y plane may be between approximately 30 degrees and approximately 60 degrees. In some instances, the angle of edges (660, 670) is the same as the angle of edges (620, 630). Alternatively, any other suitable value may be used. It should also be understood that edges (660, 670) need not necessarily be straight. For instance, the distal and proximal end of each edge (660, 670) may be located along a respective line that defines an angle with the longitudinal axis (LA), while an intermediate portion of each edge (660, 670) bows outwardly in a convex configuration or inwardly in a concave configuration along the x-y plane.

Figure 48:
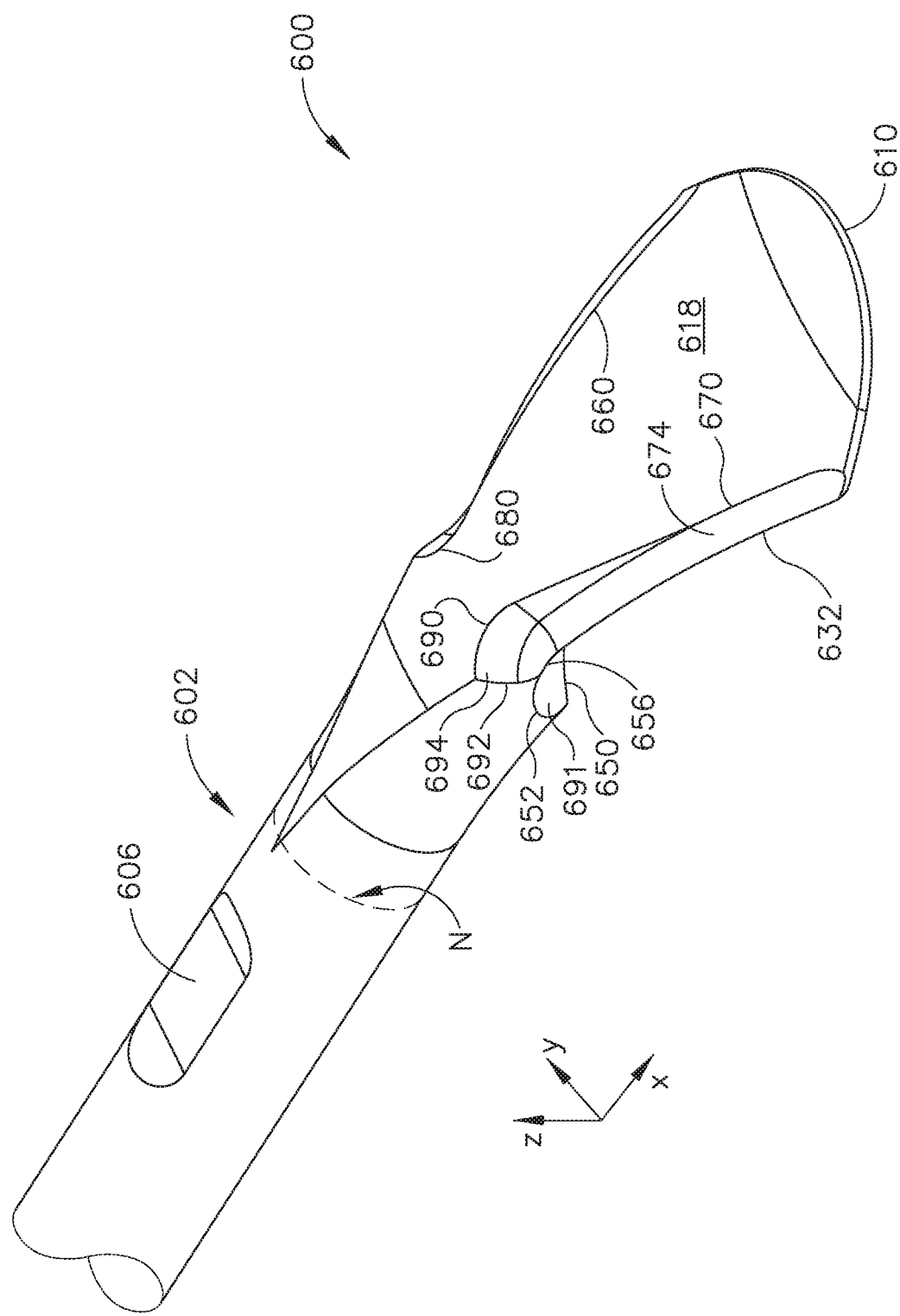
FIG. 48 depicts a bottom perspective view of the blade of FIG. 47.

Edges (660, 622) partially bound a laterally presented sixth face (664); while edges (670, 632) partially bound a laterally presented seventh face (674). Faces (664, 674) are on opposite sides of blade (600) along the y axis. Edges (660, 622) distally converge at one end of distal edge (610); while edges (670, 632) distally converge at the other end of distal edge (610). As best seen in FIGS. 48 and 53, faces (664, 674) are oriented downwardly and outwardly. In some versions, faces (664, 674) are that. In some other versions, faces (664, 674) are convex along the y-z plane. In still other versions, faces (664, 674) are concave along the y-z plane. As yet another merely illustrative alternative, faces (664, 674) may each have at least one region that is convex along the y-z plane and at least one region that is concave along the y-z plane; or some other combination of convex, concave, and/or flat regions.

As also seen in FIGS. 48, 50, 52, and 54, the underside of blade (600) further includes a proximal convex edge (680) and an adjacent proximal edge (682). A transition edge (646) extends between edge (682) and edge (622). As best seen in FIGS. 53-54, edges (622, 646) are substantially sharp. Proximal convex edge (680) extends continuously from edge (660) described above. Edges (680, 682, 646) together partially bound a convex eighth face (684). In some versions, edge (660) is substantially straight in the x-y plane while edge (680) is curved in the x-y plane. In versions where edge (660) has a radius of curvature along the x-y plane, edge (680) has a radius of curvature along the x-y plane that is less than the radius of curvature of edge (660) along the x-y plane. By way of example only, edge (680) may have a radius of curvature along the x-y plane between approximately 0.020 inches and approximately 0.080 inches. Alternatively, any other suitable radius of curvature may be used along the x-y plane. Eighth face (684) extends continuously from sixth face (664). The combination of faces (664, 684) is thus fully bound by edges (622, 660, 680, 682, 646).

Similarly, the underside of blade (600) includes a proximal convex edge (690) and an adjacent proximal edge (692). A transition edge (656) extends between edge (692) and edge (632). As best seen in FIGS. 53-54, edges (632, 656) are substantially sharp. Proximal convex edge (690) extends continuously from edge (670) described above. Edges (690, 692, 656) together partially bound a convex ninth face (694). In some versions, edge (660) is substantially straight in the x-y plane while edge (690) is curved in the x-y plane. In versions where edge (670) has a radius of curvature along the x-y plane, edge (690) has a radius of curvature along the x-y plane that is less than the radius of curvature of edge (670) along the x-y plane. By way of example only, edge (690) may have a radius of curvature along the x-y plane between approximately 0.020 inches and approximately 0.080 inches. Alternatively, any other suitable radius of curvature may be used along the x-y plane. Ninth face (694) extends continuously from seventh face (674). The combination of faces (674, 694) is thus fully bound by edges (632, 670, 690, 692, 656).

It should be understood that edges (620, 630, 622, 632, 640, 646, 650, 656) may be used to perform side cutting of tissue with blade (600). As one or more edges (620, 630, 622, 632, 640, 646, 650, 656) cut tissue, the corresponding face (644, 654, 684, 694) may assist in driving the tissue distally and outwardly away from blade (600). For instance, with tissue positioned against any one or more of edges (620, 630, 622, 632, 640, 646, 650, 656), blade (600) may be moved along the y axis, along the z axis, in an angular movement (arrow (690) in FIG. 52) about a pitch axis passing through the longitudinal axis (LA), and/or in an angular movement (arrow (692) in FIG. 49) about a yaw axis passing through the longitudinal axis (LA). Other suitable side cutting motions will be apparent to those of ordinary skill in the art in view of the teachings herein. The pitch and/or yaw axes may be located at a position along the longitudinal axis (LA) where the operator is gripping the instrument. In some instances, blade (600) is ultrasonically inactive during such side cutting operations. In some other instances, blade (600) is activated during such side cutting operations.

Figure 55:
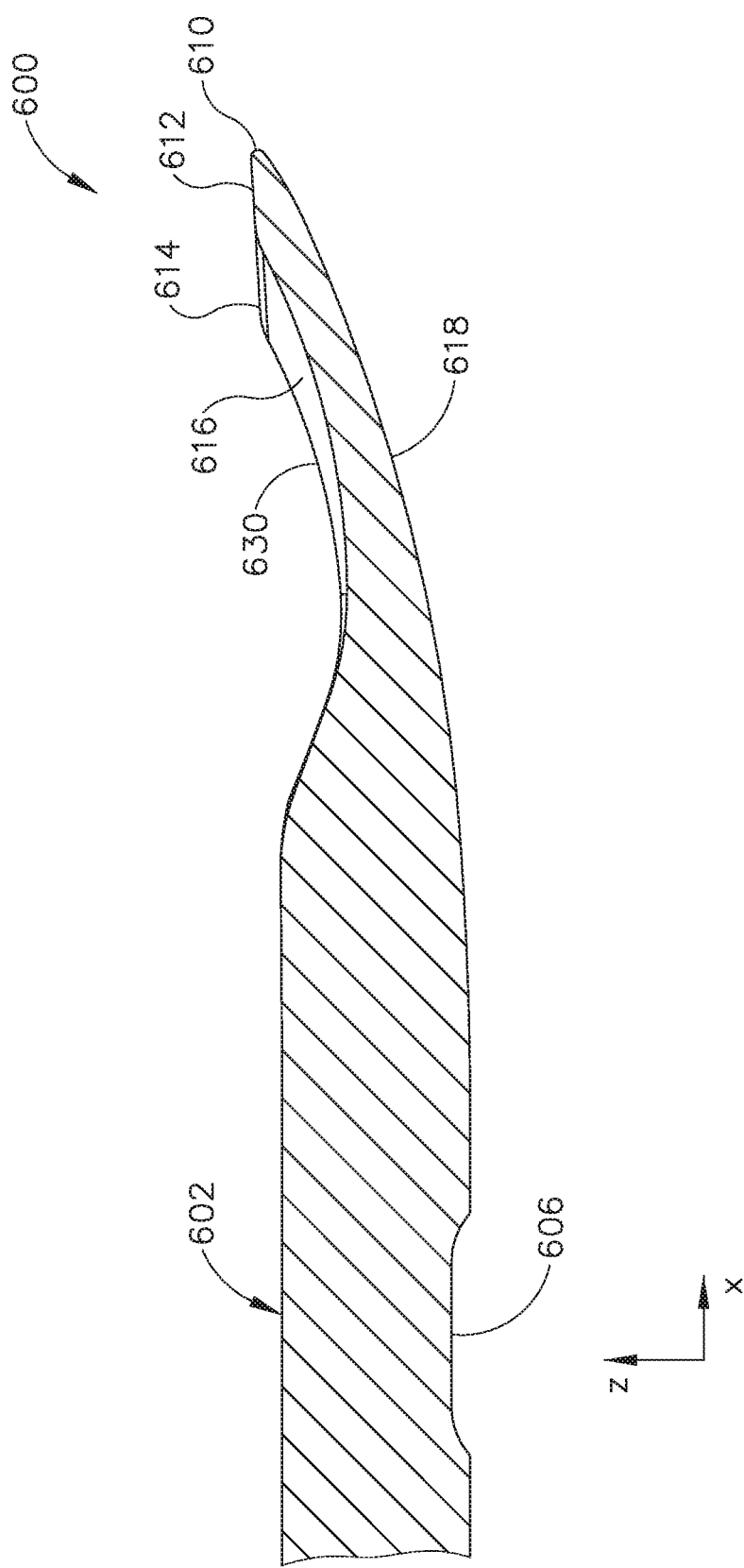
FIG. 55 depicts a cross-sectional view of the blade of FIG. 47, taken along line 55-55 of FIG. 49.

Blade (600) of the present example also includes a laterally presented, concave tenth face (616) and a laterally presented, convex eleventh face (616). As best seen in FIGS. 53-55, faces (616, 618) are on opposite sides of blade (600) along the z axis. The concavity of tenth face (616) is configured to allow tissue to gather within the recess provided by tenth face (616) as the tissue is scraped from bone by distal edge (610). eleventh face (616) is configured to provide a blunt camming surface to promote blunt dissection with blade (600). It should also be understood that eleventh face (616) may be used to provide coagulation. In other words, when the operator encounters a bleeder in tissue at the surgical site, eleventh face (616) may be pressed against the bleeder while blade (600) is activated. This may coagulate or seal the bleeder/tissue.

In some versions, faces (616, 618) have the same radius of curvature along the x-z plane. Alternatively, in the present example faces (616, 618) have different radii of curvature along the x-z plane. By way of example only, the radius of curvature of face (616) along the x-z plane is between approximately 0.40 inches and approximately 0.60 inches; while the radius of curvature of face (618) along the x-z plane is between approximately 1.0 inches and approximately 1.5 inches. In some versions, the curvature of tenth face (616) and/or eleventh face (616) along the x-z plane varies along the length of face (616, 618). As another merely illustrative example, tenth face (616) and/or eleventh face (616) may have a curvature along the x-z plane that is the same as the curvature of a corresponding faces a conventional Cobb elevator instrument. Alternatively, any other suitable radius or radii of curvature may be used along the x-z plane. It should also be understood that faces (616, 618) may have different respective radii of curvature along the x-z plane.

Similarly, faces (616, 618) may have the same radius of curvature along the y-z plane. Alternatively; in the present example faces (616, 618) have different radii of curvature along the y-z plane. By way of example only, the radius of curvature of face (616) along the y-z plane is between approximately 0.40 inches and approximately 0.60 inches; while the radius of curvature of face (618) along the y-z plane is between approximately 0.25 inches and approximately 0.45 inches. In some versions, the curvature of tenth face (616) and/or eleventh face (618) along the y-z plane varies along the width of face (616, 618). As another merely illustrative example, tenth face (616) and/or eleventh face (618) may have a curvature along the y-z plane that is the same as the curvature of a corresponding faces a conventional Cobb elevator instrument. Alternatively; any other suitable radius or radii of curvature may be used along the y-z plane, including wherein face (616) extends from edge (620) to edge (630) and is concave with respect to the y-z plane. It should also be understood that faces (616; 618) may have different respective radii of curvature along the y-z plane.

F. Exemplary Ultrasonic Blade with Lateral Scallop Features

Figure 56:
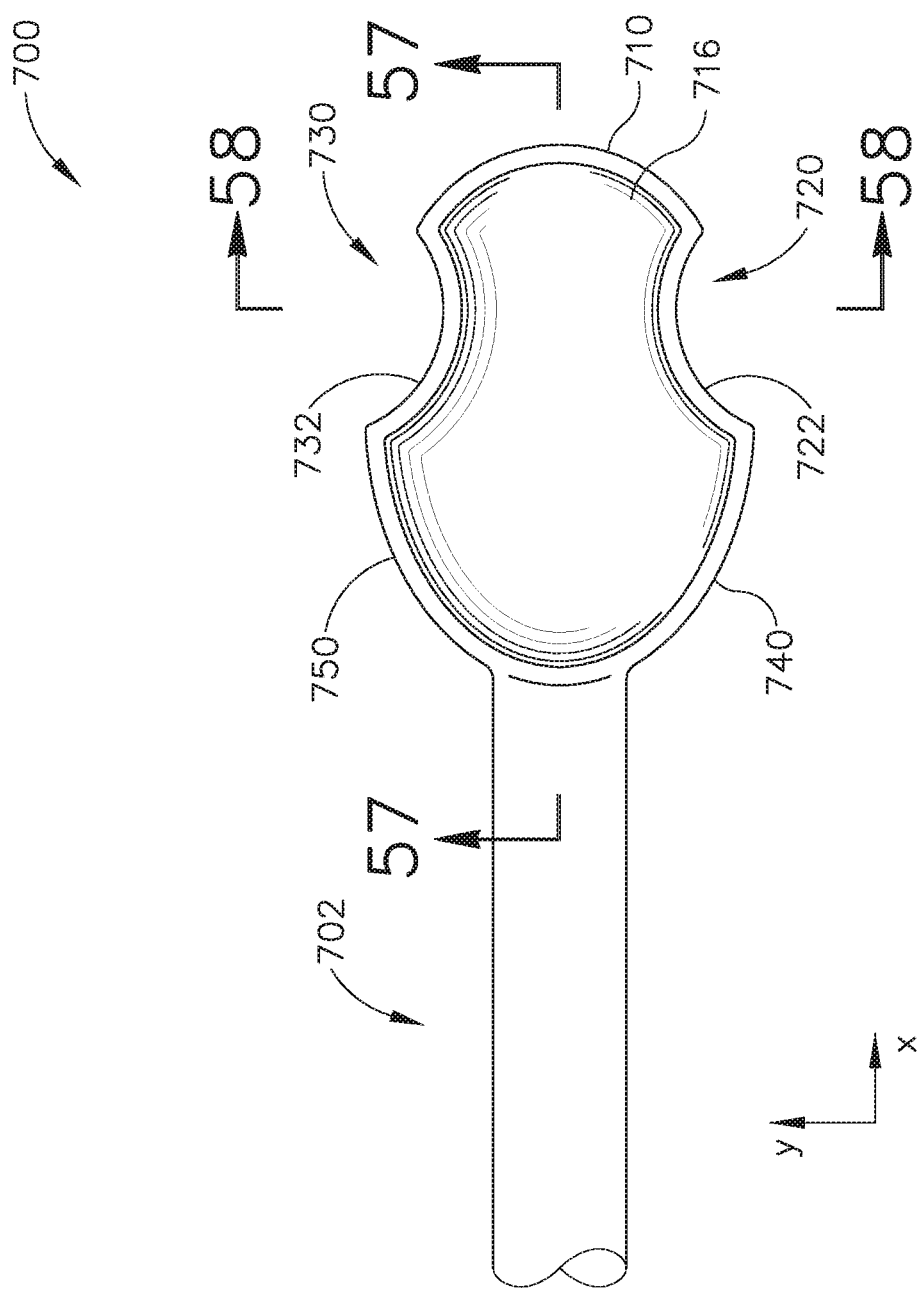
FIG. 56 depicts a top plan view of another exemplary alternative ultrasonic blade suitable for incorporation in the instrument of FIG. 2.
Figure 57:
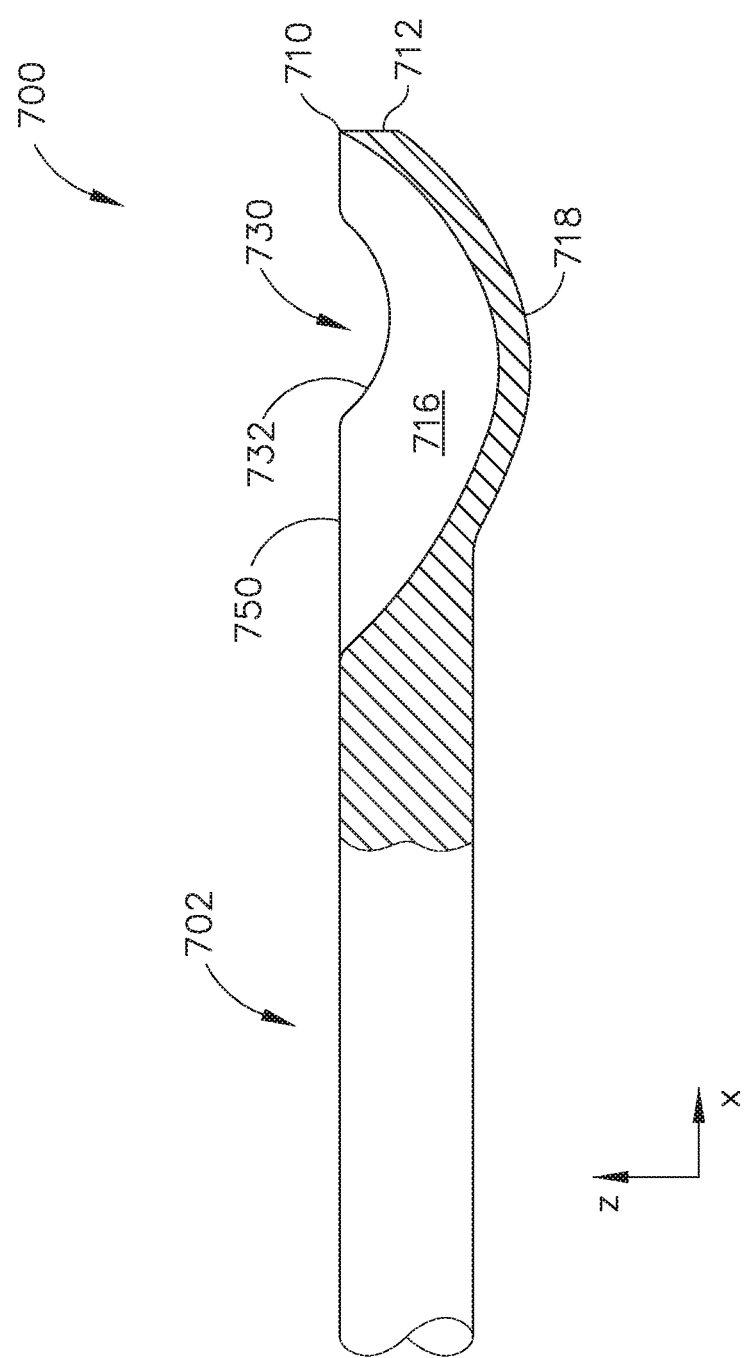
FIG. 57 depicts a cross-sectional view of the blade of FIG. 56, taken along line 57-57 of FIG. 56.
Figure 58:
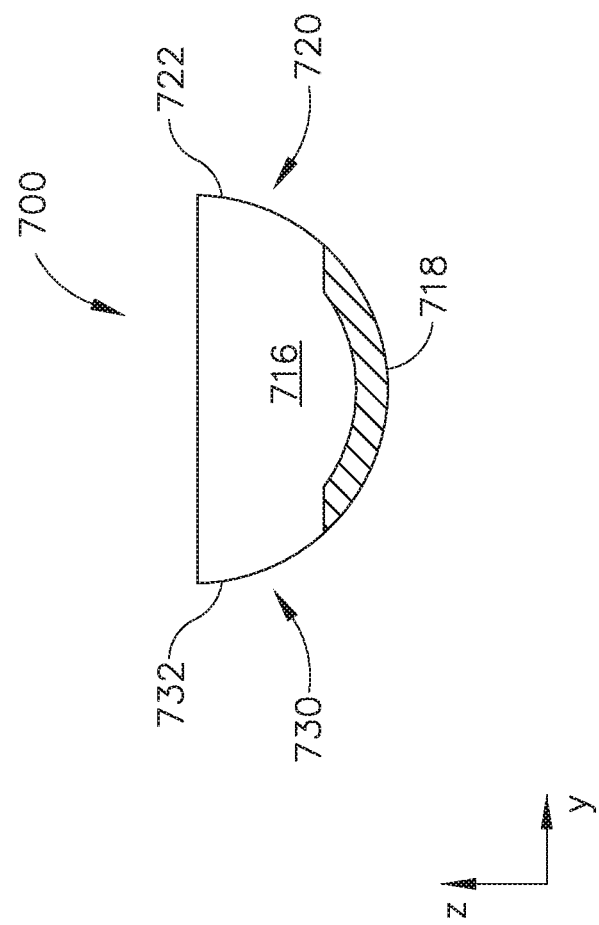
FIG. 58 depicts a cross-sectional view of the blade of FIG. 56, taken along line 58-58 of FIG. 56.

FIGS. 56-58 show an exemplary alternative ultrasonic blade (700) and waveguide (702) that may be readily incorporated into instrument (20, 120). In particular, blade (700) and waveguide (702) may be mechanically and acoustically coupled with transducer (26, 126) in place of waveguide (28, 128) and blade (24, 132). Blade (700) of this example comprises a curved distal edge (710). As best seen in FIG. 57, distal edge (710) substantially sharp in this example, though it should be understood that distal edge (710) may alternatively be blunt. Distal edge (710) may be used to scrape tissue (e.g., muscle, tendon, ligament, periostium, etc.) from bone. In some versions, distal edge (717) is configured to avoid gouging the bone during such scraping. Various suitable scraping motions will be apparent to those of ordinary skill in the art in view of the teachings herein. In some instances, blade (700) is ultrasonically inactive during such scraping operations. In some other instances, blade (700) is activated during such scraping operations.

Distal edge (710) proximally terminates at a pair of laterally oriented scallops (720, 730). Each scallop (720, 730) is defined by an inwardly directed concave edge (722, 732). Each concave edge (722, 732) is generally sharp in the present example. It should be understood that edges (722, 732) may be used to perform side cutting of tissue with blade (700). By way of example only, scallops (720, 730) may particularly facilitate cutting of tough tissues such as tendons, ligaments, etc. Various suitable side cutting motions will be apparent to those of ordinary skill in the art in view of the teachings herein. In some instances, blade (700) is ultrasonically inactive during such side cutting operations. In some other instances, blade (700) is activated during such side cutting operations. A pair of convex edges (740, 750) extend proximally from respective concave edges (720, 730). It should be understood that each edge (710, 722, 732, 740, 750) may have any suitable radius of curvature. Various suitable radii of curvature will be apparent to those of ordinary skill in the art in view of the teachings herein.

As best seen in FIGS. 57-58, blade (700) of this example further includes a concave inner surface (716) and a convex outer surface (718). Each surface (716, 718) may have any suitable radius of curvature. Various suitable radii of curvature will be apparent to those of ordinary skill in the art in view of the teachings herein. The concavity of inner surface (716) is configured to allow tissue to gather within the recess provided by inner surface (716) as the tissue is being scraped from bone by distal edge (710). Outer surface (718) is configured to provide a blunt camming surface to promote blunt dissection with blade (700). It should also be understood that outer surface (718) may be used to provide coagulation. In other words, when the operator encounters a bleeder in tissue at the surgical site, outer surface (718) may be pressed against the bleeder while blade (700) is activated. This may coagulate or seal the bleeder/tissue.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) an acoustic waveguide configured to be placed in acoustic communication with an ultrasonic transducer, wherein the acoustic waveguide defines a longitudinal axis; and
   (b) an ultrasonic blade in acoustic communication with the acoustic waveguide such that the acoustic waveguide is operable to communicate ultrasonic vibrations from an ultrasonic transducer to the ultrasonic blade, wherein the ultrasonic blade comprises:
      (i) a concave surface terminating distally into a first distal edge,
      (ii) a convex surface terminating distally into a second distal edge, wherein at least a portion of the first distal edge is proximal in relation to the second distal edge,
      (iii) a first surface at least partially defined between the first distal edge and the second distal edge, wherein the first surface extends away from the longitudinal axis in a distal direction; and
      (iv) a first pair of obliquely extending edges, wherein the first pair of obliquely extending edges diverge away from the longitudinal axis and away from each other along respective paths extending distally in relation to the acoustic waveguide, wherein the portion of first distal edge terminates into the first pair of obliquely extending edges.

2. The ultrasonic instrument of claim 1, wherein the ultrasonic blade further comprises a second pair of obliquely extending edges, wherein the second pair of obliquely extending edges diverge away from the longitudinal axis and away from each other along respective paths extending distally in relation to the acoustic waveguide.

3. The ultrasonic instrument of claim 2, wherein the second distal edge extends between the second pair of obliquely extending edges.

4. The ultrasonic instrument of claim 3, wherein the first pair of obliquely extending edges is located closer to the longitudinal axis as compared to the second pair of obliquely extending edges.

5. The ultrasonic instrument of claim 4, wherein corresponding edges of the first pair of obliquely extending edges and the second pair of obliquely extending edges each define a slanted surface.

6. The ultrasonic instrument of claim 1 wherein the first surface defines an angle between 0-10 degrees with the longitudinal axis.

7. The ultrasonic instrument of claim 1, wherein the first distal edge comprises an arched profile.

8. The ultrasonic instrument of claim 7, wherein the second distal edge comprises an arched profile.

9. The ultrasonic instrument of claim 8, wherein the first distal edge terminates at a first end point and a second end point.

10. The ultrasonic instrument of claim 9, wherein the second distal edge terminates at a third end point and a fourth end point.

11. The ultrasonic instrument of claim 10, wherein the first end point and the third end point define a third edge.

12. The ultrasonic instrument of claim 11, wherein the second end point and the fourth end point define a fourth edge.

13. The ultrasonic instrument of claim 1, wherein the acoustic waveguide and the ultrasonic blade are configured to provide ultrasonic vibration of the blade in a non-longitudinal mode of resonance, such that the ultrasonic blade is configured to vibrate with a lateral displacement from the longitudinal axis.

14. The ultrasonic instrument of claim 13, wherein the acoustic waveguide and the ultrasonic blade are configured to provide ultrasonic vibration of the blade with a ratio of lateral displacement to longitudinal displacement between approximately 0.46 to approximately 0.80.

15. The ultrasonic instrument of claim 1, wherein the acoustic waveguide and the ultrasonic blade are configured to provide ultrasonic vibration of the blade in a non-longitudinal mode of resonance.

16. The ultrasonic instrument of claim 15, wherein the non-longitudinal mode of resonance is vertical displacement from the longitudinal axis.

17. An ultrasonic instrument comprising:
(a) an ultrasonic transducer, wherein the ultrasonic transducer is operable to convert electrical power into ultrasonic vibrations;
(b) an acoustic waveguide in acoustic communication with the ultrasonic transducer, wherein the acoustic waveguide defines a longitudinal axis; and
(c) an ultrasonic blade in acoustic communication with the acoustic waveguide such that the ultrasonic transducer is operable to drive the ultrasonic blade to vibrate ultrasonically via the acoustic waveguide, wherein the ultrasonic blade comprises:
  (i) a concave surface extending distally away from the acoustic waveguide and terminating into a first distal edge,
  (ii) a convex surface extending distally away from the acoustic waveguide and terminating into a second distal edge, wherein at least a portion of the second distal edge is distal in relation to the first distal edge,
  (iii) an oblique surface extending between the first distal edge and the second distal edge, wherein the oblique surface extends distally away from the longitudinal axis; and
  (iv) a pair of obliquely extending edges extending away from each other distally relative to the acoustic waveguide, wherein a first obliquely extending edge of the pair of obliquely extending edges terminates into a first end of the first distal edge, wherein a second obliquely extending edge of the pair of obliquely extending edges terminates into a second end of the first distal edge, wherein the first end and the second end define a portion of the concave surface.

18. An ultrasonic instrument comprising:
(a) an ultrasonic transducer, wherein the ultrasonic transducer is operable to convert electrical power into ultrasonic vibrations;
(b) an acoustic waveguide in acoustic communication with the ultrasonic transducer, wherein the acoustic waveguide defines a longitudinal axis; and
(c) an ultrasonic blade in acoustic communication with the acoustic waveguide such that the ultrasonic transducer is operable to drive the ultrasonic blade to vibrate ultrasonically via the acoustic waveguide, wherein the ultrasonic blade comprises:
  (i) a concave surface extending distally away from the acoustic waveguide and terminating into a first arched distal edge,
  (ii) a convex surface extending distally away from the acoustic waveguide and terminating into a second arched distal edge, wherein the second arched distal edge has a larger radius than the first arched distal edge, and
  (iii) a surface extending between the first arched distal edge and the second arched distal edge, wherein the surface extends away from the longitudinal axis as the surface extends from the first arched distal edge toward the second arched distal edge;
  (iv) a first pair of obliquely extending edges, wherein the first pair of obliquely extending edges diverge away from the longitudinal axis and away from each other along respective paths extending distally in relation to the acoustic waveguide, wherein the first arched distal edge terminates into the first pair of obliquely extending edges.

* * * * *